(12) United States Patent
Quach et al.

(10) Patent No.: US 12,013,402 B2
(45) Date of Patent: Jun. 18, 2024

(54) CONCURRENT ANALYSIS OF MULTIPLE ANALYTES

(71) Applicant: The Regents of the University of California, Oakland, CA (US)

(72) Inventors: Austin Quach, Anaheim, CA (US); Kym Francis Faull, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 375 days.

(21) Appl. No.: 17/433,114

(22) PCT Filed: Mar. 27, 2020

(86) PCT No.: PCT/US2020/025488
§ 371 (c)(1),
(2) Date: Aug. 23, 2021

(87) PCT Pub. No.: WO2020/198688
PCT Pub. Date: Oct. 1, 2020

(65) Prior Publication Data
US 2022/0187306 A1 Jun. 16, 2022

Related U.S. Application Data

(60) Provisional application No. 62/825,610, filed on Mar. 28, 2019.

(51) Int. Cl.
*G01N 33/68* (2006.01)
*G01N 30/34* (2006.01)
(Continued)

(52) U.S. Cl.
CPC ......... *G01N 33/6848* (2013.01); *G01N 30/34* (2013.01); *G01N 30/7233* (2013.01);
(Continued)

(58) Field of Classification Search
CPC .. G01N 33/92; G01N 33/728; G01N 33/6848; G01N 30/72; G01N 30/96;
(Continued)

(56) References Cited

U.S. PATENT DOCUMENTS 7,593,108 B2 * 9/2009 Sterling ............... G01N 21/314
600/316
7,955,837 B2 * 6/2011 Pawlak ............. G01N 21/6428
435/7.1
(Continued)

FOREIGN PATENT DOCUMENTS

WO WO2010/141674 12/2010
WO WO2019/037465 2/2019

OTHER PUBLICATIONS

Extended European Search Report, dated Nov. 2, 2022, from corresponding European Patent Application No. 20779265.6.
(Continued)

*Primary Examiner* — An H Do
(74) *Attorney, Agent, or Firm* — Mark S. Cohen; PEARL COHEN ZEDEK LATZER BARATZ LLP

(57) ABSTRACT

Methods, apparatuses and systems are described that are capable of simultaneously determining the presence, identities or levels of multiple analytes present in a single sample, by carrying out steps including denaturation, normalization, extraction, mixed-mode liquid chromatography and mass spectrometry, whereby the presence, identities or levels of analytes in the single sample are determined.

20 Claims, 33 Drawing Sheets

(51) Int. Cl.

| | | |
|---|---|---|
| *G01N 30/72* | (2006.01) | |
| *G01N 30/96* | (2006.01) | |
| *G01N 33/50* | (2006.01) | |
| *G01N 33/70* | (2006.01) | |
| *G01N 33/72* | (2006.01) | |
| *G01N 33/92* | (2006.01) | |
| *G16H 10/40* | (2018.01) | |
| *G16H 50/20* | (2018.01) | |

(52) U.S. Cl.
CPC ......... *G01N 30/96* (2013.01); *G01N 33/5091* (2013.01); *G01N 33/6893* (2013.01); *G01N 33/70* (2013.01); *G01N 33/728* (2013.01); *G01N 33/92* (2013.01); *G16H 10/40* (2018.01); *G16H 50/20* (2018.01)

(58) Field of Classification Search
CPC ............... G01N 33/5091; G01N 30/34; G01N 33/6893; G01N 33/70; G01N 30/7233; G01N 33/6842; G01N 30/88; G01N 33/743; G01N 2800/60; G01N 2333/58; G01N 2333/775; G01N 2800/56; G01N 2333/47; G16H 10/40; G16H 50/20
See application file for complete search history.

(56) References Cited

U.S. PATENT DOCUMENTS

| | | | |
|---|---|---|---|
| 10,865,440 B2 * | 12/2020 | Eberhart | ................. B01L 3/527 |
| 2004/0166508 A1 | 8/2004 | Pawlak et al. | |
| 2005/0061967 A1 | 3/2005 | Shvartsburg et al. | |
| 2005/0118650 A1 | 6/2005 | Dasseux et al. | |
| 2006/0100792 A1 | 5/2006 | Natsume et al. | |
| 2008/0112853 A1 | 5/2008 | Hall | |
| 2011/0207227 A1 | 8/2011 | Menzel et al. | |
| 2012/0322160 A1 | 12/2012 | Park et al. | |

OTHER PUBLICATIONS

International Search Report and Written Opinion, dated Aug. 6, 2020, from corresponding International Application No. PCT/US20/25488.

Cajka et al., "Towards merging untargeted and targeted methods in mass spectrometry-based metabolomics and lipidomics", Anal. Chem. 2016, 88(1):524-545, Publication Date: Dec. 4, 2015; https://doi.org/10.1021/acs.analchem.5b04491.

Nakayasu et al. "MPLEx: a Robust and Universal Protocol for Single-Sample Integrative Proteomic, Metabolomic, and Lipidomic Analyses", mSystems, May 10, 2016; 1(3):e00043-16; doi: 10.1128/mSystems.00043-16.

Theodoridis et al., "Mass spectrometry-based holistic analytical approaches for metabolite profiling in systems biology studies", Mass Spectrometry Reviews, Mar. 7, 2011, 30(5): 884-906, https://doi.org/10.1002/mas.20306.

Office Action, dated Feb. 5, 2024, from corresponding European Patent Application No. 20779265.6.

Coman et al., "Simultaneous Metabolite, Protein, Lipid Extraction (Simplex): A Combinatorial Multimolecular Omics Approach for Systems Biology", Molecular & Cellular Proteomics, 15:1453-1466 (2016).

Sapcariu et al., "Simultaneous extraction of proteins and metabolites from cells in culture", MethodsX, 1:74-80 (2014).

Weckwerth et al., "Process for the integrated extraction, identification and quantification of metabolites, proteins and RNA to reveal their co-regulation in biochemical networks", Proteomics, 4: 78-83 (2004).

Vorreiter et al., "Comparison and optimization of methods for the simultaneous extraction of DNA, RNA, proteins, and metabolites", Analytical Biochemistry, 508:25-33 (2016).

* cited by examiner

CONCURRENT ANALYSIS OF MULTIPLE ANALYTES

CROSS-REFERENCE TO RELATED APPLICATIONS

This application claims the benefit of U.S. Provisional Patent Application No. 62/825,610, filed Mar. 28, 2019, which is entirely incorporated herein by reference for all purposes.

BACKGROUND

Conventional wisdom in analytical chemistry states that the vast chemical diversity found within biomolecules is too great to be studied using a single method. Consequently, efforts have been primarily dedicated to analyzing homogeneous subsets of biomolecules. Among these methods, liquid chromatography coupled to mass spectrometry (LC-MS) has emerged as an essential analytical platform in many of these analyses, being used in the characterization of numerous small molecules and macromolecules. Despite this versatility, LC-MS is still generally used in the analysis of single classes of biochemicals. There is growing interest in combining different layers of bioinformation in multi-omics studies. Multi-omics offers an opportunity to integrate various analyses, such as genomics, epigenomics, transcriptomics, proteomics, glycoproteomics, glycomics, lipidomics, metabolomics, fluxomics, ionomics, microbiomics, phenomics, metallomics, and exposomics, into one platform. However, these methods aim at integrating separate datasets using computational methods; the potential of combining these different classes of analytes prior to data acquisition remains unexplored.

It is towards the ability to perform combined analysis of diverse biomolecules into a single instrumental run that the present invention is directed.

SUMMARY

In an aspect, a method is provided for substantially simultaneously determining the presence, identities or amounts of multiple analytes present in a single sample, the method comprising:
  a. treating the sample with a denaturation reagent that denatures biopolymers in the sample thereby forming a denatured sample, wherein the denaturation reagent or treatment does not denature components of a normalization reagent when added thereto;
  b. treating the denatured sample with the normalization reagent, wherein the normalization agent converts the multiple analytes in the denatured sample into normalized analyte species and normalized analyte fragment species, the species capable of being separated by multiple modes of chromatography and individually identified by mass spectrometry, thereby forming a normalized sample;
  c. treating the normalized sample with an extraction reagent and retaining the soluble analyte species and analyte fragment species therein, thereby forming an extracted sample;
  d. subjecting the extracted sample to multiple modes of chromatography followed by mass spectrometry (MS), whereby data therefrom for each normalized analyte species and normalized analyte fragment species present therein are generated; and
  e. computationally determining from the data the presence, identities or levels of the multiple analytes present in the extracted sample.

In some embodiments of the method for substantially simultaneously determining the presence, identities or amounts of multiple analytes present in the single sample, the multiple analytes comprise chemically-related and chemically-unrelated analytes. In some embodiments, the analytes comprise proteins, carbohydrates, nucleic acids, lipids, electrolytes, metals, metabolites, volatile compounds, exogenous chemicals, or any combination thereof. In some embodiments, the analytes comprise proteins, carbohydrates, nucleic acids, lipids, electrolytes, metals, small molecules, volatile compounds, exogenous chemicals, or any combination thereof. In some embodiments, the sample is a biological sample. In some embodiments, the sample is whole blood, plasma, serum, urine, feces, cerebrospinal fluid, saliva, sweat, saliva, cells or a tissue sample. In some embodiments, the sample comprises an aqueous solution, an aqueous suspension or aqueous tissue. In some embodiments, the sample may be homogenized prior to or during step (a). In some embodiments, the denaturation reagent or treatment comprises one or more solvents, one or more chaotropic agents, heat, pressure, irradiation, one or more reference standards, or any combination thereof. In some embodiments, the solvent may be methanol, ethanol or acetonitrile. In some embodiments, the solvent is methanol. In some embodiments, the aqueous sample is homogenized in about an equal amount of methanol. In some embodiments, the denaturation reagent or treatment further comprises a metal-chelation agent. In some embodiments, the metal-chelating agent is EDTA, EGTA or DMSA. In some embodiments, the metal-chelating agent is EDTA. In some embodiments, the denaturation step and treating the denatured sample with the normalization reagent are performed substantially simultaneously. In some embodiments, the normalization reagent comprises one or more enzymes that depolymerize biopolymers in the sample. In some embodiments, the normalization reagent comprises pancreatic endolytic enzymes. In some embodiments, the normalization reagent comprises one or more proteinases, one or more nucleases, one or more glycosidases, one or more lipases, one or more chelating agents, one or more buffering agents, one or more reducing agents, one or more derivatizing agents, or any combination thereof. In some embodiments, the derivatizing agent is iodoacetamide. In some embodiments, the normalization reagent comprises trypsin. In some embodiments, the normalization reagent comprises trypsin, ribonuclease A, EDTA, ammonium bicarbonate or amylase. In some embodiments, when the normalization reagent comprises DNase I, EDTA is not concurrently present. In some embodiments, the proteinase is added to the denatured sample concurrently or after incubation of the denatured sample with the other components of the normalization reagent. In some embodiments, the treating with the normalization agent comprises incubation for between 0 and about 24 hours at a temperature of about 37° C. In some embodiments, the extraction reagent is added at 1:1 (v/v) to the normalized sample. In some embodiments, the extraction reagent comprises acetonitrile and acetone. In some embodiments, the acetonitrile and acetone are present at 1:1 (v/v). In some embodiments, the retaining the soluble species therein is achieved by centrifugation or filtration. In some embodiments, the multiple modes of chromatography comprises a reverse phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, or any combination thereof. In some embodiments, a mobile phase further comprises one or more ionizing adductants. In some embodiments, the ionizing adductant is selected from ammonium, protons, sodium, acetate, formate, propionate, phosphate, medronate, urea, biuret, triuret, or any combination thereof. In some embodiments, the mass spectrometry data acquisition comprises high resolution full scans with low or high resolution MS2 data-independent or data-dependent acquisition with dynamic exclusion in both positive and negative ion modes. In some embodiments, the computationally determining from the LC-MS data the presence, identities or amounts of the multiple analytes present in the extracted sample comprises comparing the LC-MS data of the normalized analyte species or normalized analyte fragment species to the mass spectrometry of those species generated from known amounts of known analytes.

In an aspect, a method is provided for substantially simultaneously determining the presence, identities or amounts of multiple, chemically-related and chemically-unrelated analytes present in a single biological sample, wherein the sample is an aqueous sample, the method comprising:
 a. treating the sample with an equal volume of denaturation reagent comprising methanol, wherein the denaturation agent denatures biopolymers in the sample thereby forming a denatured sample, wherein the denaturation reagent or treatment does not denature components of a normalization reagent when added thereto;
 b. treating the denatured sample with the normalization reagent comprising 50 mM ammonium bicarbonate, 5 mM EDTA, 1:20 m/m trypsin:sample protein, pH 7.8, for 4 hours at 37° C., wherein the normalization agent converts the multiple analytes in the denatured sample into normalized analyte species and normalized analyte fragment species, the species capable of being separated by multiple modes of chromatography and individually identified by mass spectrometry, thereby forming a normalized sample;
 c. treating the normalized sample with an equal volume of extraction reagent comprising acetonitrile:acetone 1:1, centrifuging the sample and retaining the supernatant comprising soluble analyte species and analyte fragment species therein, thereby forming an extracted sample;
 d. subjecting the extracted sample to multiple modes of chromatography followed by mass spectrometry (MS), whereby data therefrom for each normalized analyte species and normalized analyte fragment species present therein are generated; and
 e. computationally determining from the data the presence, amounts or identities of the multiple analytes present in the extracted sample.

In an aspect, a method for determining a pathological condition of a living source, from which a biological sample is derived, comprising:
 a. substantially simultaneously determining the presence, identities or amounts of multiple analytes present in the biological sample in accordance with the method described above;
 b. comparing the presence, identities or amounts of the analytes therein to those of a biological sample from a living source sample without said pathology, wherein the pathological condition is identifiable from a change in the presence, identities or levels of multiple analytes; and
 c. determining the pathological condition of said living source.

In some embodiments of the method for determining the pathological condition of the living source, the results from determining the pathological condition are used to select or monitor intervention in the living source.

In an aspect, an apparatus is provided for substantially simultaneously determining the presence, identities or amounts of multiple analytes present in a single sample, the apparatus comprising:
 a. means for denaturing biopolymers in the sample thereby forming a denatured sample, wherein the denaturation does not denature components of a normalization reagent when added thereto;
 b. means for normalizing the sample wherein multiple analytes in the denatured sample are converted into normalized analyte species and normalized analyte fragment species, the species capable of being separated by multiple modes of chromatography and individually identified by mass spectrometry;
 c. means for extracting the normalized sample and retaining the soluble analyte species and analyte fragment species therein;
 d. means for subjecting the extracted sample to multiple modes of chromatography followed by mass spectrometry (MS), whereby data therefrom for each normalized analyte species and normalized analyte fragment species present therein are generated; and
 e. means for computationally determining from the data the presence, identities or amounts of the multiple analytes present in the extracted sample.

In some embodiments of the apparatus, the multiple analytes comprise chemically-related and chemically-unrelated analytes. In some embodiments, the analytes comprise proteins, carbohydrates, nucleic acids, lipids, electrolytes, metals, small molecules, volatile compounds, exogenous chemicals, or any combination thereof. In some embodiments, the sample is a biological sample. In some embodiments, the sample is whole blood, plasma, serum, urine, feces, cerebrospinal fluid, saliva, sweat, saliva, cells or a tissue sample. In some embodiments, the sample comprises an aqueous solution, an aqueous suspension or aqueous tissue. In some embodiments, means for homogenizing the sample is provided to prior or during Step (a). In some embodiments, means for denaturing biopolymers in the sample comprises use of a denaturation reagent or treatment comprising one or more solvents, one or more chaotropic agents, heat, pressure, irradiation, one or more reference standards, or any combination thereof. In some embodiments, the solvent is methanol, ethanol or acetonitrile. In some embodiments, the solvent is methanol. In some embodiments, the aqueous sample is homogenized in about an equal amount of methanol. In some embodiments, the denaturing further comprises metal chelation. In some embodiments, the metal chelation is provided by EDTA, EGTA or DMSA. In some embodiments, the metal chelating is provided by EDTA. In some embodiments, the denaturing and normalizing are performed substantially simultaneously. In some embodiments, the normalizing is achieved using a normalization reagent comprising one or more enzymes that depolymerize biopolymers in the sample. In some embodiments, the normalization reagent comprises pancreatic endolytic enzymes. In some embodiments, the normalization reagent comprises one or more proteinases, one or more nucleases, one or more glycosidases, one or more lipases, one or more chelating agents, one or more buffering agents, one or more reducing agents, one or more derivatizing agents, or any combination thereof. In some embodiments, the derivatizing agent is iodoacetamide. In some embodiments, the normalization reagent comprises trypsin. In some embodiments, the normalization reagent comprises trypsin, ribonuclease A, EDTA, ammonium bicarbonate or amylase. In some embodiments, when the normalization reagent comprises DNase I, EDTA is not concurrently present. In some embodiments, the proteinase is added to the denatured sample concurrently or after incubation of the denatured sample with the other components of the normalization reagent. In some embodiments, normalizing means comprises incubation for between 0 and about 24 hours at a temperature of about 37° C. In some embodiments, means for extracting is achieved using an extraction reagent added at 1:1 (v/v) to the normalized sample. In some embodiments, the extraction reagent comprises acetonitrile and acetone. In some embodiments, the acetonitrile and acetone are present at 1:1 (v/v). In some embodiments, means for the retaining the soluble species therein is achieved by centrifugation or filtration. In some embodiments, the means for multiple modes of chromatography comprises a reverse phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, or any combination thereof. In some embodiments, a mobile phase used in the chromatography further comprises one or more ionizing adductants. In some embodiments, the ionizing adductant is selected from ammonium, protons, sodium, acetate, formate, propionate, phosphate, medronate, urea, biuret, triuret, or any combination thereof. In some embodiments, the mass spectrometry data acquisition comprises high resolution full scans with low or high resolution MS2 data-independent or data-dependent acquisition with dynamic exclusion in both positive and negative ion modes. In some embodiments, the means for computationally determining from the LC-MS data the presence, identities or amounts of the multiple analytes present in the extracted sample comprises comparing the LC-MS data of the normalized analyte species or normalized analyte fragment species to the mass spectrometry of those species generated from known amounts of known analytes.

In an aspect, a method for determining a condition of a living source, from which a biological sample is derived, comprising:
  a. substantially simultaneously determining the presence, identities or amounts of multiple analytes present in the biological sample by use of the apparatus described above;
  b. comparing the presence, identities or amounts of the analytes therein to those of a biological sample from a living source sample without said pathology, wherein the pathological condition is identifiable from a change in the presence, identities or amounts of multiple analytes; and
  c. determining the pathological condition of said living source.

In some embodiments of the method of the immediate preceding paragraph, the determining the condition is used to select or monitor intervention in the living source.

In an aspect, a system is provided for substantially simultaneously determining the presence, identities or amounts of multiple, chemically-related and chemically-unrelated analytes present in a single sample, the system comprising:
  a. a denaturation reagent or treatment that denatures biopolymers in the sample thereby forming a denatured sample, wherein the denaturation reagent or treatment does not denature components of a normalization reagent when added thereto;
  b. a normalization reagent that converts the multiple analytes in the sample into normalized analyte species or normalized analyte fragment species capable of being separated by mixed mode liquid chromatography and individually identified by tandem mass spectrometry;
  c. an extraction reagent that extracts the soluble analyte species and analyte fragment species;
  d. a separation process for retaining the soluble analyte species and analyte fragment species therein, thereby forming an extracted sample;
  e. multiple modes of chromatography that resolves soluble analyte species and analyte fragment species;
  f. mass spectrometry that generates data on the individual species; and
  g. one or more algorithms for computationally determining from the data of each normalized analyte species and normalized analyte fragment species the presence, identities or levels of the multiple analytes present in the sample.

In some embodiments of the system, the multiple analytes comprise chemically-related and chemically-unrelated analytes. In some embodiments, the analytes comprise proteins, carbohydrates, nucleic acids, lipids, electrolytes, metals, small molecules, volatile compounds, exogenous chemicals, or any combination thereof. In some embodiments, the sample is a biological sample. In some embodiments, the sample is whole blood, plasma, serum, urine, feces, cerebrospinal fluid, saliva, sweat, saliva, cells or a tissue sample. In some embodiments, the sample comprises an aqueous solution, an aqueous suspension or aqueous tissue. In some embodiments, prior to or during step (a), the sample is homogenized. In some embodiments, the denaturation reagent or treatment comprises one or more solvents, one or more chaotropic agents, heat, pressure, irradiation, one or more reference standards, or any combination thereof. In some embodiments, the solvent is methanol, ethanol or acetonitrile. In some embodiments, the solvent is methanol. In some embodiments, the aqueous sample is homogenized in about an equal amount of methanol. In some embodiments, the denaturation reagent or treatment further comprises a metal-chelation agent. In some embodiments, the metal-chelating agent is EDTA, EGTA or DMSA. In some embodiments, the metal-chelating agent is EDTA. In some embodiments, the denaturation step and treating the denatured sample with the normalization reagent are performed substantially simultaneously. In some embodiments, the normalization reagent comprises one or more enzymes that depolymerize biopolymers in the sample. In some embodiments, the normalization reagent comprises pancreatic endolytic enzymes. In some embodiments, the normalization reagent comprises one or more proteinases, one or more nucleases, one or more glycosidases, one or more lipases, one or more chelating agents, one or more buffering agents, one or more reducing agents, one or more derivatizing agents, or any combination thereof. In some embodiments, the derivatizing agent is iodoacetamide. In some embodiments, the normalization reagent comprises trypsin. In some embodiments, the normalization reagent comprises trypsin, ribonuclease A, EDTA, ammonium bicarbonate or amylase.

In some embodiments, when the normalization reagent comprises DNase I, EDTA is not concurrently present. In some embodiments, the proteinase is added to the denatured sample concurrently or after incubation of the denatured sample with the other components of the normalization reagent. In some embodiments, the treating with the normalization agent comprises incubation for between 0 and about 24 hours at a temperature of about 37° C. In some embodiments, the extraction reagent is added at 1:1 (v/v) to the normalized sample. In some embodiments, the extraction reagent comprises acetonitrile and acetone. In some embodiments, the acetonitrile and acetone are present at 1:1 (v/v). In some embodiments, the retaining the soluble species therein is achieved by centrifugation or filtration. In some embodiments, the multiple modes of chromatography comprises a reverse phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, or any combination thereof. In some embodiments, a mobile phase used in the chromatography further comprises one or more ionizing adductants. In some embodiments, the ionizing adductant is selected from ammonium, protons, sodium, acetate, formate, propionate, phosphate, medronate, urea, biuret, triuret, or any combination thereof. In some embodiments, the mass spectrometry data acquisition comprises high resolution full scans with low or high resolution MS2 data-independent or data-dependent acquisition with dynamic exclusion in both positive and negative ion modes. In some embodiments, the computationally determining from the LC-MS data the presence, identities or amounts of the multiple analytes present in the extracted sample comprises comparing the LC-MS data of the normalized analyte species or normalized analyte fragment species to the mass spectrometry of those species generated from known amounts of known analytes.

In an aspect, a method for determining a pathological condition of a living source, from which a biological sample is derived, comprising:
 a. substantially simultaneously determining the presence, identities or amounts of multiple analytes present in the biological sample in accordance with the system described above;
 b. comparing the presence, identities or amounts of the analytes therein to those of a biological sample from a living source sample without said pathology, wherein the pathological condition is identifiable from a change in the presence, identities or amounts of multiple analytes; and
 c. determining the pathological condition of said living source.

In some embodiments of the method of the immediate preceding paragraph, the pathological condition is used to select or monitor therapeutic intervention in the living source.

In an aspect, the present disclosure provides methods for identifying a plurality of analytes of different types from a sample, comprising:
 (a) subjecting the sample containing or suspected of containing the plurality of analytes of different types to conditions sufficient to yield a solution comprising the plurality of analytes or derivatives thereof; and
 (b) using an instrument to process the solution to identify the plurality of analytes or derivatives thereof, thereby identifying the plurality of analytes, the plurality of analytes or derivatives thereof is identified in a single run of the instrument.

In some embodiments of the method for identifying the plurality of analytes of different types from the sample as described hereinabove or anywhere else herein, the plurality of analytes comprises at least three types of analytes selected from the group consisting of protein, nucleic acid, small molecule, lipid, carbohydrate, electrolyte, and metal. In some embodiments, the plurality of analytes comprises: at least one type of analyte selected from small molecule, lipid, and carbohydrate; and at least two types of analytes selected from protein, nucleic acid, electrolyte, and metal. In some embodiments, the plurality of analytes comprises: at least one type of analyte selected from protein, and nucleic acid; and at least two types of analytes selected from small molecule, lipid, and carbohydrate. In some embodiments, the plurality of analytes comprises small molecule, lipid, and protein. In some embodiments, the plurality of analytes comprises small molecule, lipid, carbohydrate, and protein. In some embodiments, the plurality of analytes comprises small molecule, lipid, carbohydrate, and electrolyte. In some embodiments, the plurality of analytes comprises small molecule, lipid, carbohydrate, electrolyte, and metal. In some embodiments, the plurality of analytes further comprises one or both of protein and nucleic acid. In some embodiments, the small molecule is an endogenous small molecule, an exogenous small molecule, or a combination thereof. In some embodiments, the plurality of analytes comprises an exogenous chemical. In some embodiments, at least one of the plurality of analytes is a volatile compound.

In some embodiments of the method for identifying the plurality of analytes of different types from the sample as described hereinabove or anywhere else herein, the plurality of analytes or derivatives thereof in the solution has a distribution of molecular size or mass that is different than the plurality of analytes contained or suspected of being contained in the sample. In some embodiments, the plurality of analytes or derivatives thereof in the solution comprises an amount of charged molecules, an amount of hydrophilic molecules, an amount of molecules with hydrophobic functionality, or any combination thereof that is different than the plurality of analytes contained or suspected of being contained in the sample. In some embodiments, the plurality of analytes or derivatives thereof in the solution has a greater percentage by mass of molecules that fall within a predetermined range than the plurality of analytes contained or suspected of being contained in the sample. In some embodiments, the plurality of analytes or derivatives thereof in the solution has a distribution of molecular size or mass that is narrower than the plurality of analytes contained or suspected of being contained in the sample. In some embodiments, the plurality of analytes or derivatives thereof in the solution has a greater percentage by mass of charged molecules than the plurality of analytes contained or suspected of being contained in the sample. In some embodiments, the plurality of analytes or derivatives thereof in the solution has a greater percentage by mass of hydrophilic molecules as measured by octanol-water partition coefficient than the plurality of analytes contained or suspected of being contained in the sample. In some embodiments, the plurality of analytes or derivatives thereof in the solution has a distribution of mass-to-charge ratio (m/z) that is narrower than the plurality of analytes contained or suspected of being contained in the sample such that the plurality of analytes or derivatives thereof in the solution has a greater percentage by mass of molecules that fall within a range detectable by mass spectrometry than the plurality of analytes contained or suspected of being contained in the sample. In some embodiments, the range detectable by mass spectrometry is between 100 Dalton per electron charge (Da/e) to 2,000 Da/e. In some embodiments, the plurality of analytes or derivatives thereof in the solution each have a mass-to-charge ratio (m/z) between 15 Dalton per electron charge (Da/e) to 4,000 Da/e.

In some embodiments of the method for identifying the plurality of analytes of different types from the sample as described hereinabove or anywhere else herein, (a) comprises one or any combination of the following to obtain a treated sample: (i) homogenizing the sample; (ii) contacting the sample with a denaturation agent, thereby changing the conformation of at least one of the plurality of analytes; (iii) contacting the sample with a chelating agent, thereby forming a chelate complex with at least one of the plurality of analytes; (iv) contacting the sample with a derivatizing agent, thereby forming a derivative of at least one of the plurality of analytes; (v) contacting the sample with a reducing agent, thereby modifying at least one of the plurality of analytes; and (vi) contacting the sample with an enzyme, thereby producing fragments of at least one of the plurality of analytes. In some embodiments, (iii) is performed one or more times. In some embodiments, (vi) is performed one or more times. In some embodiments, (i) is performed prior to or substantially simultaneously with (ii). In some embodiments, (ii) is performed substantially simultaneously with (iii). In some embodiments, (ii) is performed prior to or substantially simultaneously with (vi). In some embodiments, (vi) is performed substantially simultaneously with one or more of (iii), (iv), and (v). In some embodiments, (vi) is performed substantially simultaneously with (iv). In some embodiments, (vi) is performed substantially simultaneously with (iii) and (iv). In some embodiments, (iii) is performed at least twice, once substantially simultaneously with (i), and again substantially simultaneously with (vi). In some embodiments, (vi) is performed at least twice, once substantially simultaneously with (ii), and again substantially simultaneously with (iv). In some embodiments, the enzyme used in (vi), performed substantially simultaneously with (ii), is protease. In some embodiments, (i) is carried out in a mixture of water and methanol at a ratio between 1:5 and 5:1 by volume. In some embodiments, the denaturation agent comprises a solvent, a chaotropic agent, and a reference standard. In some embodiments, the solvent is selected from methanol, ethanol, and acetonitrile. In some embodiments, the solvent is methanol. In some embodiments, the chelating agent is selected, independently on each occurrence of (iii), from ethylenediaminetetraacetic acid (EDTA), ethylene glycol-bis(O-aminoethyl ether)-N,N,N',N'-tetraacetic acid (EGTA), and dimercaptosuccinic acid (DMSA). In some embodiments, the chelating agent is EDTA. In some embodiments, the derivatizing agent is a peptide alkylating agent. In some embodiments, the derivatizing agent is iodoacetamide. In some embodiments, the enzyme comprises one or any combination selected, independently on each occurrence of (vi), from the group consisting of nuclease, protease, glycosidase, and lipase. In some embodiments, the glycosidase is amylase. In some embodiments, the protease is trypsin. In some embodiments, the nuclease comprises one or both of DNase I and ribonuclease A. In some embodiments, DNase I and EDTA are not concurrently present in (vi). In some embodiments, (vi) is carried out in an ammonium bicarbonate buffer. In some embodiments, (vi) comprises incubating at about 37° C. for about 24 hours or less.

In some embodiments of the method for identifying the plurality of analytes of different types from the sample as described hereinabove or anywhere else herein, (a) further comprises extracting the plurality of analytes or derivatives thereof from the treated sample with an extraction reagent, thereby obtaining the solution. In some embodiments, the extracting comprises adding the extraction reagent at 1:1 by volume to the treated sample. In some embodiments, the extraction reagent comprises acetonitrile and acetone at 1:1 by volume. In some embodiments, (a) further comprises removing insoluble impurity from the solution by centrifugation or filtration.

In some embodiments of the method for identifying the plurality of analytes of different types from the sample as described hereinabove or anywhere else herein, (b) comprises subjecting the plurality of analytes or derivatives thereof to an electron beam, thereby generating at least one ionized form or fragment of at least one of the plurality of analytes or derivatives thereof. In some embodiments, (b) further comprises contacting the plurality of analytes or derivatives thereof with a mixed mode chromatography matrix, comprising at least three orthogonal chromatographic modes, where each of the at least three orthogonal chromatographic modes is configured to separate a given type of the plurality of analytes or derivatives thereof from the solution. In some embodiments, at least one of the orthogonal chromatographic mode separates from the solution at least one derivative of the analyte. In some embodiments, the mixed mode chromatography matrix comprises at least three properties selected from the group consisting of cation exchange properties, anion exchange properties, ion exclusion properties, ligand exchange properties, size exclusion properties, chiral properties, reverse-phase properties, affinity properties, hydrophilic properties, polydentate properties, or any combination thereof. In some embodiments, (b) further comprises eluting the plurality of analytes and derivatives thereof with at least three mobile phases. In some embodiments, a first fraction of the plurality of analytes and derivatives thereof is eluted by a first mobile phase, the first mobile phase comprises water and 0.1% formic acid (v/v); a second fraction of the plurality of analytes and derivatives thereof is eluted by a second mobile phase, the second mobile phase comprises acetonitrile and 0.1% formic acid (v/v); and a third fraction of the plurality of analytes and derivatives thereof is eluted by a third mobile phase, the third mobile phase comprises 1:1 (v/v) methanol/water, 200 mM ammonium acetate, and formic acid.

In some embodiments of the method for identifying the plurality of analytes of different types from the sample as described hereinabove or anywhere else herein, at least one of the at least three mobile phases, or at least one of the first mobile phase, the second mobile phase, and the third mobile phase comprises one or more ionizing adductants selected from the group consisting of ammonium, protons, sodium, acetate, formate, propionate, phosphate, medronate, urea, biuret, and triuret. In some embodiments, (b) comprises determining a mass of each of the plurality of analytes or derivatives thereof by mass spectrometry. In some embodiments, (b) comprises determining an amount of each of the plurality of analytes or derivatives thereof by mass spectrometry. In some embodiments, the mass spectrometry is low or high resolution full or fragmentation scan mass spectrometry generated by data-independent or data-dependent acquisition with or without dynamic exclusion in both positive and negative ion modes. In some embodiments, the determining the mass or the amount comprises comparing the low or high resolution mass spectrometric characteristics to one or more reference mass full or spectra. In some embodiments, the solution is an aqueous solution, optionally comprising a water-miscible organic solvent. In some embodiments, the sample is a biological sample.

In an aspect, the present disclosure provides methods for determining a disease or condition in a subject, comprising: (i) identifying a plurality of analytes, individually or collectively, known to be associated with the disease or condition from a single sample of the subject to obtain an identified amount for each of the plurality of analytes, the plurality of analytes comprises analytes of different types; (ii) determining a difference between a reference amount and the identified amount for the each of the plurality of analytes to obtain a plurality of difference values; and (iii) using a trained machine learning algorithm to determine the disease or condition based on the plurality of difference values.

In some embodiments of the method for determining the disease or condition in the subject as described hereinabove or anywhere else herein, (i) comprises: (a) subjecting the single sample containing or suspected of containing the plurality of analytes to conditions sufficient to yield a solution comprising the plurality of analytes or derivatives thereof; and (b) using the solution to identify the plurality of analytes or derivatives thereof, thereby identifying the plurality of analytes. In some embodiments, the trained machine learning algorithm is trained using a plurality of training samples comprising no more than 170 training samples. In some embodiments, the trained algorithm is trained using a plurality of training samples comprising no more than 30 training samples. In some embodiments, the trained algorithm is trained using a plurality of training samples comprising at least 30 training samples. In some embodiments, the trained machine learning algorithm is trained using a plurality of training samples comprising at least 170 training samples. In some embodiments, the method for determining a disease or condition in a subject further comprising, prior to (i), identifying the plurality of analytes from each of the plurality of training samples. In some embodiments, the disease or condition is determined at an accuracy of at least 80%. In some embodiments, the accuracy is at least 90%. In some embodiments, the disease or condition is selected from the group consisting of aging, cardiovascular disease, inflammation, heart failure, and dementia. In some embodiments, the plurality of analytes comprises one or more analytes selected from the group consisting of apolipoprotein B (apoB), cortisol, C-reactive protein (CRP), and N-terminal pro b-type natriuretic peptide (NT-ProBNP), and derivatives thereof. In some embodiments, the plurality of analytes comprises two or more analytes selected from the group consisting of ribonucleotide, deoxyribonucleotide, polypeptide, and metabolite. In some embodiments, the plurality of analytes comprises three or more analytes selected from the group consisting of ribonucleotide, deoxyribonucleotide, polypeptide, and metabolite. In some embodiments, the plurality of analytes comprises ribonucleotide, deoxyribonucleotide, and metabolite. In some embodiments, the plurality of analytes comprises polypeptide, and metabolite.

These and other aspects of the invention will be appreciated from the ensuing description of the drawings and detailed description of the invention.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION

Figure 1:
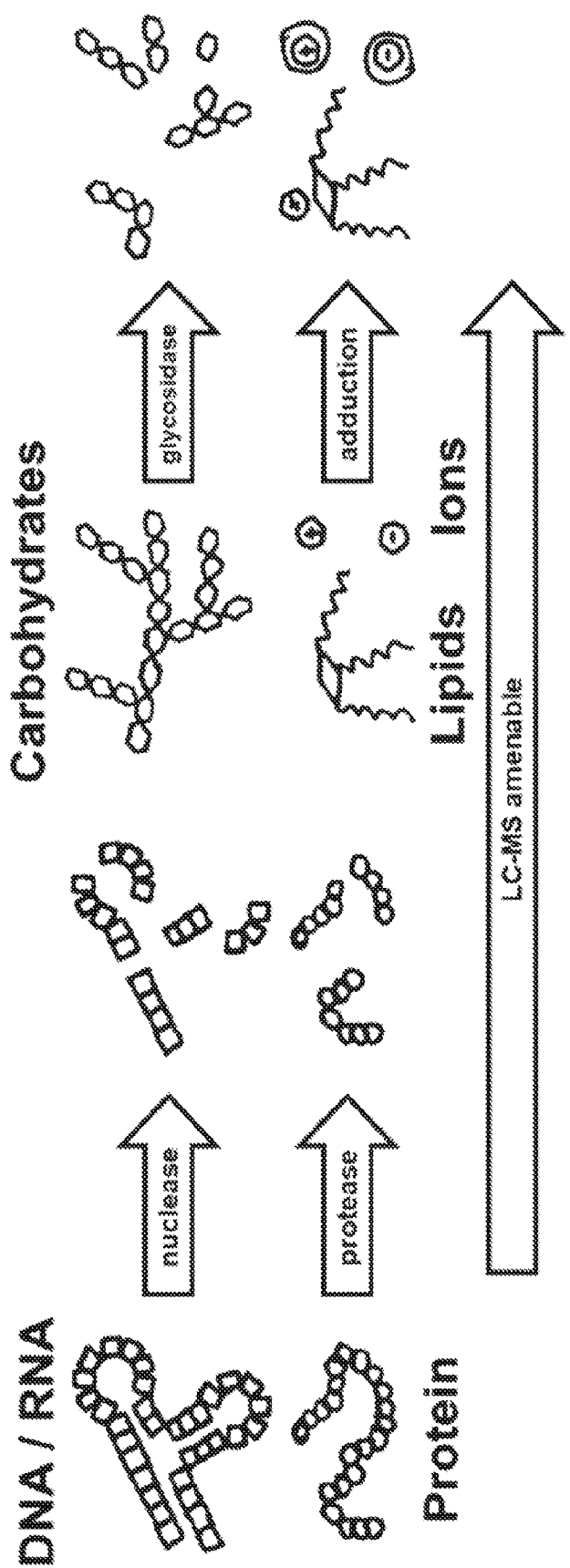
FIG. 1 shows the overall concept of the invention.

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure, the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value.

Similarly, when values are expressed as approximations, by use of the antecedent "about," it is understood that the particular value forms another embodiment. All ranges are inclusive and combinable. In the context of the present disclosure, by "about" a certain amount it is meant that the amount is within ±20% of the stated amount, or preferably within ±10% of the stated amount, or more preferably within ±5% of the stated amount.

As used herein, the terms "treat", "treatment", or "therapy" (as well as different forms thereof) refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented. As used herein, the terms "component," "composition," "formulation", "composition of compounds," "compound," "drug," "pharmacologically active agent," "active agent," "therapeutic," "therapy," "treatment," or "medicament," are used interchangeably herein, as context dictates, to refer to a compound or compounds or composition of matter which, when administered to a subject (human or animal) induces a desired pharmacological and/or physiologic effect by local and/or systemic action. A personalized composition or method refers to a product or use of the product in a regimen tailored or individualized to meet specific needs identified or contemplated in the subject.

The terms "subject," "individual," and "patient" are used interchangeably herein, and refer to an animal, for example a human, to whom treatment with a composition or formulation in accordance with the present invention, is provided. The term "subject" or "living source" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys. In certain embodiments, "living source" includes non-animal living organisms such as microorganisms, fungi, moss liverworts, and plants including but not limited to grains, fruits, vegetables and other human and animal comestibles including foodstuffs made from them. The compositions described herein can be used to treat any suitable mammal, including primates, such as monkeys and humans, horses, cows, cats, dogs, rabbits, and rodents such as rats and mice. In one embodiment, the mammal to be treated is human. The human can be any human of any age. In an embodiment, the human is an adult. In another embodiment, the human is a child. The human can be male, female, pregnant, middle-aged, adolescent, or elderly. According to any of the methods of the present invention and in one embodiment, the subject is human. In another embodiment, the subject is a non-human primate. In another embodiment, the subject is murine, which in one embodiment is a mouse, and, in another embodiment is a rat. In another embodiment, the subject is canine, feline, bovine, equine, laprine or porcine. In another embodiment, the subject is mammalian.

Conditions and disorders in a subject for which a particular drug, compound, composition, formulation (or combination thereof) is said herein to be "indicated" are not restricted to conditions and disorders for which that drug or compound or composition or formulation has been expressly approved by a regulatory authority, but also include other conditions and disorders known or reasonably believed by a physician or other health or nutritional practitioner to be amenable to treatment with that drug or compound or composition or formulation or combination thereof.

There is enormous interest in decoding the vast amounts of molecular information present in biological systems. Due to the overwhelming chemical diversity found in even simple biological samples, highly specialized analytical methods have been necessary to detect and measure the various subsets of analytes found in nature. The inventors describe a method using LC-MS to quantify a diverse range of molecular species in a single analytical run in a variety of biological specimens. This assay provides a straightforward approach for analyzing complex biochemical systems, presenting unique opportunities in biomedical research. This framework merges the analysis of a diverse biomolecules into a single instrumental run by combining orthogonal mixed-mode (or multiple modes of) chromatography with various steps and reagents in aimed at chemical normalization and inclusion prior to introducing the sample to the mass spectrometer. Using this approach, simultaneous quantification of thousands of proteins, lipids, small molecules, electrolytes and even oligosaccharides and oligonucleotides is provided (FIG. 1).

In one embodiment, biological samples are first homogenized and denatured in a methanolic solution. Analytes are then chemically normalized to improve LC-MS amenability, e.g. macromolecules are enzymatically hydrolyzed into small molecule-like fragments, and poorly detected molecules such as neutral lipids and electrolytes are paired with ionizing adductants. The LC-MS-incompatible debris is precipitated using water-miscible organic solvents, yielding an inclusive mixed-polarity extract after centrifugal clarification. The analytes are separated using orthogonal mixed mode (or multiple modes of) chromatography prior to mass spectrometric data acquisition. Full MS scans and MS/MS fragmentation scans are acquired for these multi-omic preparations with polarity switching to capture both positively and negatively ionizing molecules. A more detailed description of the sample processing methods can be found further below and in the Examples.

Figure 2:
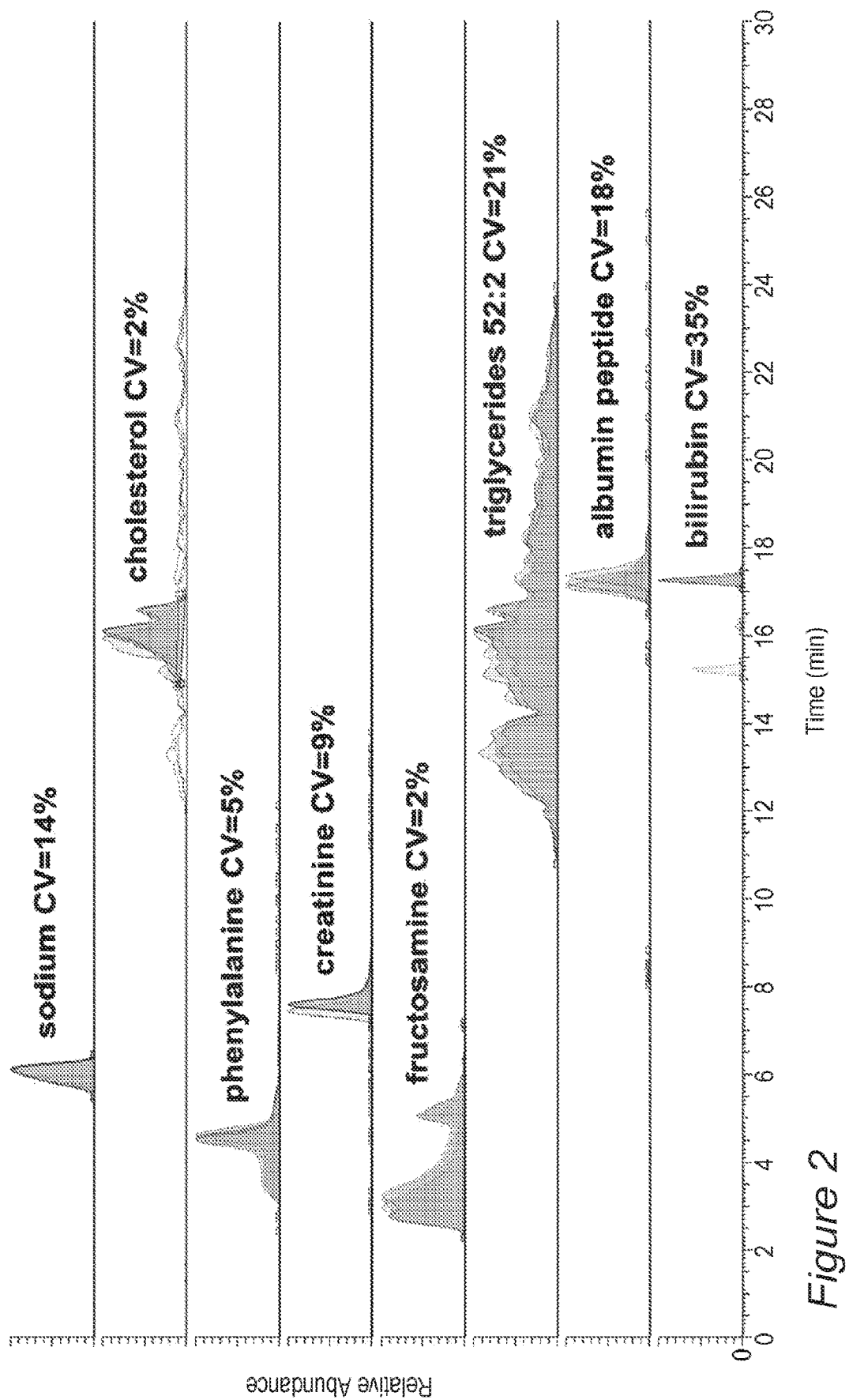
FIG. 2 shows selected analytes presented as detected in human plasma. Time and intensity peak area are represented on the horizontal and vertical axes respectively. The selected analytes are sodium, cholesterol, phenylalanine, creatinine, fructosamine (and isomer), triglyceride isomers (52:2), a tryptic albumin peptide, and bilirubin.

As will be shown in the examples below, to demonstrate that this method allows for separation and quantification of chemically diverse molecules, a set of representative analytes were selected for analysis, including proteins, lipids, metabolites and electrolytes. Most compounds were chromatographically retained except for polar neutral compounds such as sugars and oligosaccharides. These analytes were detectable in human plasma preparations at endogenous levels (FIG. 2).

Figure 3:
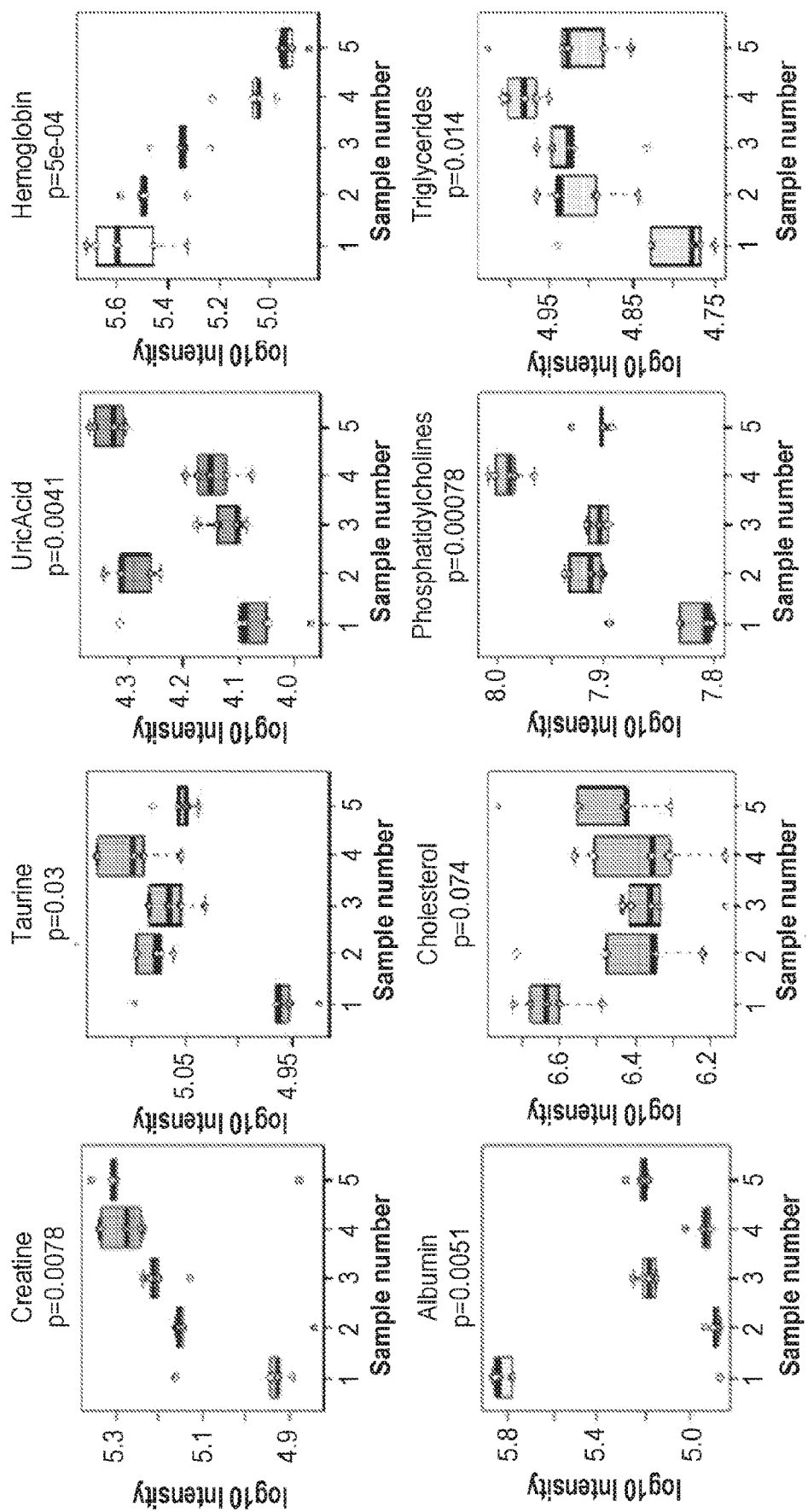
FIG. 3 shows box plots of select analytes across 5 different plasma samples in 5 replicates. The name of each analyte is listed above each dot plot with the Kruskal-Wallis p-value denoting whether any of the differences between the sample medians are statistically significant. Sample number and log 10-scaled intensity peak area are represented on the horizontal and vertical axes, respectively. The dots represent the quintuplicate measurements of each sample and the horizontal lines represent the quartiles of all replicates. The selected analytes are creatine, taurine, uric acid, a tryptic peptide of hemoglobin, a tryptic peptide of serum albumin, cholesterol, phosphatidylcholine isomers (34:2), and triglyceride isomers (52:2).

To demonstrate reproducibility of the method in quantification, 5 fasting plasma sample preparations were analyzed in quintuplicate. Inspecting a small set of representative analytes, measurements were sufficiently precise to differentiate between samples (FIG. 3). Label-free feature quantification of these data using the KNIME (v3.6.2) OpenMS (v2.4.0) plugin yielded 98,797 total de-isotoped features—12,150 of these features had mean intra-sample coefficients of variation (CVs) less than 20% and mean intra-sample CVs smaller than inter-sample CVs. Using narrowed precursor scan windows across ten 60-minute runs in a semi-exhaustive BoxCar-like data-dependent acquisition fragmentation scan analysis of pooled plasma, peptide matches were found for 2,559 protein families using Thermo Proteome Discoverer (v2.2.0) and 270 compound matches with Thermo Compound Discoverer (v2.0.0).

Figure 4:
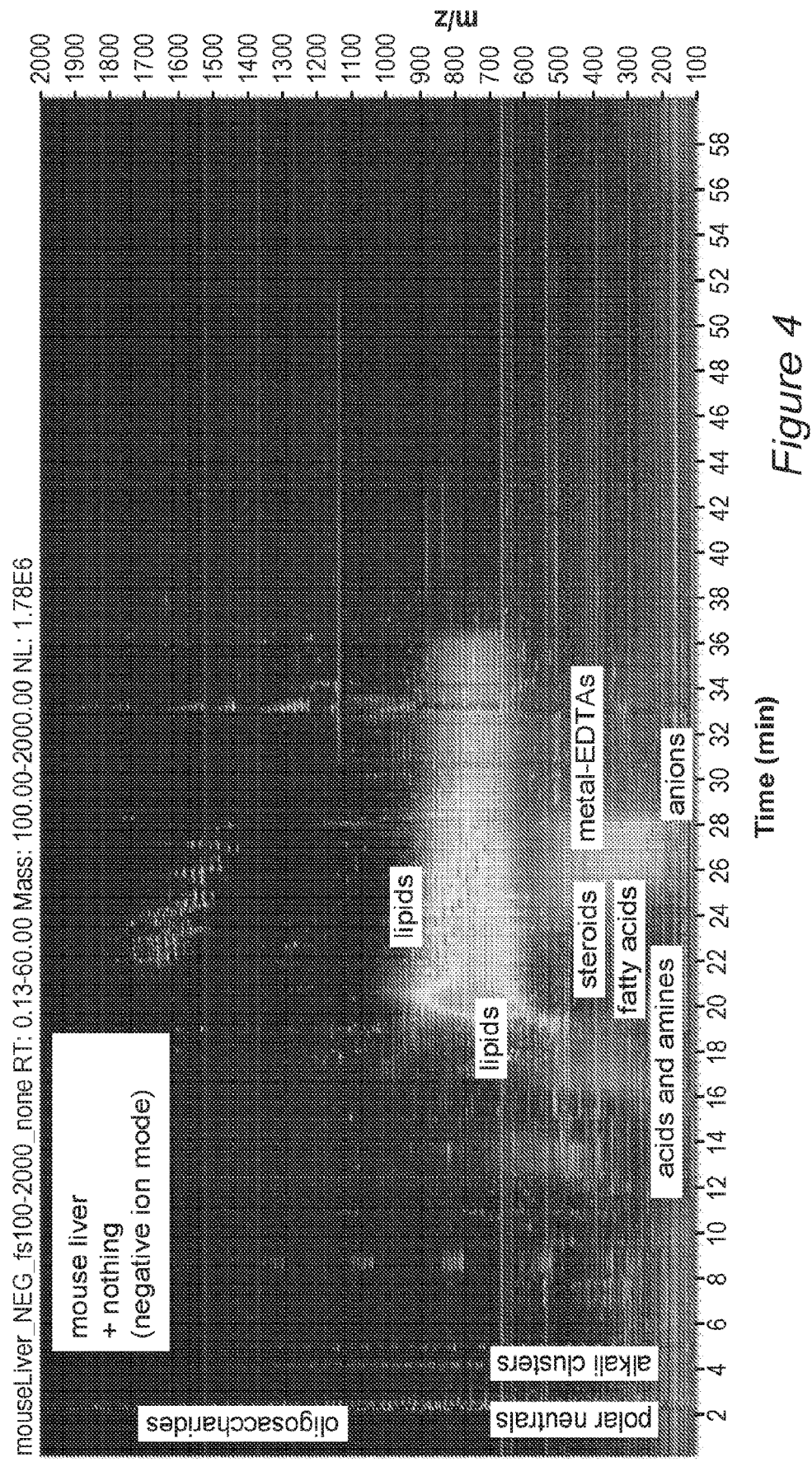
FIG. 4 shows the spectrum obtained from mouse liver homogenates that were digested without enzymes and analyzed according to the described procedures. Time and mass-to-charge are represented on the horizontal and vertical axes with increasing brightness of color representing higher ion intensity. Approximate positions of select analyte classes are labeled according to previous observations.
Figure 5:
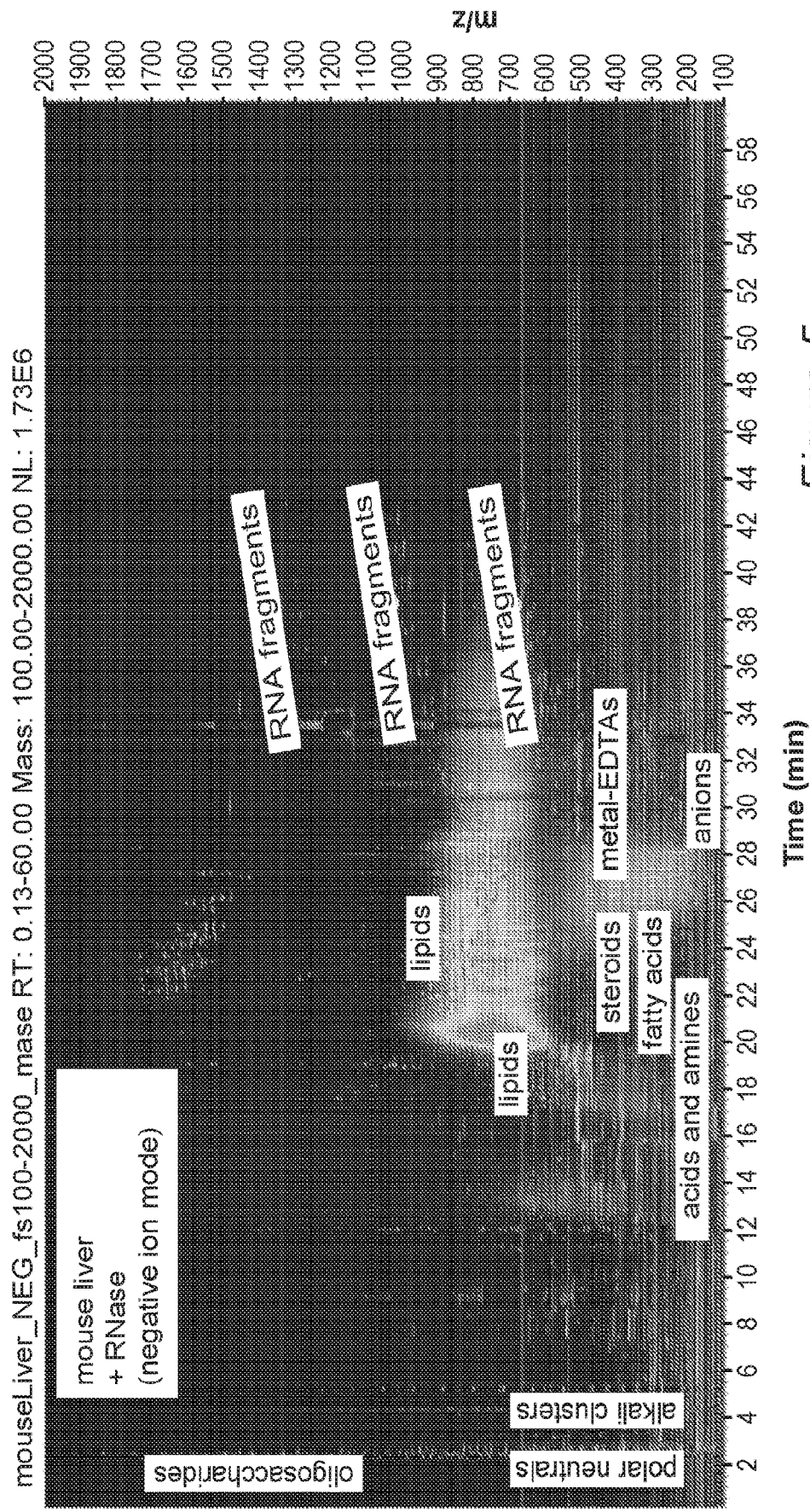
FIG. 5 shows the spectrum obtained from mouse liver homogenates that were digested with RNase A and analyzed according to the described procedures. Time and mass-to-charge are represented on the horizontal and vertical axes with increasing brightness of color representing higher ion intensity. Approximate positions of select analyte classes are labeled according to previous observations.
Figure 6:
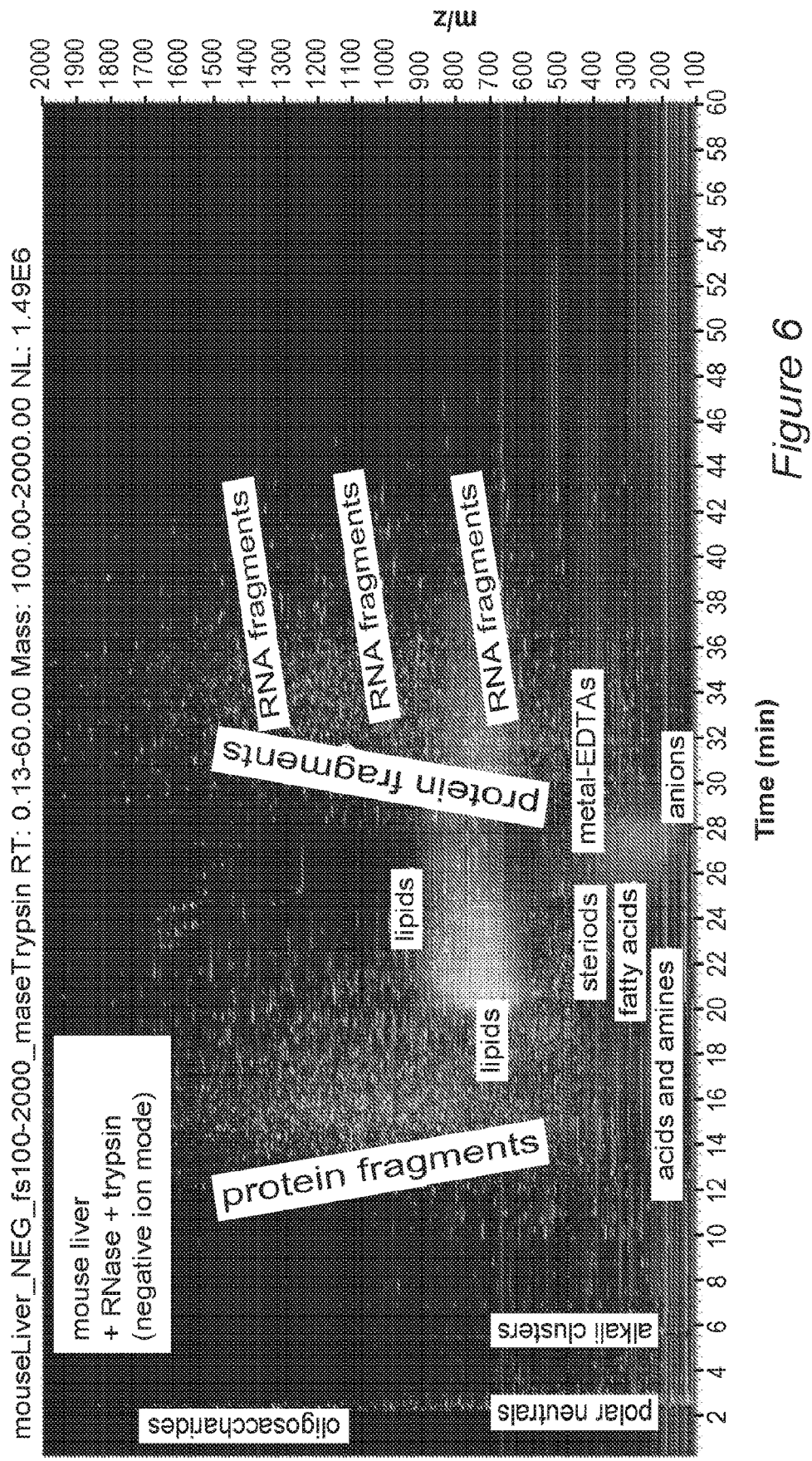
FIG. 6 shows the spectrum obtained from mouse liver homogenates that were digested with RNase A and trypsin and analyzed according to described procedures. Time and mass-to-charge are represented on the horizontal and vertical axes with increasing brightness of color representing higher ion intensity. Approximate positions of select analyte classes are labeled according to previous observations.

To demonstrate the feasibility simultaneous bottom-up macromolecular analysis of multiple biochemical classes, the pancreatic endolytic enzymes alpha-amylase, RNase A, and DNase I were used to digest serum albumin, glycogen, RNA, and DNA. Digestion across 18 hours yielded detectable products corresponding to oligosaccharides, oligonucleotides, and oligodeoxynucleotides even in the presence of trypsin and methanol. To test this approach in a biological matrix, mouse liver homogenate was digested with RNase A and trypsin, permitting the detection of metabolites, oligosaccharides, oligonucleotides, and tryptic peptides (FIGS. 5 and 6). Even without enzymes, lower molecular weight components are clearly separated, identifiable and quantifiable (FIG. 4). Similar results are obtained with cultured human liver cancer cells (FIG. 7), human plasma (FIG. 8), bovine adipose tissue (FIG. 9) and human urine (FIG. 10).

Each of the components and steps of the method are described in further detail below. In one embodiment, a method is provided for carrying out the analysis. In one embodiment, an apparatus or device is provided that comprises all the requisite instrumentation and reagents for carrying out the analysis. In one embodiment, a fluidic or microfluidic path is provided for processing the input sample in preparation for analysis by LC-MS. In one embodiment, individual samples can be loaded into a cassette or similar device for automated processing of a number of samples sequentially or in any order programmed into the device or apparatus. In one embodiment the apparatus or device can be programmed to provide data on the presence, identities or quantities of the analytes present in the sample. In one embodiment, the apparatus or device can be programmed to provide a diagnosis of a disease or a wellness profile, based on the presence or absence or relative quantities of various analytes in the sample. In one embodiment the output from the devices guides the therapeutic intervention or prophylaxis of a condition or disease, and then monitoring of the progression of the condition or disease and the effectiveness or lack thereof of the therapeutic intervention. In one embodiment the apparatus or device can be programmed to classify samples based on a pre-defined set of parameters regarding individual or groups of analytes present in the sample. In one embodiment, a data-base comprising results from samples from a large population of individuals with various conditions or diseases is created, for use in identifying health or disease in new samples. These embodiments are not intended in any way to be limiting on the utility of the invention, apparatuses and devices, methods, or systems utilizing the invention for its intended purposes.

Samples and Analytes Therein. In one embodiment, a method is provided for substantially simultaneously determining the presence, identities or levels of multiple analytes present in a single sample. Any sample from which a soluble extract can be prepared for analysis by LC-MS may be used. The sample may be, by way of non-limiting example, a biological sample, a water sample, an oil sample, a soil sample, a mineralogical sample, a polluted water sample, a produce sample, a meat sample, etc. The sample may be a solid, liquid, or a combination thereof. The sample may be a gas sample wherein the components are dissolved in an aqueous medium. Non-limiting examples of biological samples include samples from humans or other animals, or plants. Non-limiting examples of samples from animals include whole blood, plasma, serum, urine, feces, cerebrospinal fluid, saliva, sweat, saliva, semen, a biopsy specimen, cells or a tissue sample. Other samples may be hair, nails, shed skin, dandruff, and the like. Samples may be an aqueous solution, an aqueous suspension or aqueous tissue. Samples may be homogenized from solid or semi-solid samples. Other biological samples include biofilms, food and beverage preparations and derivatives. Non-biological samples may include industrial materials such as but not limited to raw materials, in-process samples, process intermediates and manufacturing batches. In one embodiment, the method is used to determine the presence of biological components in non-biological materials, such as in rock and mineral samples, fossils including fossilized humans and other animals, and rock samples from or on extraterrestrial sources or locations.

The sample may contain multiple analytes. In one embodiment the analytes are chemically related. In one embodiment the analytes are not chemically related. In one embodiment the analytes are biopolymers, such as any biomolecule comprised or repeating units of similar subunits, such as polysaccharides, nucleic acids and proteins. Other analytes are small molecule compounds such as metabolites, electrolytes, sugars, amino acids, metals, drugs, etc. Other biological components include polar and nonpolar lipids, volatile compounds, other exogenous chemicals, and the like. While the foregoing and other descriptions herein mainly describe analytes from biological sources and in particular from the human body, any veterinary or livestock derived analytes as well as non-living whole organisms are included as well, such as water pollutants, industrial chemicals and industrial products. Sources from plants are embodied herein.

In one embodiment, the sample is homogenized prior to Step 1 or during Step 1. The sample may be homogenized in an aqueous solution such as water or an aqueous buffer.

Step 1: Denaturation. The sample is treated with a denaturation reagent that denatures biopolymers in the sample thereby forming a denatured sample, wherein the denaturation reagent does not denature components of a normalization reagent when added thereto.

In one embodiment, the denaturation reagent comprises one or more solvents, one or more chaotropic agents, or one or more reference standards, or any combination thereof. In one embodiment, the solvent is methanol, ethanol, acetonitrile, or another volatile organic solvent or any combination thereof. In one embodiment, the solvent is methanol. In one embodiment, the aqueous sample is homogenized in about an equal amount of methanol. In on embodiment, the denaturation reagent further comprises a metal-chelation agent. In one embodiment, the metal-chelating agent is EDTA, EGTA or DMSA. In one embodiment, the metal-chelating agent is EDTA. In one embodiment the metal-chelating agent is present in the sample, such as when EDTA is used as anticoagulant for a blood sample.

In one embodiment, denaturation of the sample as described above is performed together with normalization, as described in the next step. In one embodiment, the components of the sample after denaturation are compatible with the normalization step in that the enzymes and other components of the normalization step are capable of carrying out their desired functions in the presence of any components from the denaturation step. In one embodiment, the denaturation step results in a solution with about 40-60% methanol content.

Step 2: Normalization. The denatured sample is treated with the normalization reagent, wherein the normalization agent converts the multiple analytes in the denatured sample into normalized analyte species and normalized analyte fragment species. In one embodiment, the species so formed are capable of being separated by multiple modes of chromatography and individually identified by mass spectrometry, thereby forming a normalized sample.

In one embodiment, the normalization reagent comprises one or more enzymes that depolymerize biopolymers in the sample into analyte fragment species. In one embodiment, the normalization reagent comprises pancreatic endolytic enzymes. In one embodiment, the normalization reagent comprises one or more proteinases, one or more nucleases, one or more glycosidases, one or more lipases, one or more chelating agents, one or more buffering agents, one or more reducing agents, one or more derivatizing agents, or any combination thereof.

In embodiment the proteinase is trypsin, chymotrypsin, proteinase K, LysC, LysN, AspN, GluC or ArgC. In one embodiment the proteinase is trypsin.

In one embodiment, the derivatizing agent is β-mercaptoethanol, dithiothreitol, tris (2-carboxyethyl) phosphine-HCl, or iodoacetamide. In one embodiment the derivatizing agent is iodoacetamide.

In one embodiment the buffering agent is phosphate, citrate, bicarbonate, sulfonate, formate, acetate or ammonia. In one embodiment, the pH of the sample during normalization is provided to maximally allow normalization of the sample. In one embodiment the pH is about 7.8.

In one embodiment, the normalization reagent comprises a combination of trypsin, ribonuclease A, EDTA, ammonium bicarbonate, and amylase.

In one embodiment a normalization reagent comprises 50 mM ammonium bicarbonate, 5 mM EDTA, and 1:20 m/m trypsin:sample protein.

In one embodiment, normalization comprises successive steps wherein certain of the reagents are not compatible, such as when the pH optima of different enzymes are different, such that the conditions during the normalization process are changed to maximally normalize the sample. In one embodiment when the normalization reagent comprises DNase I, EDTA is not concurrently present.

In one embodiment, the proteinase is added to the denatured sample concurrently or after incubation of the denatured sample with the other components of the normalization reagent.

In one embodiment, treating with the normalization agent comprises incubation for between about 0 and 24 hours at a temperature of about 37° C.

These guidelines for the desired outcome of the normalization step, to hydrolyze biopolymers into fragments capable of being analyzed by LC-MS where the biopolymer may be difficult to analyze without hydrolysis, and derivatizing any components to likewise be analyzable by LC-MS, are not meant to be limiting.

Step 3: Extraction. The normalized sample is treated with an extraction reagent and the soluble analyte species and analyte fragment species therein are retained, thereby forming an extracted sample.

Addition of organic solvents is a commonly used procedure in the metabolomics methods to substantially simultaneously deproteinize samples and extract their metabolites. A mixed polarity solvent combination is utilized to provide sample clean-up while extracting both polar and nonpolar molecules. Though samples can optionally be concentrated, injection of this relatively crude preparation allows for the detection of volatile analytes such as isopropanol or ethanol.

As noted herein, the components of the analytes in the sample capable of being analyzed by LC-MS are those that are made soluble by the denaturation and normalization steps. These soluble components are extracted then analyzed by LC-MS. In one embodiment, the extraction reagent is added at 1:1 (v/v) to the normalized sample. In one embodiment, the extraction reagent comprises acetonitrile and acetone. In one embodiment, the acetonitrile and acetone are present at 1:1 (v/v).

In one embodiment, the sample after the extraction step comprises soluble components and fragments of the analytes in the original sample. In one embodiment, separating the soluble components in the extracted sample is achieved by centrifugation or filtration.

The foregoing methods of denaturation, normalization and extraction are described as discrete steps, but in one embodiment may be conducted successively in a fluidic path wherein reagent addition, mixing, incubating, heating, separation, and other manipulations may be accomplished in any appropriate sequence in order to prepare the sample for LC-MS. In one embodiment wherein a fluid path is employed, the sample is introduced, denaturation reagent added to the fluid and the combined solutions mixed in a mixing chamber or turbulent flow region; the diameter, length and rate of flow provided to optimize the desired results of denaturation. Normalization reagents are then added to the sample as it moves through the fluid path or are immobilized along the fluid path. For normalization reagents and conditions that are not simultaneously compatible, the sample may, for example, be treated with nucleases in the absence of EDTA, then subsequently diluted and treated with proteinases and glycosidases, among other components, in the presence of EDTA. The fluid path design including length, diameter, rate of flow, smooth or turbulent/mixing regions, will be designed to maximize the efficiency of the sample processing steps. After normalization, the extraction reagent is added to the fluid path, and the soluble components of the fluid separated from the insoluble components by in-line filtration, continuous or zonal centrifugation, or any other means to separate the soluble components for further processing. After processing, the extracted sample may enter into the LC-MS, or processed samples may be successively stored and then injected into the LC-MS when the next programmed sample is ready to be analyzed. The foregoing conditions are merely exemplary of the form of a single fluid path means for sample processing and are not in any way intended to be limiting.

In some embodiments, the fluidic processing is gravity dependent. In some embodiments the fluidic processing pathway is gravity independent, for example in space environments and exploration.

Step 4 LC-MS. Subjecting the extracted sample to multiple modes of chromatography followed by mass spectrometry, whereby MS data for each normalized analyte species and normalized analyte fragment species present therein are generated.

In one embodiment, electrospray ionization is used. In other embodiments ambient pressure chemical ionization (APCI), ambient pressure photo-ionization (APPI) or electrospray ionization (ESI) are used. These are examples of ambient pressure ionization (API) methods that may be employed but are not intended to be limiting.

The use of chemical additives to improve LC-MS response of poorly detected analytes is well-established. Volatile salts such as ammonium acetate are used to elute ion exchange phases and to improve ionization of neutral compounds such as lipids. Metal-coordinating agents have been used to improve chromatography and sensitivity of phosphorylated compounds and metal ions using medronic acid and EDTA. A combination of such strategies is used herein to elute analytes from a commercially available tri-modal mixed mode column featuring reverse phase, cation- and anion-exchange properties. Using aqueous starting conditions, this column appears to retain most compounds with the exception of polar neutral molecules such as oligosaccharides and sugars.

Multiple modes of chromatography enables the chromatographic separation of diverse chemical species, whereas chromatography featuring single-modes of chromatography fail to separate analytes which do not participate in chemical interactions with the stationary phase. Multiple modes of separation are commonly used to resolve complex mixtures of analytes in various formats, including in offline fractionation, or online single-dimensional mixed-bed/phase columns, or in online in serial multi-dimensional LC. Here we describe a commercially available tri-modal column, however increasing the number of modes may improve the separation of based on other chemical properties including ion mobility, chirality, size, and non-ionic polarity.

In one embodiment, the multiple modes of chromatography comprises a reverse phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, or any combination thereof.

In one embodiment, a mobile phase used in the chromatography further comprises one or more ionizing adductant, such as but not limited to ammonium, protons, sodium, acetate, formate, propionate, phosphate, medronate, urea, biuret, triuret, or any combination thereof.

In one embodiment, the mass spectrometry data acquisition comprises high resolution full scans with low or high resolution MS2 data-independent or data-dependent acquisition with dynamic exclusion in both positive and negative ion modes.

Step 5: Analysis. Computationally determining from the MS data the presence, identities or levels of the multiple analytes present in the extracted sample.

In some embodiments, the LC-MS data comprises chromatographic retention time, ion mobility collisional cross section, precursor and product ion mass-to-charge ratios for different forms, states and ratios of ion adducts, losses, multimers, isotope abundance, charge states, or any combination thereof.

In one embodiment, computationally determining from the MS data the presence, identities or levels of the multiple analytes present in the extracted sample comprises comparing the MS data of the normalized analyte species or normalized analyte fragment species to the MS data of those species generated from known amounts of known analytes.

In one embodiment, computationally determining from the MS data the presence, identities or levels of the multiple analytes present in the extracted sample comprises comparing the MS data of the normalized analyte species or normalized analyte fragment species to the MS data generated from known amounts of the isotopologues of those species.

In one embodiment, computationally determining from the MS data the presence, identities or levels of the multiple analytes present in the extracted sample comprises comparing the MS data of the normalized analyte species or normalized analyte fragment species to the computationally simulated MS data of known or theoretical analytes.

In one embodiment, the computationally simulation of MS data for biopolymer fragments comprises generating all possible or considered combinations and permutations of subunits for the biopolymer fragments and calculating the expected MS data based on the subunit chemical composition of the theoretical biopolymer fragments.

In one embodiment, computationally determining from the MS data the identities of the multiple analytes present in the extracted sample comprises pre-identifying the biochemical class of the normalized analyte species or normalized analyte fragment species by comparing the isotope distribution of the precursor ion to the computationally simulated isotope distributions of known biochemical classes, and subsequently comparing the MS data of the normalized analyte species or normalized analyte fragment species to that MS data of known or theoretical analytes from the matched biochemical class.

In one embodiment, computationally determining from the MS data the presence or levels of the multiple analytes present in the extracted sample comprises adjusting the intensity peak area of the normalized analyte species or normalized analyte fragment species in proportion to the intensity peak areas of known amounts of known analytes that were added to the sample or were already present in the sample.

In one embodiment, computationally determining from the MS data identities of the multiple analytes present in the extracted sample comprises matching the normalized analyte species or normalized analyte fragment species based on the chromatographic retention time, expected isotopic masses, or relative abundances of their precursor ions, their fragment ions, their alternate charge-state ions, their alternate positively- or negatively-charged ions, or chemically-related ions such as derivatives or analogues to such characteristics of or from those recorded or simulated for known analytes.

In some embodiments, software, algorithms and other methods for identifying species in the MS data and identifying therefrom the identity of analytes is achieved by use of the KNIME (v3.6.2) OpenMS (v2.4.0) plugin, Thermo Proteome Discoverer (v2.2.0) and Thermo Compound Discoverer (v2.0.0), but these are merely exemplary and not intended to be limiting.

In one example of the method, the following steps may be carried out.

Step 1. Treating the sample with an equal volume of denaturation reagent comprising methanol, wherein the denaturation agent denatures biopolymers in the sample thereby forming a denatured sample, wherein the denaturation reagent does not denature components of a normalization reagent when added thereto;

Step 2. Treat the denatured sample with the normalization reagent comprising 50 mM ammonium bicarbonate, 5 mM EDTA, 1:20 m/m trypsin:sample protein, pH 7.8, for 4 hours at 37° C., wherein the normalization agent converts the multiple analytes in the denatured sample into normalized analyte species and normalized analyte fragment species, the species capable of being separated by multiple modes of chromatography and individually identified by mass spectrometry, thereby forming a normalized sample;

Step 3. Treat the normalized sample with an equal volume of extraction reagent comprising acetonitrile:acetone 1:1, centrifuging the sample and retaining the supernatant comprising soluble analyte species and analyte fragment species therein, thereby forming an extracted sample;

Step 4. Subject the extracted sample to multiple modes of chromatography followed by mass spectrometry, whereby MS data for each normalized analyte species and normalized analyte fragment species present therein are generated; and Step 5. Computationally determine from the MS data the presence, or levels, and/or identities of the multiple analytes present in the extracted sample.

The foregoing methods, apparatus, device or system may be used for a variety of purposes. In one embodiment, a method for determining a condition of a living source, from which a biological sample is derived, comprising:
  a. substantially simultaneously determining the presence, identities or levels of multiple analytes present in the biological sample in accordance with the methods described herein;
  b. comparing the presence, identities or levels of the analytes therein to those of a biological sample from a living source sample without said condition, wherein the condition is identifiable from a change in the presence, identities or levels of multiple analytes; and
  c. determining the condition of said living source.

In one embodiment, the condition is a pathological condition or disease, and the result of the determining are used for guiding therapeutic intervention or monitoring of the effectiveness of the treatment or progression of the disease or condition. In one embodiment, the condition is a dietary or metabolic imbalance and the results of the determining are used for guiding change in diet or lifestyle, and monitoring the effect and progression of the change. In one embodiment the method can used to determine molecules or a pattern of molecules associated with protection from, or risk of developing, a condition such as a pathological condition. In one non-limiting example, risk for developing type II diabetes (T2D) may be assessed and new biomarkers may be discovered by comparing the analytes or pattern or analytes in samples from subjects with T2D versus healthy individuals' samples, such that the T2D samples have high or low levels of one or more compounds or biomarkers which are not currently associated with increased diabetes risk, and the healthy samples have low or high levels of such compounds or biomarkers which is not currently indicated for protection against diabetes.

In another embodiment of the invention, the method described herein is carried out by an apparatus or device capable of carrying out all of the methods steps. In one embodiment, the apparatus comprises
  a. means for denaturing biopolymers in the sample thereby forming a denatured sample, wherein the denaturation reagent does not denature components of a normalization reagent when added thereto;
  b. means for normalizing the sample wherein multiple analytes in the denatured sample are converted into normalized analyte species and normalized analyte fragment species, the species capable of being separated by multiple modes of chromatography and individually identified by mass spectrometry;
  c. means for extracting the normalized sample and retaining the soluble analyte species and analyte fragment species therein;
  d. means for subjecting the extracted sample to multiple modes of chromatography followed by mass spectrometry, whereby MS data for each normalized analyte species and normalized analyte fragment species present therein are generated; and
  e. means for computationally determining from the MS data the presence, identities or levels of the multiple analytes present in the extracted sample.

In one embodiment, a system is provided that carries out the methods described herein above. In one embodiment, a system is provided for substantially simultaneously determining the presence, identities or levels of multiple, chemically-related and chemically-unrelated analytes present in a single sample, the system comprising:
  a. a denaturation reagent that denatures biopolymers in the sample thereby forming a denatured sample, wherein the denaturation reagent does not denature components of a normalization reagent when added thereto;
  b. a normalization reagent that converts the multiple analytes in the sample into normalized analyte species or normalized analyte fragment species capable of being separated by mixed mode liquid chromatography and individually identified by tandem mass spectrometry;
  c. an extraction reagent that extracts the soluble analyte species and analyte fragment species;
  d. a separation process for retaining the soluble analyte species and analyte fragment species therein, thereby forming an extracted sample;
  e. multiple modes of chromatography that resolves soluble analyte species and analyte fragment species;
  f. mass spectrometry that generates data on the individual species; and
  g. one or more algorithms for computationally determining from the data of each normalized analyte species and normalized analyte fragment species the presence, identities or levels of the multiple analytes present in the sample.

Some embodiments provide a method for identifying a plurality of analytes of different types from a sample, comprising: (a) subjecting said sample containing or suspected of containing said plurality of analytes of different types to conditions sufficient to yield a solution comprising said plurality of analytes or derivatives thereof; and (b) using an instrument to process said solution to identify said plurality of analytes or derivatives thereof, thereby identifying said plurality of analytes, wherein said plurality of analytes or derivatives thereof is identified in a single run of said instrument. In some embodiments, (b) is performed in a single instrumental run. One of ordinary skill in the art will understand that the term "a single instrumental run," as used herein, generally refers to one single analytical process performed on one single loading of one single sample with one single instrument. One of ordinary skill in the art will understand that a "derivative" of an analyte can be a fragmented, ionized, oxidized, reduced, chemically functionalized, chemical functionality removed, isomerized, coordinated, polymerized, or multimerized form, or a combination thereof, of the analyte. In some embodiments, said plurality of analytes comprises at least three types of analytes selected from the group consisting of protein, nucleic acid, small molecule, lipid, carbohydrate, electrolyte, and metal. One of ordinary skill in the art will understand that non-limiting examples of an "electrolyte" include Na+, Cl−, K+, bicarbonate, phosphate, sulfate, bromide, acetate, formate, and ammonium. One of ordinary skill in the art will also understand that non-limiting examples of small molecules include a molecule with a molecular weight less than 900 Daltons, less than 1500 Daltons, or less than 2000 Daltons. In some embodiments, said plurality of analytes comprises: at least one type of analyte selected from small molecule, lipid, and carbohydrate; and at least two types of analytes selected from protein, nucleic acid, electrolyte, and metal. In some embodiments, said plurality of analytes comprises: at least one type of analyte selected from protein, and nucleic acid; and at least two types of analytes selected from small molecule, lipid, and carbohydrate. In some embodiments, said plurality of analytes comprises small molecule, lipid, and protein. In some embodiments, said plurality of analytes comprises small molecule, lipid, carbohydrate, and protein. In some embodiments, said plurality of analytes comprises small molecule, lipid, carbohydrate, and electrolyte. In some embodiments, said plurality of analytes comprises small molecule, lipid, carbohydrate, electrolyte, and metal. In some embodiments, said plurality of analytes further comprises one or both of protein and nucleic acid. In some embodiments, said small molecule is an endogenous small molecule, an exogenous small molecule, or a combination thereof. In some embodiments, said plurality of analytes comprises an exogenous chemical. In some embodiments, at least one of said plurality of analytes is a volatile compound. In some embodiments, said plurality of analytes or derivatives thereof of said solution has a distribution of molecular size or mass that is different than said plurality of analytes contained or suspected of being contained in said sample. In some embodiments, said plurality of analytes or derivatives thereof of said solution comprises an amount of charged molecules, an amount of hydrophilic molecules, an amount of molecules with hydrophobic functionality, or any combination thereof that is different than said plurality of analytes contained or suspected of being contained in said sample. In some embodiments, said charged molecules comprise negatively charged molecules, positively charged molecules, or both. In some embodiments, said plurality of analytes or derivatives thereof of said solution has a distribution of pKa constant values of molecules for acidic and basic functional groups that is different than said plurality of analytes contained or suspected of being contained in said sample. In some embodiments, said plurality of analytes or derivatives thereof of said solution has a distribution of octanol-water partition coefficients of molecules that is different than said plurality of analytes contained or suspected of being contained in said sample. In some embodiments, said plurality of analytes or derivatives thereof of said solution has a greater percentage by mass of molecules that fall within a pre-determined range than said plurality of analytes contained or suspected of being contained in said sample. In some embodiments, said plurality of analytes or derivatives thereof of said solution has a distribution of molecular size or mass that is narrower than said plurality of analytes contained or suspected of being contained in said sample. In some embodiments, said plurality of analytes or derivatives thereof of said solution has a greater percentage by mass of charged molecules than said plurality of analytes contained or suspected of being contained in said sample. In some embodiments, said plurality of analytes or derivatives thereof of said solution has a greater percentage by mass of hydrophilic molecules as measured by octanol-water partition coefficient than said plurality of analytes contained or suspected of being contained in said sample. In some embodiments, said plurality of analytes or derivatives thereof of said solution has a distribution of mass-to-charge ratio (m/z) that is narrower than said plurality of analytes contained or suspected of being contained in said sample such that said plurality of analytes or derivatives thereof of said solution has a greater percentage by mass of molecules that fall within a range detectable by mass spectrometry than said plurality of analytes contained or suspected of being contained in said sample. In some embodiments, said range detectable by mass spectrometry is between 100 Dalton per electron charge (Da/e) to 2,000 Da/e. In some embodiments, said plurality of analytes or derivatives thereof of said solution each have a mass-to-charge ratio (m/z) between 15 Dalton per electron charge (Da/e) to 4,000 Da/e.

In some embodiments of the method for identifying the plurality of analytes of different types from the sample as described hereinabove or anywhere else herein, (a) comprises one or any combination of the following to obtain a treated sample: (i) homogenizing said sample; (ii) contacting said sample with a denaturation agent, thereby changing the conformation of at least one of said plurality of analytes; (iii) contacting said sample with a chelating agent, thereby forming a chelate complex with at least one of said plurality of analytes; (iv) contacting said sample with a derivatizing agent, thereby forming a derivative of at least one of said plurality of analytes; (v) contacting said sample with a reducing agent, thereby modifying at least one of said plurality of analytes; and (vi) contacting said sample with an enzyme, thereby producing fragments of at least one of said plurality of analytes. In some embodiments, (iii) is performed one or more times. In some embodiments, (vi) is performed one or more times. In some embodiments, (i) is performed prior to or substantially simultaneously with (ii). In some embodiments, (ii) is performed substantially simultaneously with (iii). In some embodiments, (ii) is performed prior to or substantially simultaneously with (vi). In some embodiments, (vi) is performed substantially simultaneously with one or more of (iii), (iv), and (v). In some embodiments, (vi) is performed substantially simultaneously with (iv). In some embodiments, (vi) is performed substantially simultaneously with (iii) and (iv). In some embodiments, (iii) is performed at least twice, once substantially simultaneously with (i), and again substantially simultaneously with (vi). In some embodiments, (vi) is performed at least twice, once substantially simultaneously with (ii), and again substantially simultaneously with (iv). In some embodiments, said enzyme used in (vi), performed substantially simultaneously with (ii), is protease. One of ordinary skill will understand that the term "substantially simultaneously," as used herein, generally refers to performing each of the relevant steps within temporal proximity (i.e. within 1 hr, within 30 min, within 10 min, within 5 min, or within 1 min) to one another no longer than what is required to effect the purpose of the relevant method. In some embodiments, (i) is carried out in a mixture of water and methanol at a ratio between 1:5 and 5:1 by volume. In some embodiments, (i) is carried out in a mixture of water and methanol at a ratio between 1:2 and 2:1 by volume. In some embodiments, said mixture is a 1:1 by volume mixture of water and methanol. In some embodiments, said denaturation agent comprises a solvent, a chaotropic agent, and a reference standard. In some embodiments, said solvent is selected from methanol, ethanol, and acetonitrile. In some embodiments, said solvent is methanol. In some embodiments, said chelating agent is selected, independently on each occurrence of (iii), from ethylenediaminetetraacetic acid (EDTA), ethylene glycol-bis(β-aminoethyl ether)-N,N,N',N'-tetraacetic acid (EGTA), and dimercaptosuccinic acid (DMSA). In some embodiments, said chelating agent is EDTA. In some embodiments, said derivatizing agent is a peptide-alkylating agent. In some embodiments, said derivatizing agent is iodoacetamide. In some embodiments, said enzyme comprises one or any combination selected, independently on each occurrence of (vi), from the group consisting of nuclease, protease, glycosidase, and lipase. In some embodiments, said glycosidase is amylase. In some embodiments, said protease is trypsin. In some embodiments, said nuclease comprises one or both of DNase I and ribonuclease A. In some embodiments, DNase I and EDTA are not concurrently present in (vi). In some embodiments, (vi) is carried out in an ammonium bicarbonate buffer. In some embodiments, (vi) comprises incubating at about 37° C. for about 24 hours or less. In some embodiments, (a) further comprises extracting said plurality of analytes or derivatives thereof from said treated sample with an extraction reagent, thereby obtaining said solution. In some embodiments, said extracting comprises adding said extraction reagent at 1:1 by volume to said treated sample. In some embodiments, said extraction reagent comprises acetonitrile and acetone at 1:1 by volume. In some embodiments, (a) further comprises removing insoluble impurity from said solution by centrifugation or filtration.

In some embodiments of the method for identifying the plurality of analytes of different types from the sample as described hereinabove or anywhere else herein, (b) comprises subjecting said plurality of analytes or derivatives thereof to an electron beam, thereby generating at least one ionized form or fragment of at least one of said plurality of analytes or derivatives thereof. In some embodiments, (b) further comprises contacting said plurality of analytes or derivatives thereof with a mixed mode chromatography matrix, comprising at least three orthogonal chromatographic modes, wherein each of said at least three orthogonal chromatographic modes is configured to separate a given type of said plurality of analytes or derivatives thereof from said solution. In some embodiments, at least one of said orthogonal chromatographic mode separates from said solution at least one derivative of said analyte. In some embodiments, said mixed mode chromatography matrix comprises at least three properties selected from the group consisting of cation exchange properties, anion exchange properties, ion exclusion properties, ligand exchange properties, size exclusion properties, chiral properties, reverse-phase properties, affinity properties, hydrophilic properties, polydentate properties, or any combination thereof. One of ordinary skill in the art will understand that "cation exchange" may include strong cation-exchange (SCX) and weak cation-exchange (WCX). One of ordinary skill in the art will also understand that "anion exchange" may include strong anion-exchange (SAX) and weak anion-exchange (WAX). In some embodiments, (b) further comprises eluting said plurality of analytes and derivatives thereof with at least three mobile phases. In some embodiments, a first fraction of said plurality of analytes and derivatives thereof is eluted by a first mobile phase, wherein said first mobile phase comprises water and 0.1% formic acid (v/v); a second fraction of said plurality of analytes and derivatives thereof is eluted by a second mobile phase, wherein said second mobile phase comprises acetonitrile and 0.1% formic acid (v/v); and a third fraction of said plurality of analytes and derivatives thereof is eluted by a third mobile phase, wherein said third mobile phase comprises 1:1 (v/v) methanol/water, 200 mM ammonium acetate, and formic acid. In some embodiments, at least one of said at least three mobile phases, or at least one of said first mobile phase, said second mobile phase, and said third mobile phase comprises one or more ionizing adductants selected from the group consisting of ammonium, protons, sodium, acetate, formate, propionate, phosphate, medronate, urea, biuret, and triuret. In some embodiments, (b) comprises determining a mass of each of said plurality of analytes or derivatives thereof by mass spectrometry. In some embodiments, (b) comprises determining an amount of each of said plurality of analytes or derivatives thereof by mass spectrometry. One of ordinary skill in the art will understand that said mass or amount of each of said plurality of analytes or derivatives can be discerned from the LC-MS data, comprising chromatographic retention time, ion mobility collisional cross section, precursor and product ion mass-to-charge ratios for different forms, states and ratios of ion adducts, losses, multimers, isotope abundance, charge states, or any combination thereof. In some embodiments, said mass spectrometry is low or high resolution full or fragmentation scan mass spectrometry generated by data-independent or data-dependent acquisition with or without dynamic exclusion in both positive and negative ion modes. In some embodiments, said determining said mass or said amount comprises comparing said low or high resolution mass spectrometric characteristics to one or more reference mass full or spectra. In some embodiments, said solution is an aqueous solution, optionally comprising a water-miscible organic solvent. In some embodiments, said sample is a biological sample.

Some embodiments provide a method for determining a disease or condition in a subject, comprising: (i) identifying a plurality of analytes, individually or collectively, known to be associated with said disease or condition from a single sample of said subject to obtain an identified amount for each of said plurality of analytes, wherein said plurality of analytes comprises analytes of different types; (ii) determining a difference between a reference amount and said identified amount for said each of said plurality of analytes to obtain a plurality of difference values; and (iii) using a trained machine learning algorithm to determine said disease or condition based on said plurality of difference values. One of skill in the art will understand that the term "reference amount," as used herein, generally refers to an amount which allows determining whether a subject has the disease or condition. In some embodiments of the method for determining the disease or condition in the subject as described hereinabove or anywhere else herein, (i) may comprise: (a) subjecting said single sample containing or suspected of containing said plurality of analytes to conditions sufficient to yield a solution comprising said plurality of analytes or derivatives thereof; and (b) using said solution to identify said plurality of analytes or derivatives thereof, thereby identifying said plurality of analytes. In some embodiments of the method for determining the disease or condition in the subject as described hereinabove or anywhere else herein, (b) may be performed in a single instrumental run. The trained algorithm may be trained using a plurality of training samples comprising, or comprising about (i.e., ±1, ±2, or ±3), 30, 40, 50, 60, 70, 80, 90, 100, 110, 120, 130, 140, 150, 160, or 170 training samples, or a range between any two foregoing values. The trained algorithm may be trained using a plurality of training samples comprising no more than, or no more than about (i.e., ±1, ±2, or ±3), 30, 40, 50, 60, 70, 80, 90, 100, 110, 120, 130, 140, 150, 160, or 170 training samples. The trained algorithm may be trained using a plurality of training samples comprising no more than 170 training samples. The trained algorithm may be trained using a plurality of training samples comprising no more than 30 training samples. The trained algorithm may be trained using a plurality of training samples comprising at least, or at least about (i.e., ±1, ±2, or ±3), 30, 40, 50, 60, 70, 80, 90, 100, 110, 120, 130, 140, 150, 160, or 170 training samples. The trained algorithm may be trained using a plurality of training samples comprising at least 30 training samples. The trained algorithm may be trained using a plurality of training samples comprising at least 170 training samples. The method may further comprise, prior to (i), identifying said plurality of analytes from each of said plurality of training samples. The disease or condition may be determined at an accuracy of, or of about (i.e., ±0.01, ±0.02, or ±0.03), 0.5, 0.55, 0.6, 0.65, 0.7, 0.75, or 0.8, or a range between any two of the foregoing values. The disease or condition may be determined at an accuracy of at least, or of at least about (i.e., ±1%, ±2%, ±3%, ±4%, or ±5%), 50%, 55%, 60%, 65%, 70%, 75%, 80%, 85%, 90%, 95%, 99%. The disease or condition may be determined at a specificity of at least, or of at least about (i.e., ±1%, ±2%, ±3%, ±4%, or ±5%), 50%, 55%, 60%, 65%, 70%, 75%, 80%, 85%, 90%, 95%, 99%. The disease or condition may be determined at a sensitivity of at least, or of at least about (i.e., ±1%, ±2%, ±3%, ±4%, or ±5%), 50%, 55%, 60%, 65%, 70%, 75%, 80%, 85%, 90%, 95%, 99%. The disease or condition may be determined at a precision of at least, or of at least about (i.e., ±1%, ±2%, ±3%, ±4%, or ±5%), 50%, 55%, 60%, 65%, 70%, 75%, 80%, 85%, 90%, 95%, 99%. The disease or condition may be selected from the group consisting of aging, cardiovascular disease, inflammation, heart failure, and dementia. The plurality of analytes may comprise one or more selected from the group consisting of apolipoprotein B (apoB), cortisol, C-reactive protein (CRP), and N-terminal pro b-type natriuretic peptide (NT-ProBNP), and derivatives thereof. The plurality of analytes may comprise two or more analytes selected from the group consisting of ribonucleotide, deoxyribonucleotide, polypeptide, and metabolite. The plurality of analytes may comprise three or more analytes selected from the group consisting of ribonucleotide, deoxyribonucleotide, polypeptide, and metabolite. The plurality of analytes may comprise all four analytes selected from the group consisting of ribonucleotide, deoxyribonucleotide, polypeptide, and metabolite. The plurality of analytes may comprise ribonucleotide, deoxyribonucleotide, and metabolite. The plurality of analytes may comprise polypeptide, and metabolite. The plurality of analytes may comprise at least three types of analytes selected from the group consisting of protein, nucleic acid, small molecule, lipid, carbohydrate, electrolyte, and metal. The plurality of analytes may comprise at least one type of analyte selected from small molecule, lipid, and carbohydrate; and at least two types of analytes selected from protein, nucleic acid, electrolyte, and metal. The plurality of analytes may comprise at least one type of analyte selected from protein, and nucleic acid; and at least two types of analytes selected from small molecule, lipid, and carbohydrate.

Computer Systems

Figure 17:
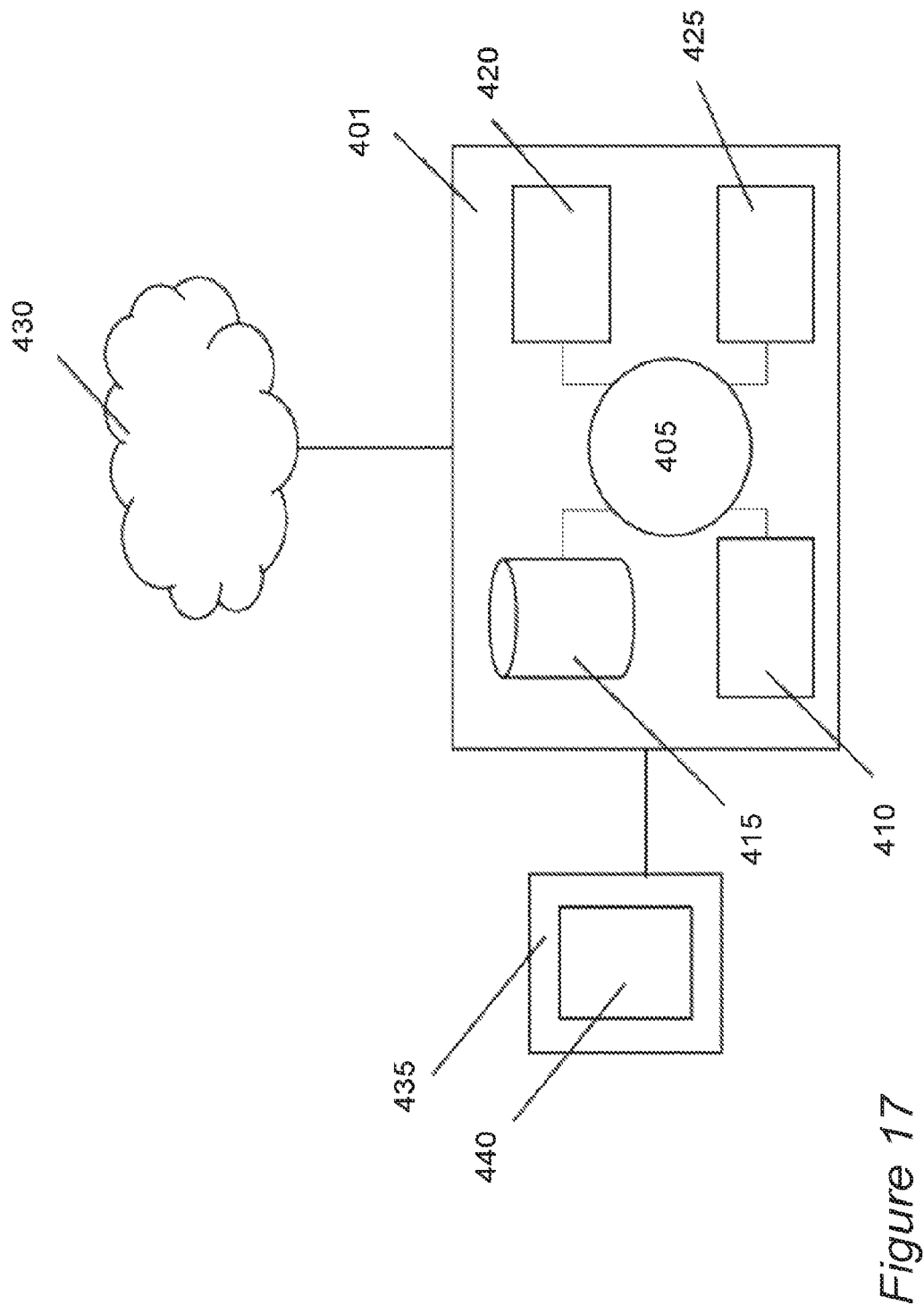
FIG. 17 shows a schematic view of a computer system, in accordance with some embodiments.

The present disclosure provides computer systems that are programmed or otherwise configured to implement methods disclosed herein. FIG. 17 shows a computer control system 401 that is programmed or otherwise configured to process data from a mass spectrometer. The computer control system 401 can regulate various aspects of the methods of the present disclosure, such as, for example, methods of analyzing vital sign data. The computer control system 401 can be implemented on an electronic device of a user or a computer system that is remotely located with respect to the electronic device. The electronic device can be a mobile electronic device.

The computer system 401 includes a central processing unit (CPU, also "processor" and "computer processor" herein) 405, which can be a single core or multi core processor, or a plurality of processors for parallel processing. The computer control system 401 also includes memory or memory location 410 (e.g., random-access memory, read-only memory, flash memory), electronic storage unit 415 (e.g., hard disk), communication interface 420 (e.g., network adapter) for communicating with one or more other systems, and peripheral devices 425, such as cache, other memory, data storage and/or electronic display adapters. The memory 410, storage unit 415, interface 420 and peripheral devices 425 are in communication with the CPU 405 through a communication bus (solid lines), such as a motherboard. The storage unit 415 can be a data storage unit (or data repository) for storing data. The computer control system 401 can be operatively coupled to a computer network ("network") 430 with the aid of the communication interface 420. The network 430 can be the Internet, an internet and/or extranet, or an intranet and/or extranet that is in communication with the Internet. The network 430 in some cases is a telecommunication and/or data network. The network 430 can include one or more computer servers, which can enable distributed computing, such as cloud computing. The network 430, in some cases with the aid of the computer system 401, can implement a peer-to-peer network, which may enable devices coupled to the computer system 401 to behave as a client or a server.

The CPU 405 can execute a sequence of machine-readable instructions, which can be embodied in a program or software. The instructions may be stored in a memory location, such as the memory 410. The instructions can be directed to the CPU 405, which can subsequently program or otherwise configure the CPU 405 to implement methods of the present disclosure. Examples of operations performed by the CPU 405 can include fetch, decode, execute, and writeback.

The CPU 405 can be part of a circuit, such as an integrated circuit. One or more other components of the system 401 can be included in the circuit. In some cases, the circuit is an application specific integrated circuit (ASIC).

The storage unit 415 can store files, such as drivers, libraries and saved programs. The storage unit 415 can store user data, e.g., user preferences and user programs. The computer system 401 in some cases can include one or more additional data storage units that are external to the computer system 401, such as located on a remote server that is in communication with the computer system 401 through an intranet or the Internet.

The computer system 401 can communicate with one or more remote computer systems through the network 430. For instance, the computer system 401 can communicate with a remote computer system of a user (e.g., a user controlling the smart wearable product). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 401 via the network 430.

Methods as described herein can be implemented by way of machine (e.g., computer processor) executable code stored on an electronic storage location of the computer system 401, such as, for example, on the memory 410 or electronic storage unit 415. The machine executable or machine readable code can be provided in the form of software. During use, the code can be executed by the processor 405. In some cases, the code can be retrieved from the storage unit 415 and stored on the memory 410 for ready access by the processor 405. In some situations, the electronic storage unit 415 can be precluded, and machine-executable instructions are stored on memory 410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" generally refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 401 can include or be in communication with an electronic display 435 that comprises a user interface (UI) 440 for providing, for example, parameters for producing the slurry and/or applying the slurry to a substrate. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 405. The algorithm can, for example, collect data from a smart wearable product and analyze the data for changes in the data over a defined period of time.

Examples

Materials and Methods
Sample Preparation

Chemical reference standards are prepared at 1 µM concentrations in the extraction solution and are analyzed by LC-MS to verify retention times and characteristic ion masses.

Approximately 100 mg of sample is homogenized in 20 µL aqueous additives and 100 µL methanol to bring the mixture to final concentrations of 50 mM ammonium bicarbonate, 5 mM EDTA, trypsin (1:20 m/m trypsin:protein), and about 10% dry sample mass. The sample digestion mixtures are incubated at 37° C. for 4 hours with rotation. Following digestion, the sample is treated with 100 µL acetonitrile and 100 µL acetone and is allowed to come to equilibrium at 4° C. for 15 minutes. The samples are centrifuged at 15000×g for 5 minutes and the supernatant is transferred to a new vial and stored at 4° C. until LC-MS analysis.

Liquid Chromatography

The analytes are separated using mixed mode chromatography featuring cation and anion exchange and reverse phase characteristics—a Dionex Trinity P1 2.1 mm×150 mm equipped with a precolumn filter and guard column. The solvent programming is composed of 2 linear gradients consisting of the following mobile phases: mobile phase A—95:5 water:acetonitrile with 0.1% formic acid and 5 mM ammonium acetate, mobile phase B—95:5 acetonitrile:water with 0.1% formic acid and 5 mM ammonium acetate, and mobile phase C—50:50 water:methanol with 200 mM formic acid and 200 mM ammonium acetate. Medronic acid at 5 µM is added to all mobile phases to improve the chromatography and detection of phosphorylated compounds. The linear gradient programming proceeds at 200 µL/min and 30° C. in the forward direction from 100% A to 100% B to 100% C and in the reverse direction at 0, 20, 40, 45, 50, and 60 minutes, respectively. Runs are extended by lengthening the forward portion of the gradient programming. Either a Dionex Ultimate 3000RS UHPLC or Thermo Surveyor HPLC autosampler and LC stacks are employed depending on the instrument used for analysis.

Mass Spectrometry Detection

The eluent is introduced to the MS by an electrospray ionization source, either a Thermo Q Exactive Plus or a Thermo LTQ Orbitrap XL. External calibration was carried out with standard positive and negative ESI calibration solutions prior to analysis. The mass spectrometer is set to acquire high resolution full scans with low or high resolution MS2 data-dependent acquisition with dynamic exclusion in both positive and negative ion modes using mass spectrometer parameters that are optimized to maximize sensitivity towards the MRFA peptide in both positive and negative ion modes.

Enzymatic Digestion

Enzyme and trypsin stock solutions are prepared at 10 mg/mL as designated by supplier instructions. Enzyme solution (10 µL) and trypsin solution (10 uL) is added to the substrate solution (100 µL) and incubated for 18 hours at 37° C. with rotation. Equivalent solutions without substrates or enzymes are substituted as negative controls where appropriate. Reactions are stopped by the addition of organic solvents (200 µL 1:1 acetonitrile:acetone).

Data Analysis

Qualitative data analysis was conducted using Thermo Qual browser which is used to quantify selected compounds selected based on their chemical diversity and perceived biomedical importance. Peak areas were measured over full scans and were normalized by added internal standards (to adjust for injection volume) and by constant contaminant ions (to adjust for ionization efficiency).

The raw LC-MS data was converted to mzML format using proteowizard for processing with OpenMS. MS/MS fragmentation spectra were matched to tryptic peptide sequences generated from Human, reversed decoy, and cRAP proteins using the !Tandem peptide mapping algorithm. The fragmentation spectra were also matched to metabolites using the Sirius adapter. Features were identified using the mass trace approach and were retained if detected in over 20% of samples. The features were exported to tab-delimited text for analysis in the R software environment. Intensities were log 10 transformed and the data was normalized for total amount, digestion and extraction efficiency and total amount injected and instrument sensitivity by linear adjustment for median intensity of peptides, lipids, and metabolites.

Using the aforementioned methods, selected analytes presented as detected in human plasma are shown in FIG. 2. Time and intensity peak area are represented on the horizontal and vertical axes respectively. The selected analytes are sodium, cholesterol, phenylalanine, creatinine, fructosamine (and isomer), triglyceride isomers (52:2), a tryptic albumin peptide, and bilirubin. FIG. 3 shows box plots of select analytes across 5 different plasma samples in 5 replicates. The name of each analyte is listed above each dot plot with the Kruskal-Wallis p-value denoting whether any of the differences between the sample medians are statistically significant. Sample number and log 10-scaled intensity peak area are represented on the horizontal and vertical axes, respectively. The dots represent the quintuplicate measurements of each sample and the horizontal lines represent the quartiles of all replicates.

FIG. 4 shows the spectrum obtained from mouse liver homogenates that were digested without enzymes and analyzed according to the described procedures. Time and mass-to-charge are represented on the horizontal and vertical axes with increasing brightness of color representing higher ion intensity. Approximate positions of select analyte classes are labeled according to previous observations.

FIG. 5 shows the spectrum obtained from mouse liver homogenates that were digested with RNase A and analyzed according to the described procedures. Time and mass-to-charge are represented on the horizontal and vertical axes with increasing brightness of color representing higher ion intensity. Approximate positions of select analyte classes are labeled according to previous observations.

FIG. 6 shows the spectrum obtained from mouse liver homogenates that were digested with RNase A and trypsin and analyzed according to described procedures. Time and mass-to-charge are represented on the horizontal and vertical axes with increasing brightness of color representing higher ion intensity. Approximate positions of select analyte classes are labeled according to previous observations.

Figure 7:
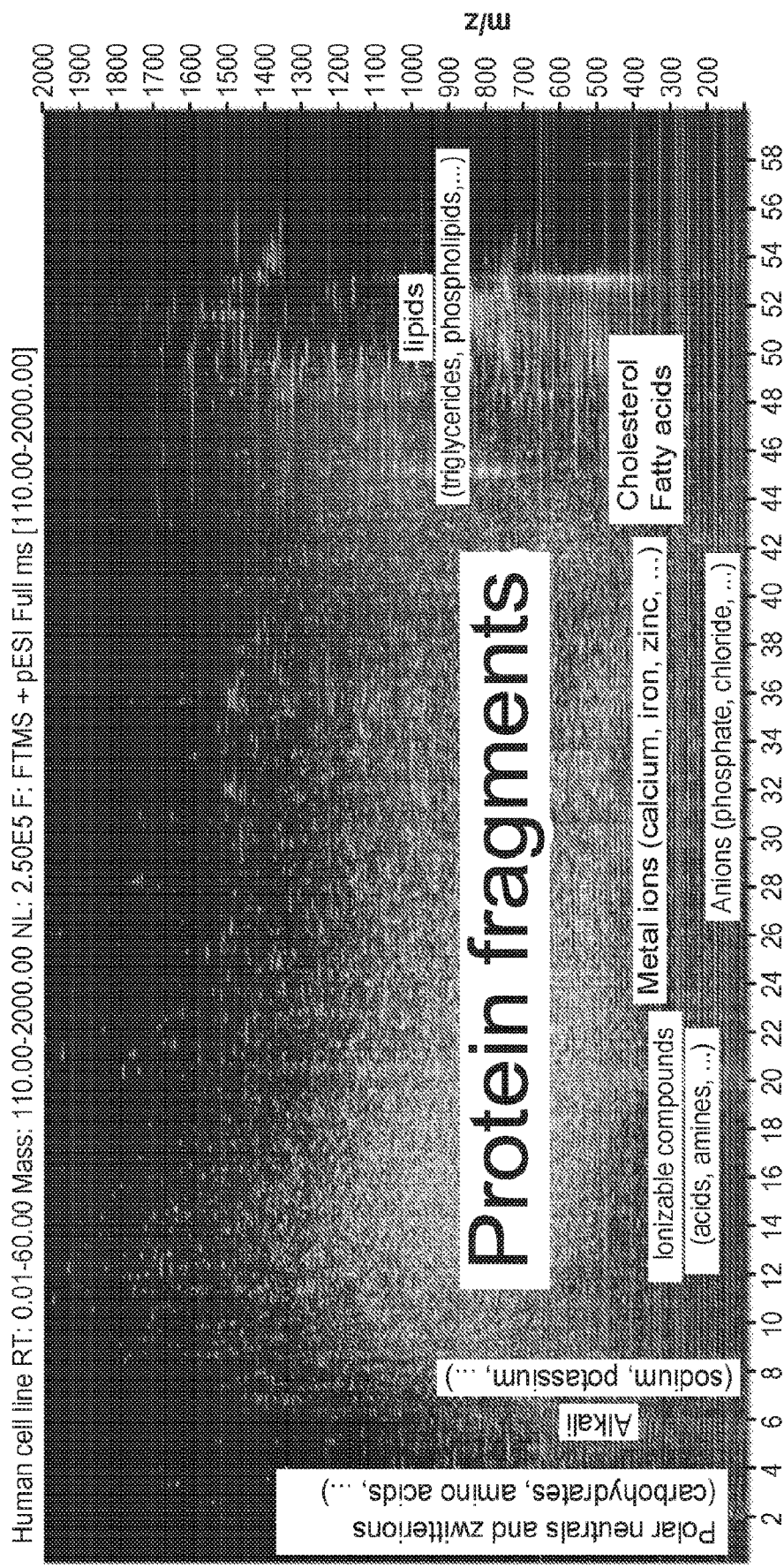
FIG. 7 shows the spectrum obtained from cultured human liver cancer cells that were digested with trypsin and analyzed according to the described procedures. Time and mass-to-charge are represented on the horizontal and vertical axes with increasing brightness of color representing higher ion intensity. Approximate positions of select analyte classes are labeled according to previous observations.

FIG. 7 shows the spectrum obtained from cultured human liver cancer cells that were digested with trypsin and analyzed according to the described procedures. Time and mass-to-charge are represented on the horizontal and vertical axes with increasing brightness of color representing higher ion intensity. Approximate positions of select analyte classes are labeled according to previous observations.

Figure 8:
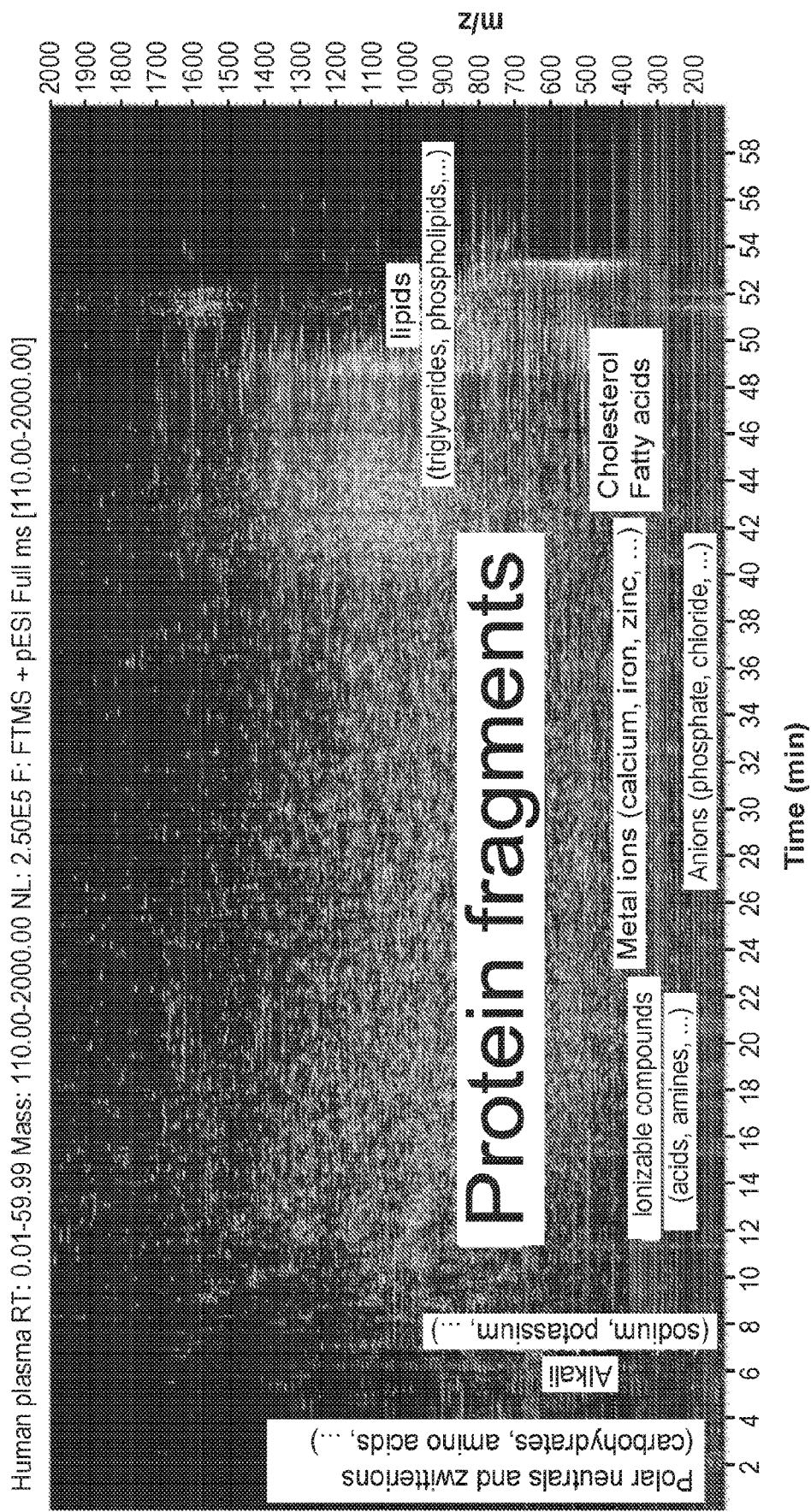
FIG. 8 shows the spectrum obtained from human plasma that was digested with trypsin and analyzed according to the described procedures. Time and mass-to-charge are represented on the horizontal and vertical axes with increasing brightness of color representing higher ion intensity. Approximate positions of select analyte classes are labeled according to previous observations.

FIG. 8 shows the spectrum obtained from human plasma that was digested with trypsin and analyzed according to the described procedures. Time and mass-to-charge are represented on the horizontal and vertical axes with increasing brightness of color representing higher ion intensity. Approximate positions of select analyte classes are labeled according to previous observations.

Figure 9:
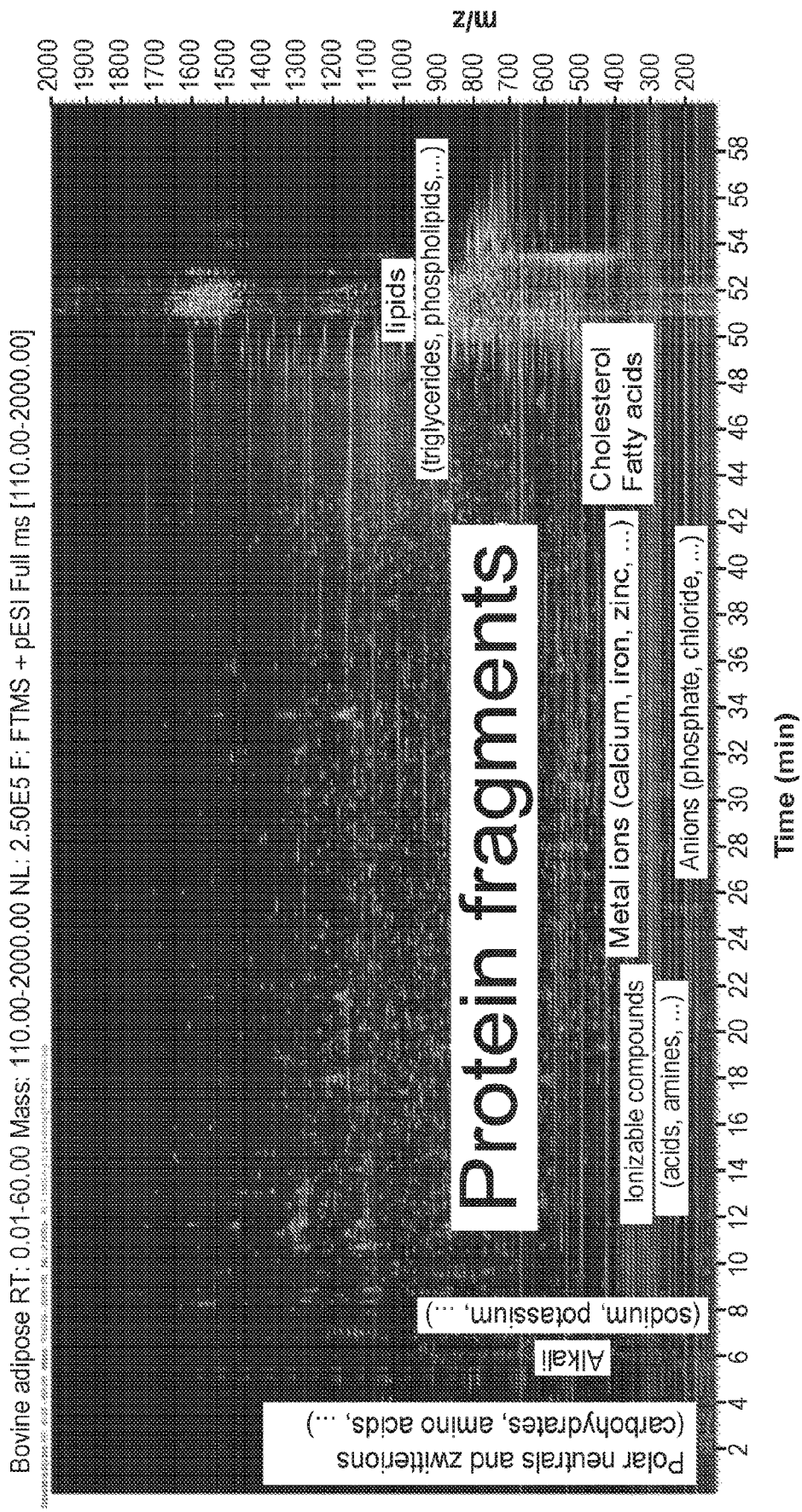
FIG. 9 shows the spectrum obtained from bovine adipose that was digested with trypsin and analyzed according to omni-MS procedures. Time and mass-to-charge are represented on the horizontal and vertical axes with increasing brightness of color representing higher ion intensity. Approximate positions of select analyte classes are labeled according to previous observations.
Figure 10:
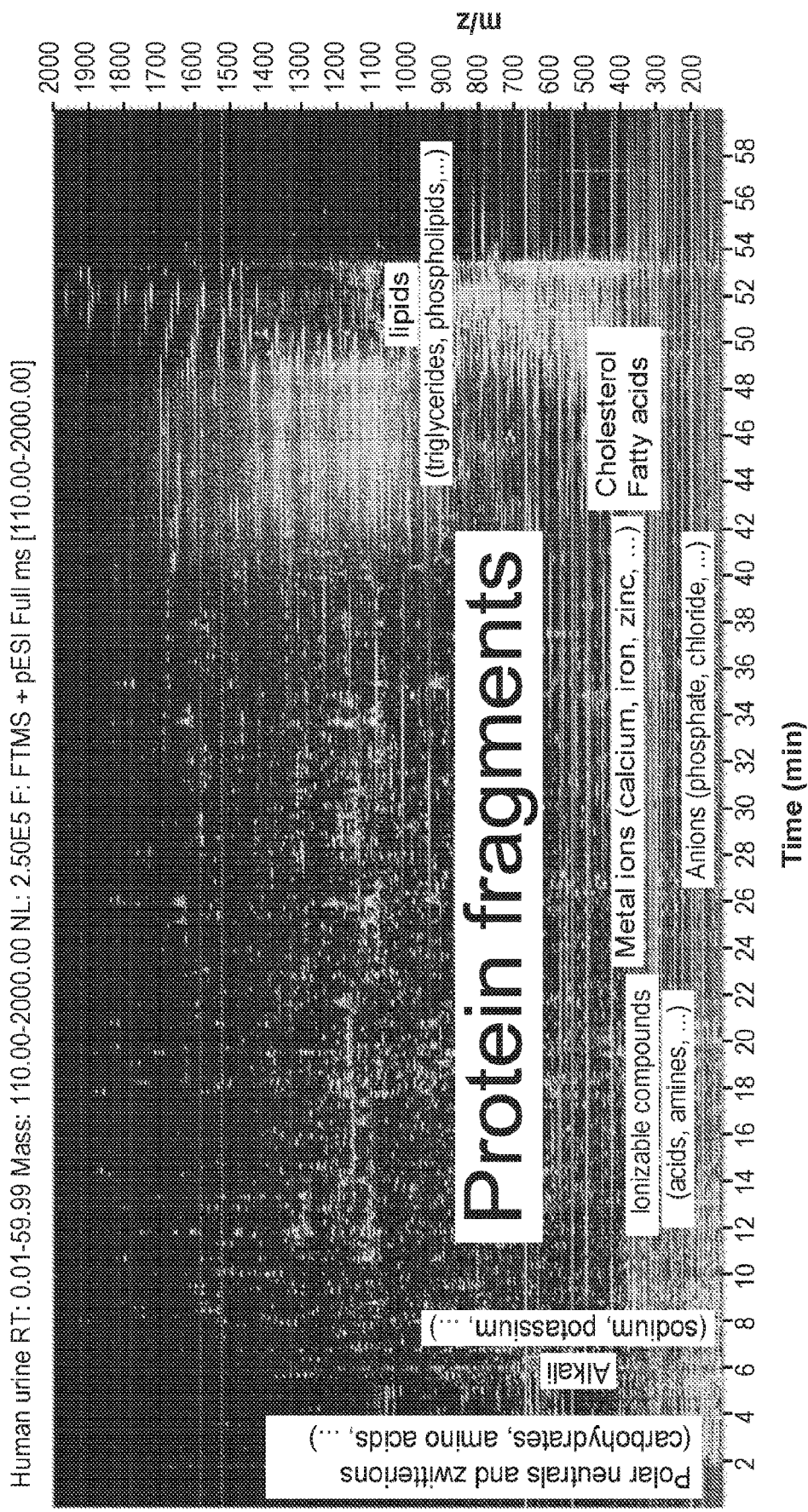
FIG. 10 shows the spectrum obtained human urine that was digested with trypsin and analyzed according to omni-MS procedures. Time and mass-to-charge are represented on the horizontal and vertical axes with increasing brightness of color representing higher ion intensity. Approximate positions of select analyte classes are labeled according to previous observations.

FIG. 9 shows the spectrum obtained from bovine adipose that was digested with trypsin and analyzed according to omni-MS procedures. Time and mass-to-charge are represented on the horizontal and vertical axes with increasing brightness of color representing higher ion intensity. Approximate positions of select analyte classes are labeled according to previous observations.

FIG. 10 shows the spectrum obtained human urine that was digested with trypsin and analyzed according to omni-MS procedures. Time and mass-to-charge are represented on the horizontal and vertical axes with increasing brightness of color representing higher ion intensity. Approximate positions of select analyte classes are labeled according to previous observations.

Figure 11:
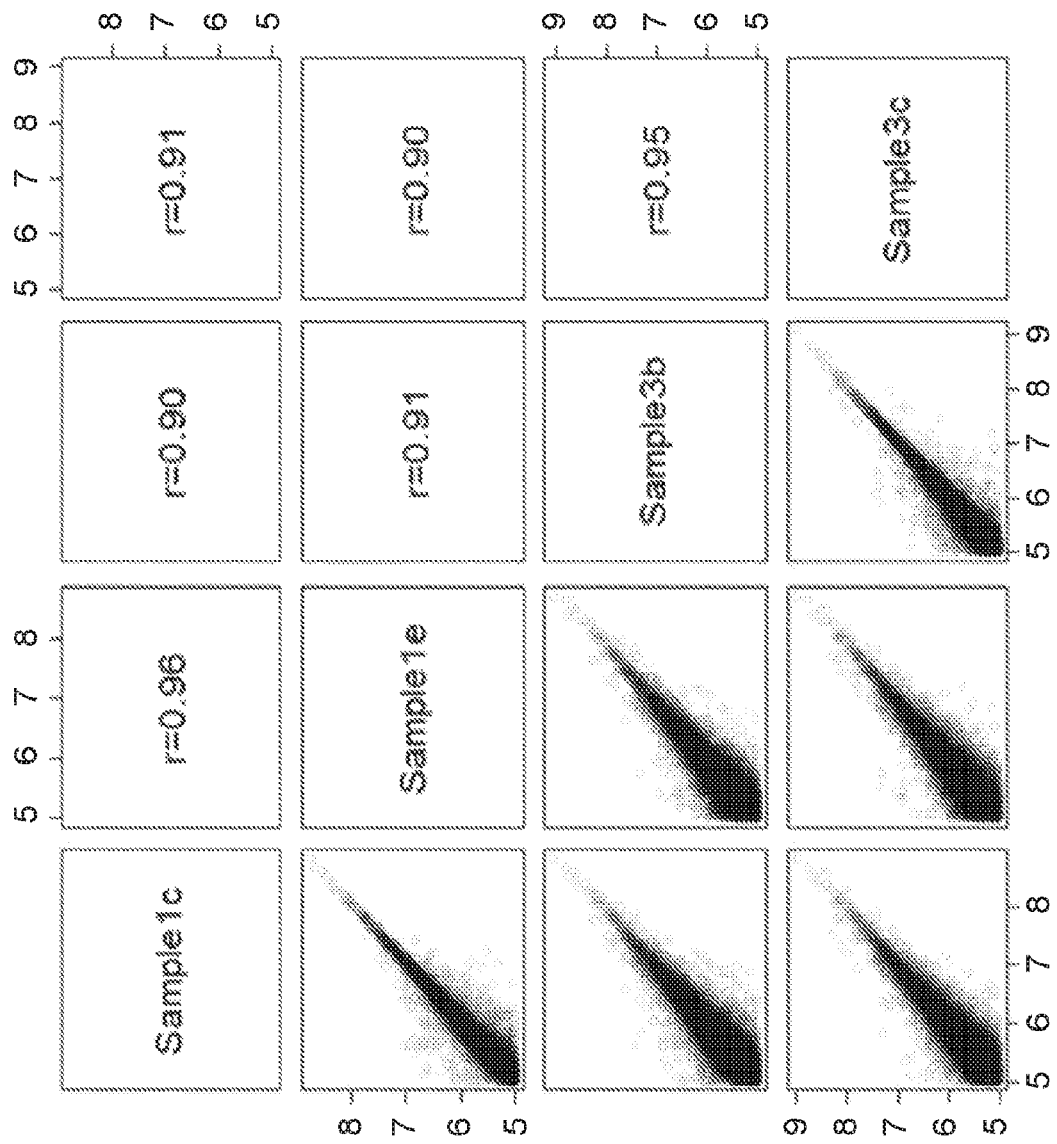
FIG. 11, left panel, representative pairwise scatterplots of ion bins across representative plasma samples and replicates. Horizontal and vertical axes correspond to log 10 intensity counts found within the ion bin. Right panel: Correlation based hierarchical clustering of plasma samples and replicates. The vertical axis is the distance in correlation between profiles, and the samples are ordered according to nearest neighbors roughly according to correlation.
Figure 11:
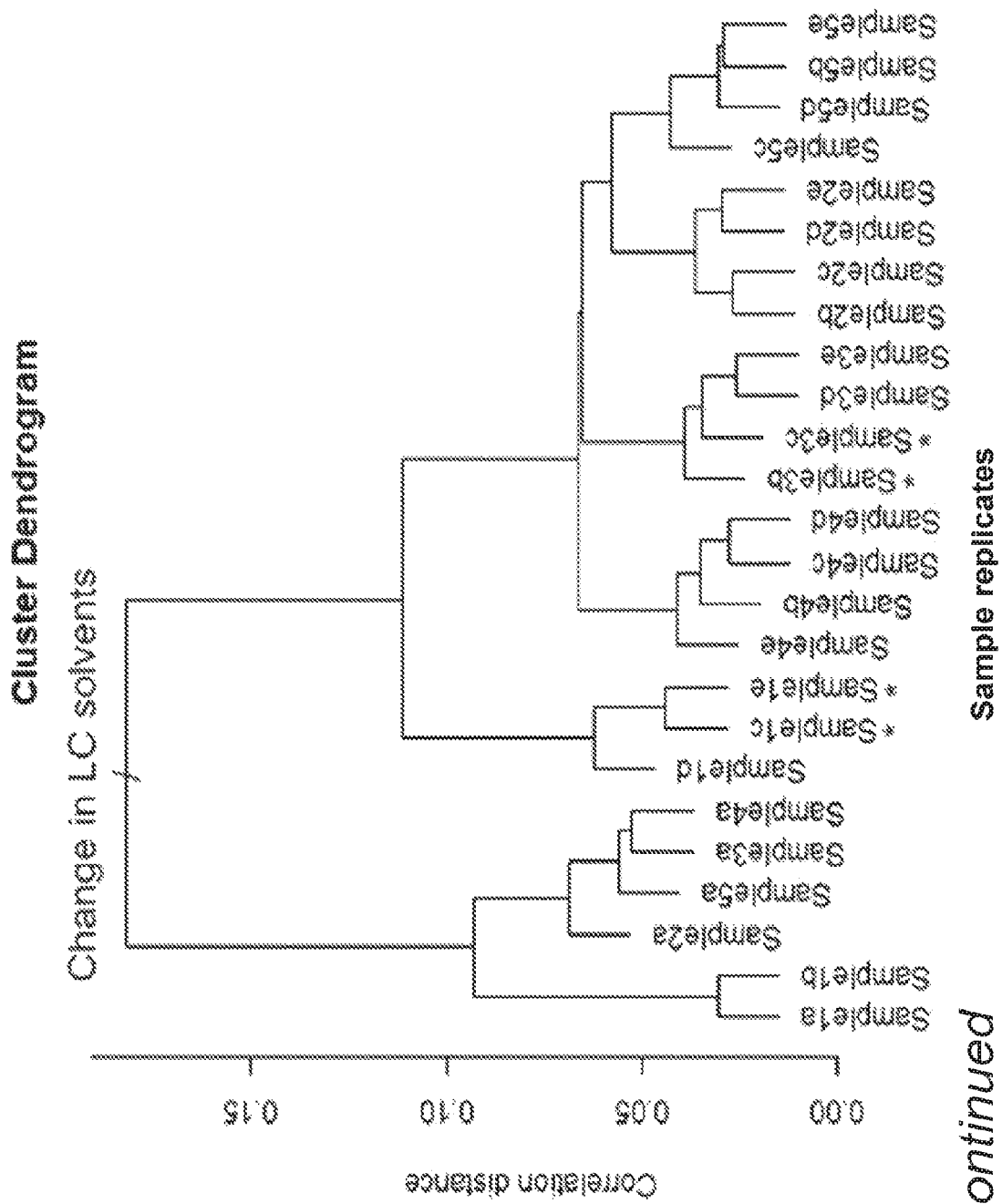

FIG. 11, left panel, representative pairwise scatterplots of ion bins across representative plasma samples and replicates. Horizontal and vertical axes correspond to log 10 intensity counts found within the ion bin. Right panel: Correlation based hierarchical clustering of plasma samples and replicates. The vertical axis is the distance in correlation between profiles, and the samples are ordered according to nearest neighbors roughly according to correlation.

Identification of a Known Clinical Indication from Multi-omic Data

Figure 12A:
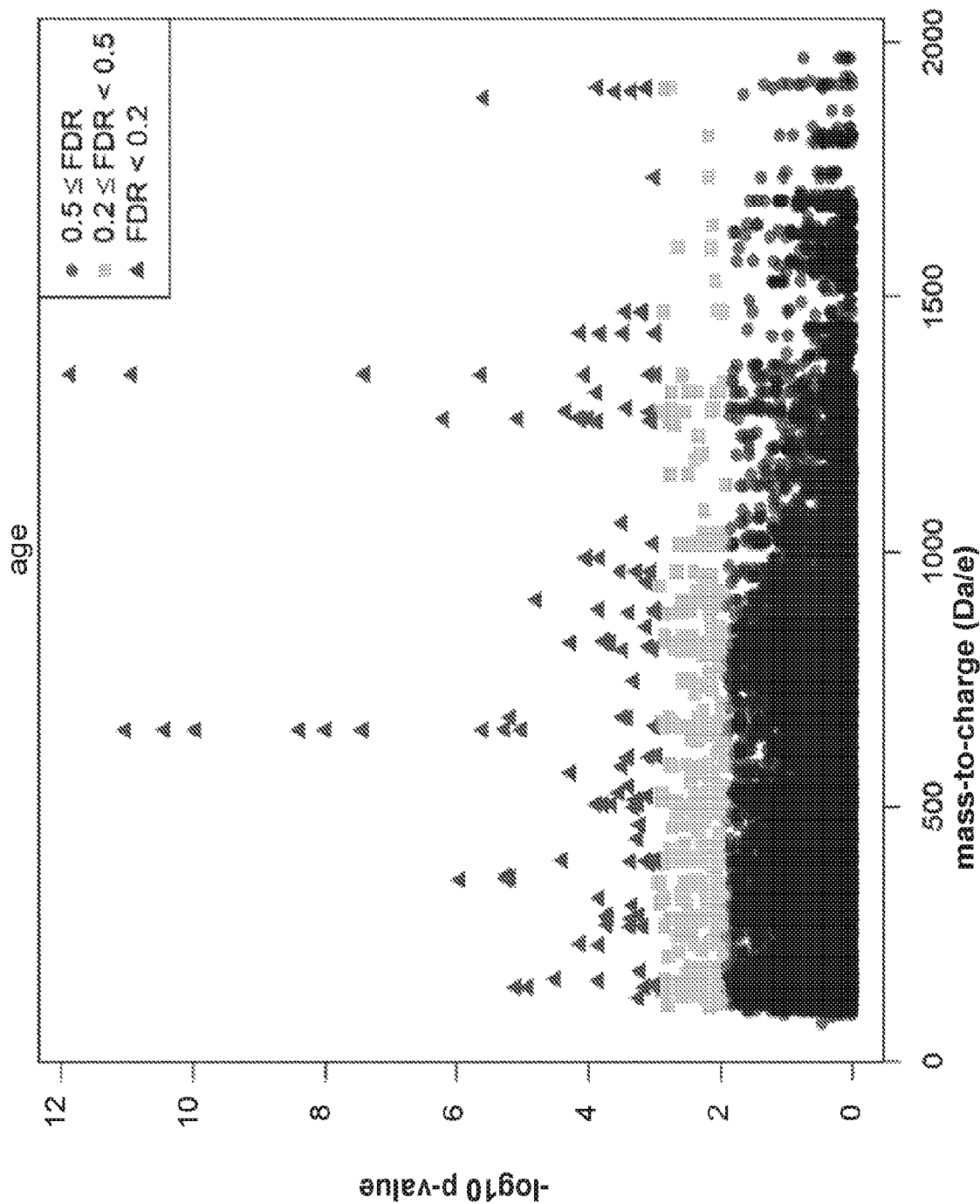
FIG. 12A illustrates a Manhattan plot displaying statistical association between various multi-omically detected analytes, each measured in mass-to-charge ratio at a retention time, from a single blood sample and a clinical variable associated with age (or aging). The statistical association results were filtered at false discovery rate (FDR) thresholds: <0.2 (red triangle), from 0.2 (inclusive) to 0.5 (green square), and ≥0.5 (grey circle).
Figure 12B:
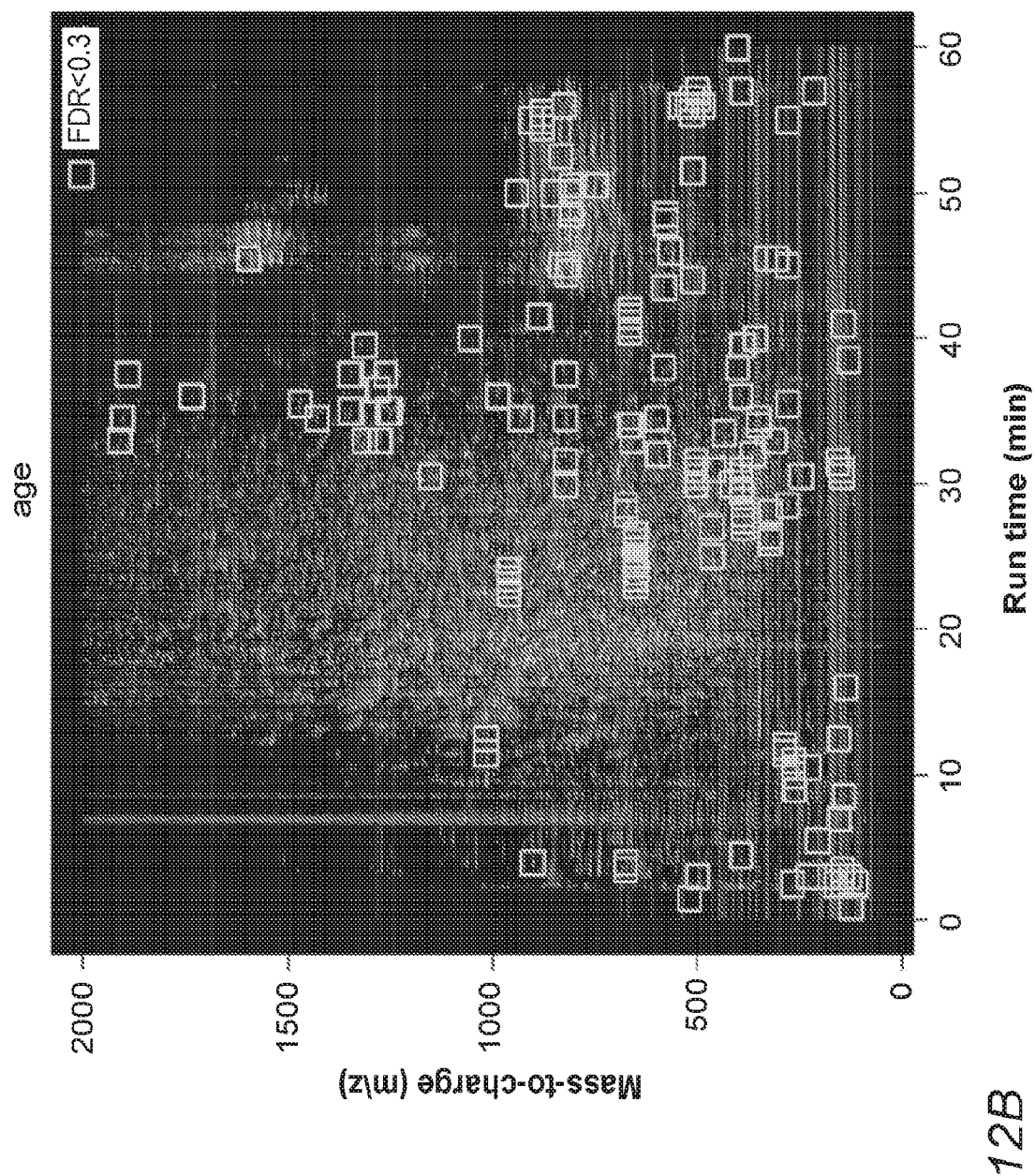
FIG. 12B illustrates a multi-omic spectrogram of the blood sample analyzed in the Manhattan plot of FIG. 12A. The analytes that fall within a 0.3 false discovery rate (FDR) threshold were marked in squares.
Figure 13A:
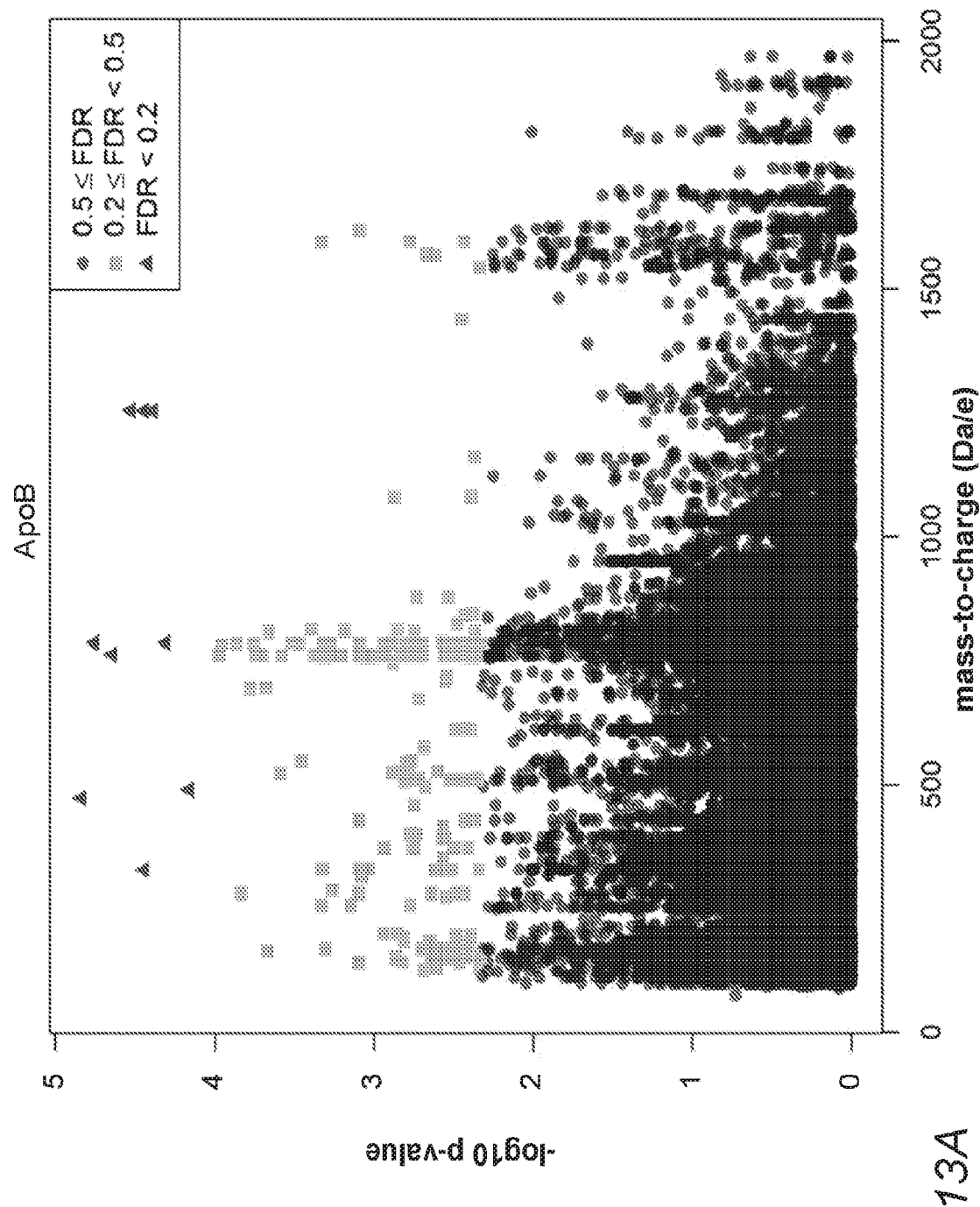
FIG. 13A illustrates a Manhattan plot displaying statistical association between various multi-omically detected analytes, each measured in mass-to-charge ratio at a retention time, from a single blood sample and a clinical variable associated with cardiovascular disease (ApoB). The statistical association results were filtered at false discovery rate (FDR) thresholds: <0.2 (red triangle), from 0.2 (inclusive) to 0.5 (green square), and ≥0.5 (grey circle).
Figure 13B:
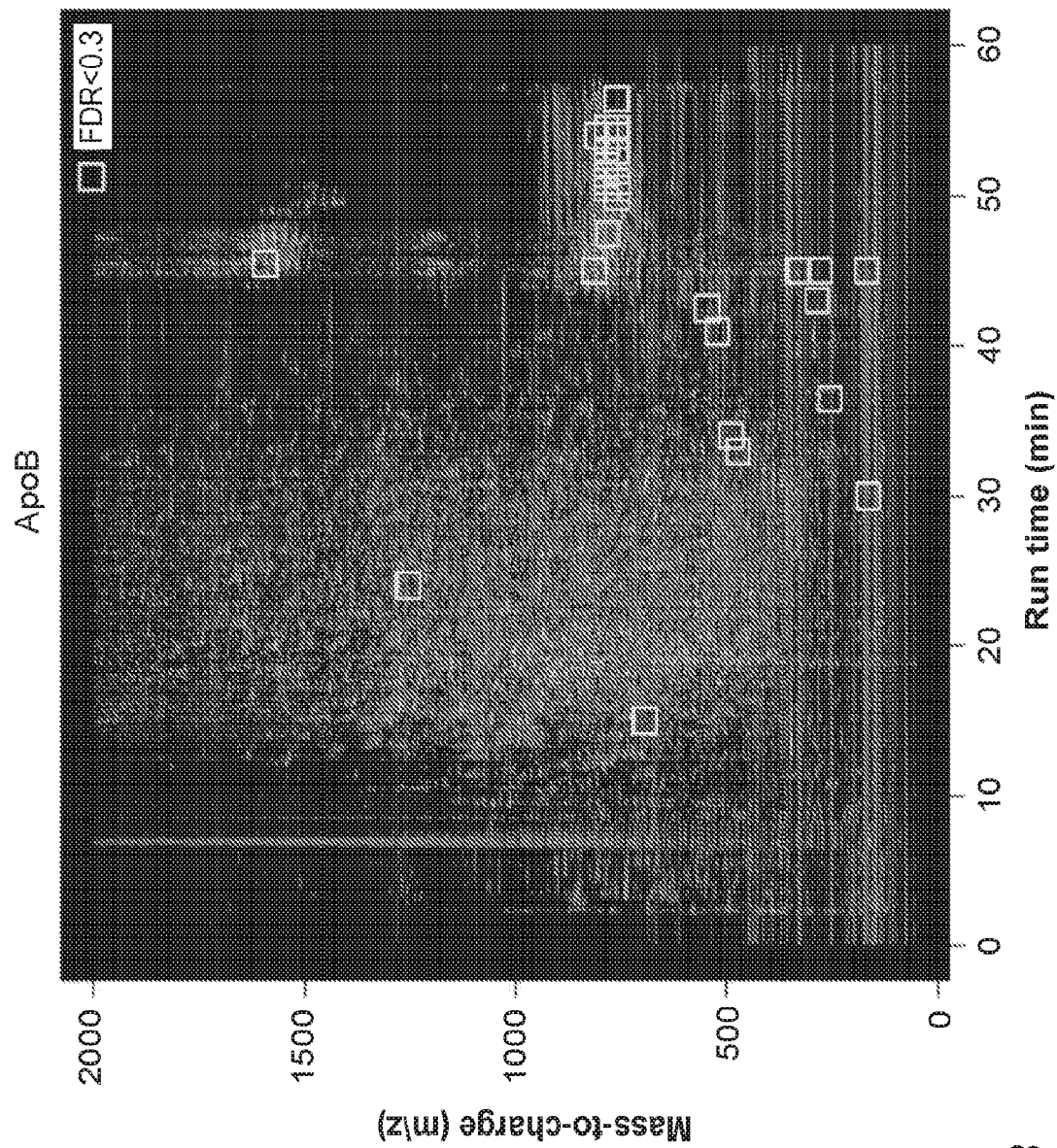
FIG. 13B illustrates a multi-omic spectrogram of the blood sample analyzed in the Manhattan plot of FIG. 13A. The analytes that fall within a 0.3 false discovery rate (FDR) threshold were marked in squares.
Figure 14A:
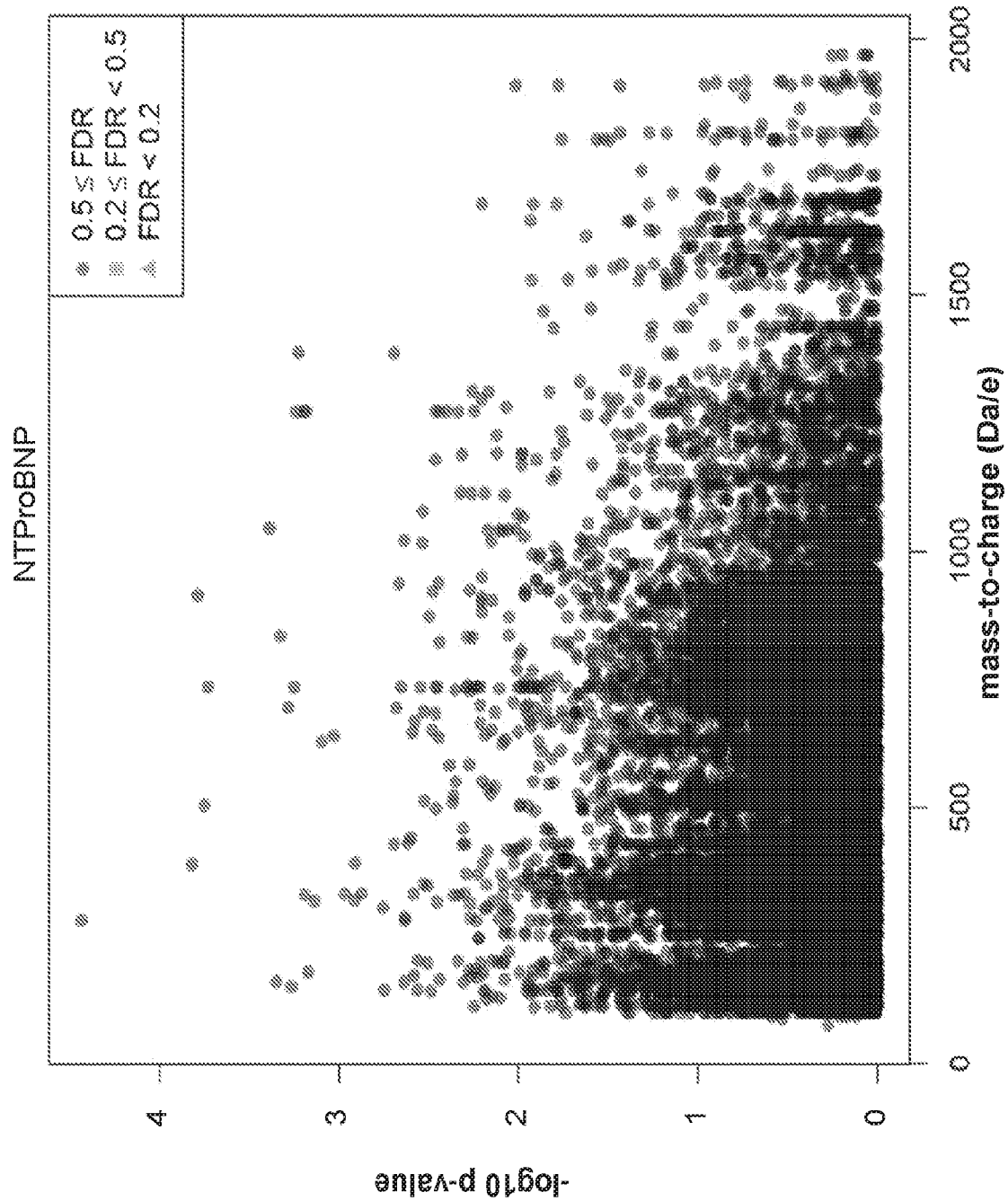
FIG. 14A illustrates a Manhattan plot displaying statistical association between various multi-omically detected analytes, each measured in mass-to-charge ratio at a retention time, from a single blood sample and a clinical variable associated with heart failure (NT-ProBNP). The statistical association results were filtered at false discovery rate (FDR) threshold: <0.2 (red triangle), from 0.2 (inclusive) to 0.5 (green square), and ≥0.5 (grey circle).
Figure 14B:
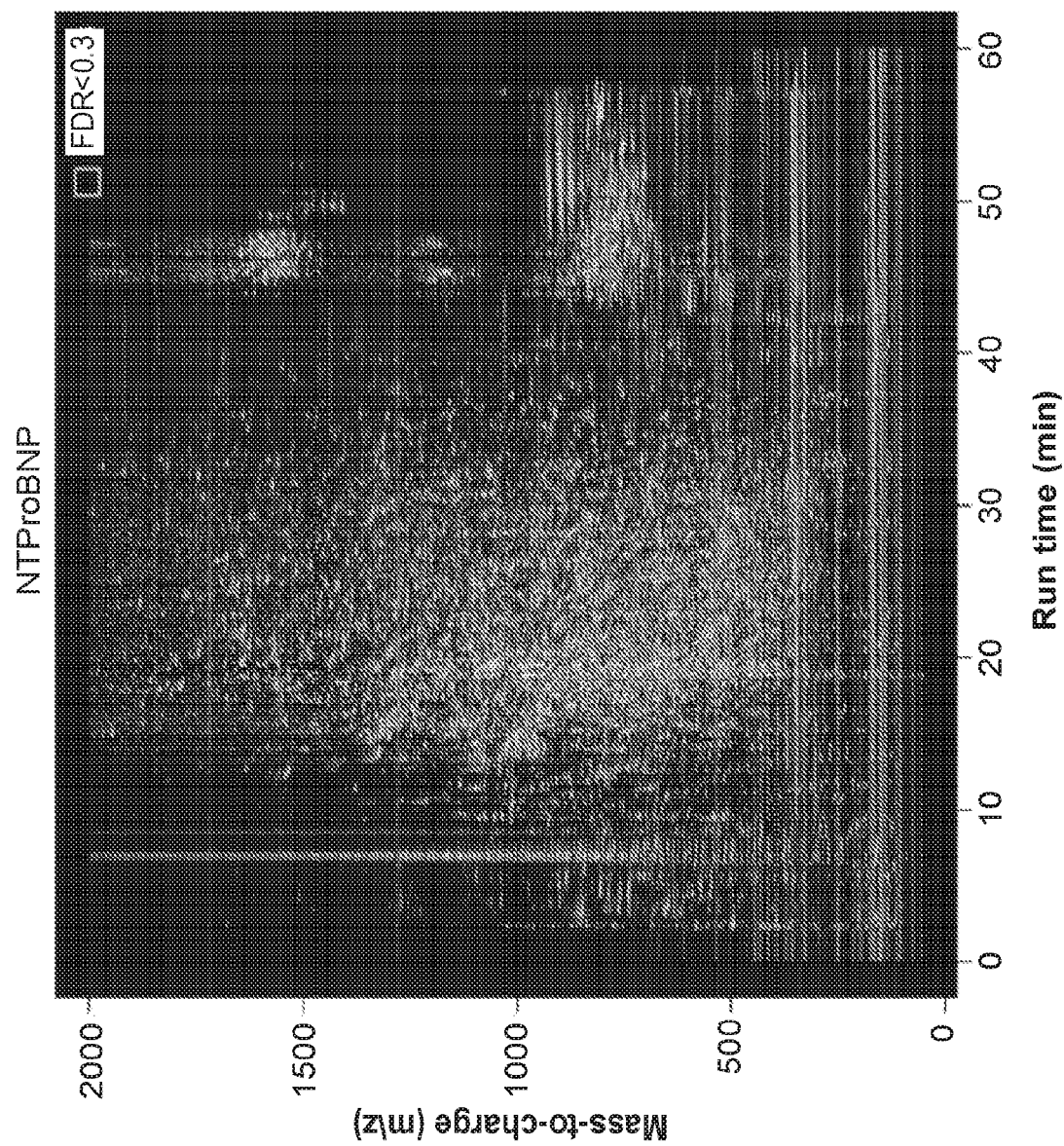
FIG. 14B illustrates a multi-omic spectrogram of the blood sample analyzed in the Manhattan plot of FIG. 14A. The analytes that fall within a 0.3 false discovery rate (FDR) threshold were marked in squares.
Figure 15A:
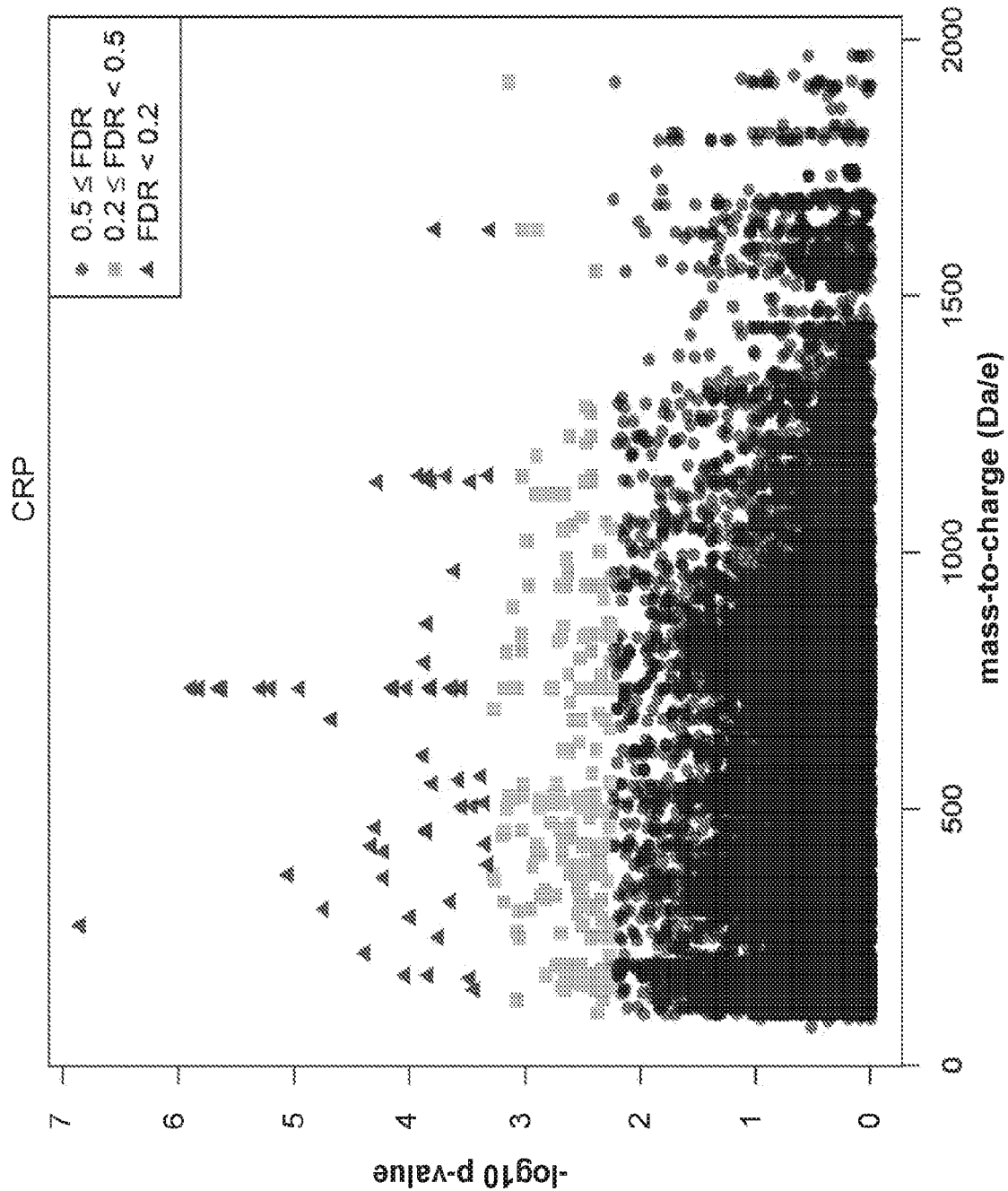
FIG. 15A illustrates a Manhattan plot displaying statistical association between various multi-omically detected analytes, each measured in mass-to-charge ratio at a retention time, from a single blood sample and a clinical variable associated with inflammation (CRP). The statistical association results were filtered at false discovery rate (FDR) thresholds: <0.2 (red triangle), from 0.2 (inclusive) to 0.5 (green square), and ≥0.5 (grey circle).
Figure 15B:
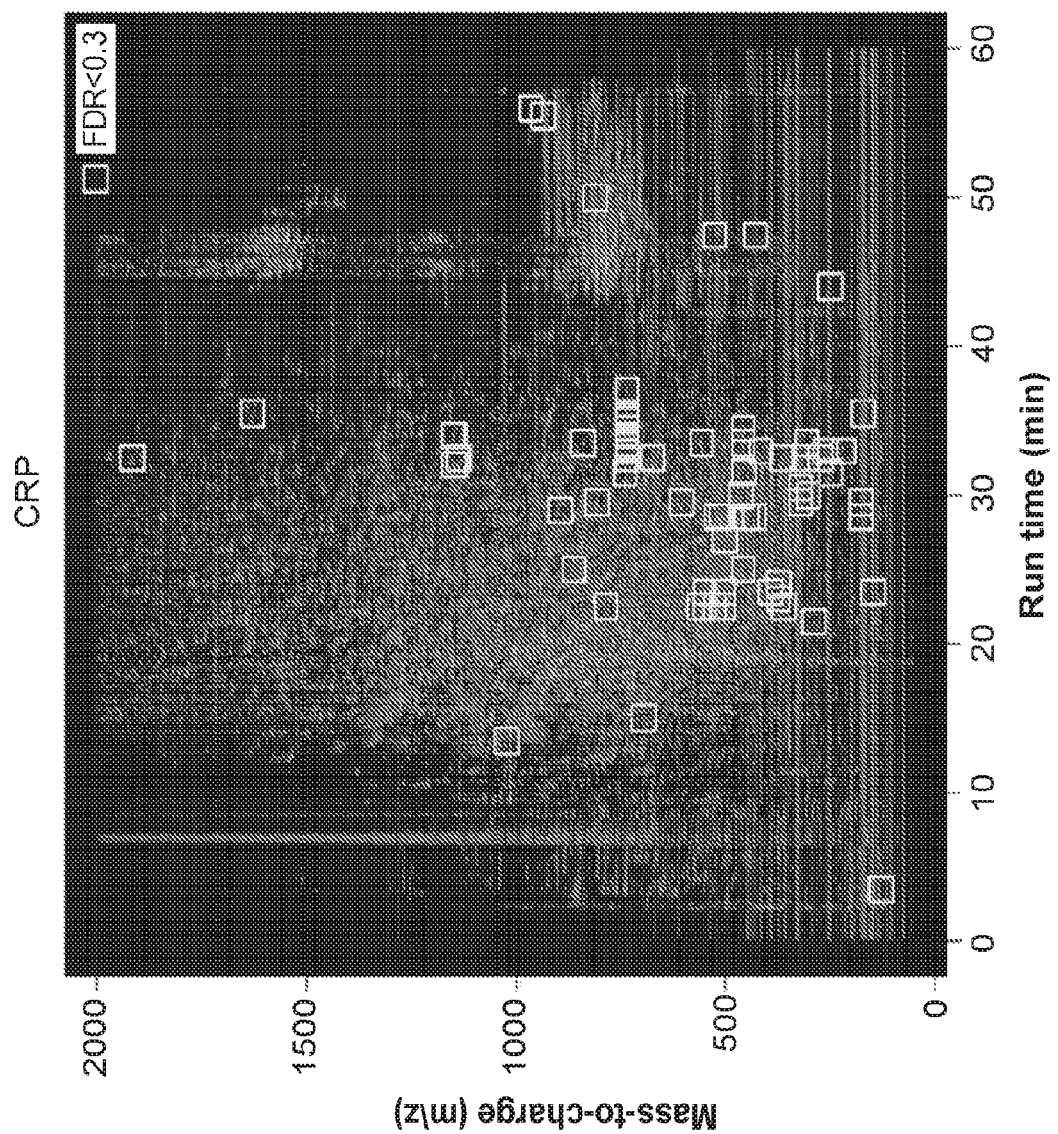
FIG. 15B illustrates a multi-omic spectrogram of the blood sample analyzed in the Manhattan plot of FIG. 15A. The analytes that fall within a 0.3 false discovery rate (FDR) threshold were marked in squares.
Figure 16A:
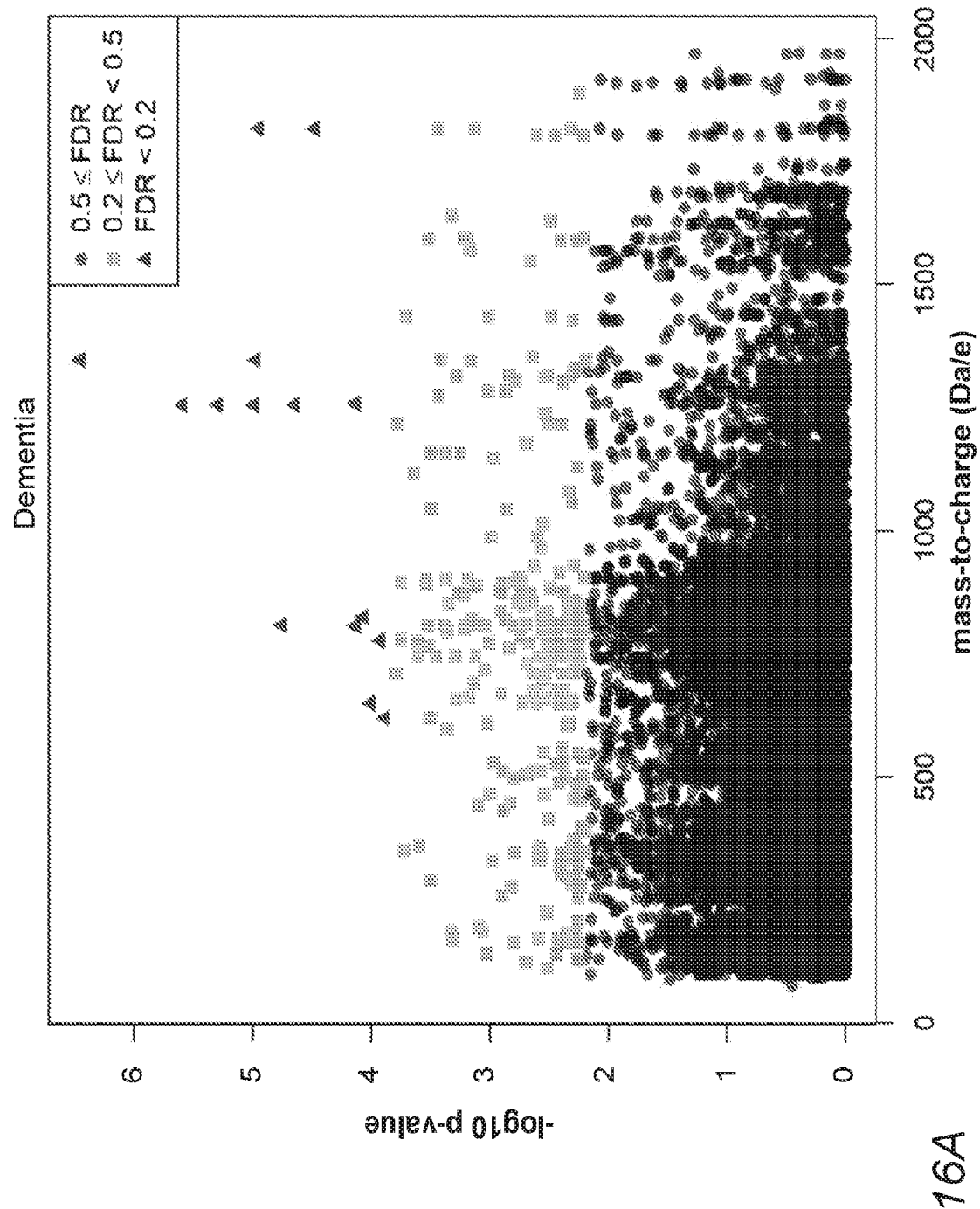
FIG. 16A illustrates a Manhattan plot displaying statistical association between various multi-omically detected analytes, each measured in mass-to-charge ratio at a retention time, from a single blood sample and a clinical variable associated with dementia. The statistical association results were filtered at false discovery rate (FDR) thresholds: <0.2 (red triangle), from 0.2 (inclusive) to 0.5 (green square), and ≥0.5 (grey circle).
Figure 16B:
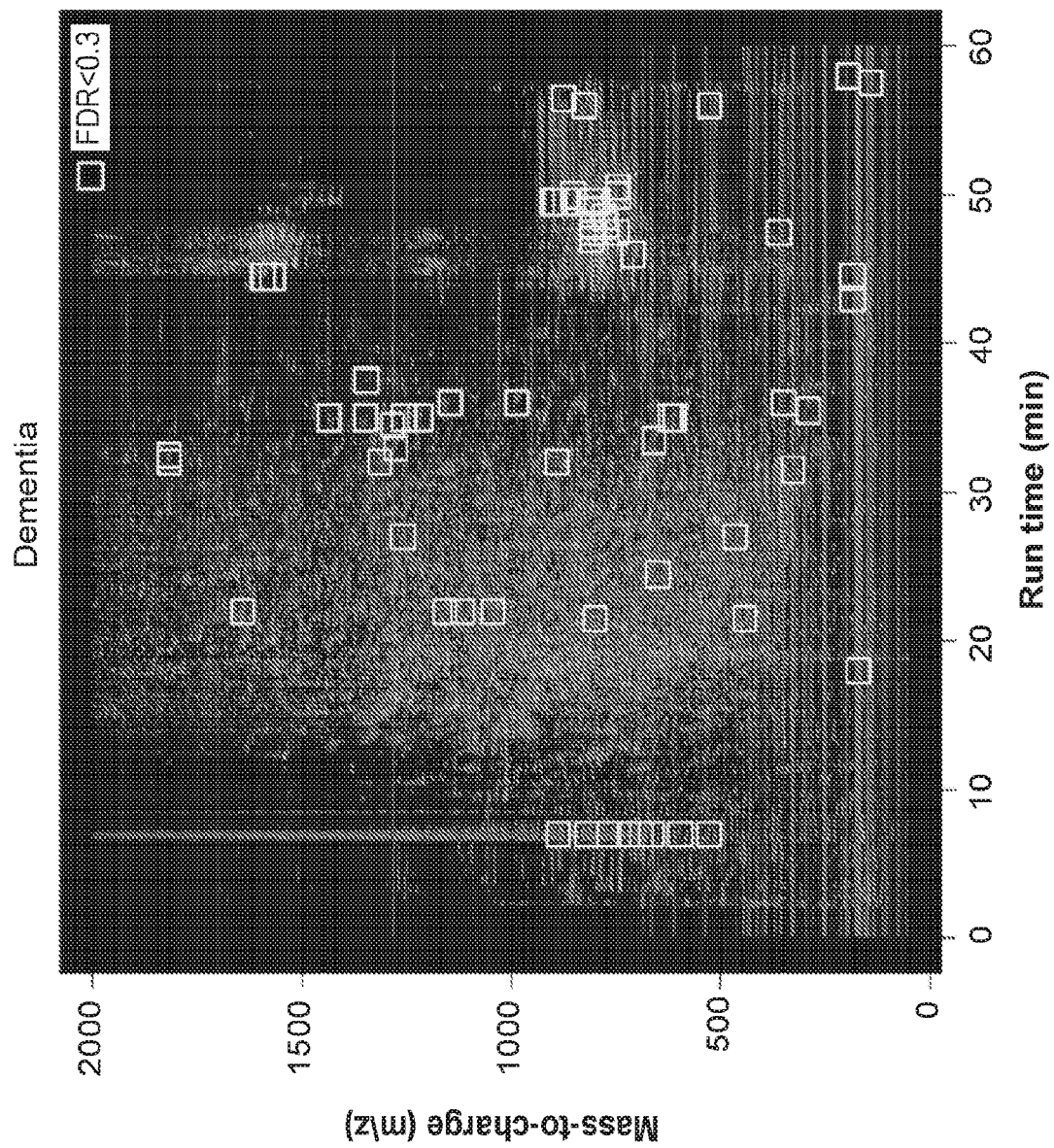
FIG. 16B illustrates a multi-omic spectrogram of the blood sample analyzed in the Manhattan plot of FIG. 16A. The analytes that fall within a 0.3 false discovery rate (FDR) threshold were marked in squares.

Multiomic data were obtained from a biobanked clinical plasma or serum sample using the multiomic method as described hereinabove or described anywhere else herein. The obtained multiomic data (i.e., spectrograms of FIGS. 12B, 13B, 14B, 15B, and 16B) were summed into pixel "bins," each representing a detected analyte, based on the mass-to-charge ratio and the retention time of the detected analytes. The obtained multiomic data were subsequently analyzed using bioinformatics such as Manhattan plot with false discovery rate (FDR) and statistical association(s) with at least one clinical indicator was identified. The clinical indicator selected was known to be associated with a disease or condition, such as age or aging (FIGS. 12A-12B), cardiovascular disease risk (FIGS. 13A-13B), heart failure (FIGS. 14A-14B), inflammation (FIGS. 15A-15B), or dementia (FIGS. 16A-16B). In particular, Manhattan plots (i.e., FIGS. 12A, 13A, 14A, 15A, and 16A) were used to illustrate statistically significant analytes.

FIGS. 12A, 13A, 14A, 15A, and 16A each illustrate a Manhattan plot displaying statistical association between various multi-omically detected analytes from a single sample and a clinical variable, respectively, associated with age, cardiovascular disease, heart failure, inflammation, and dementia. The statistical association results were filtered at false discovery rate (FDR) thresholds: <0.2 (red triangle), from 0.2 (inclusive) to 0.5 (green square), and ≥0.5 (grey circle).

FIGS. 12B, 13B, 14B, 15B, and 16B each illustrates a multi-omic spectrogram of the blood sample analyzed in the corresponding Manhattan plot. The analytes that fall within a 0.3 false discovery rate (FDR) threshold were marked in squares.

Model Training and Validation Using Multiomic Data

A predictive model, the elastic net regression model with cross-validation (such as described in Zou and Hastie (Journal of the Royal Statistical Society: Series B (Statistical Methodology) 67.2 (2005): 301-320), which is incorporated in its entirety by reference) was used to demonstrate that the multiomic data obtained using the multiomic method as described hereinabove or described anywhere else herein can be used to train predictive models. One of skill in the art will understand that other machine learning algorithms (such as linear regressions (e.g. Lasso or Ridge) or support vector machines) can be trained by the multiomic data obtained using the multiomic method as described hereinabove or described anywhere else herein. A leave one out strategy was implemented in the cross-validation method (such as a 10-fold cross-validation). One of skill in the art will understand that, in one 10-fold cross-validation approach, the obtained multiomic data may be randomly split into ten subsets, of which nine used to train and one used to test across all permutations. The training of the model further included tuning the hyperparameter settings to achieve the lowest cross-validation test set error. The trained predictive model was then tested on the remaining subset to predict the clinical label (indication) from the multiomic data. One indication at a time was predicted using the aforementioned predictive model and training strategy.

Figure 12C:
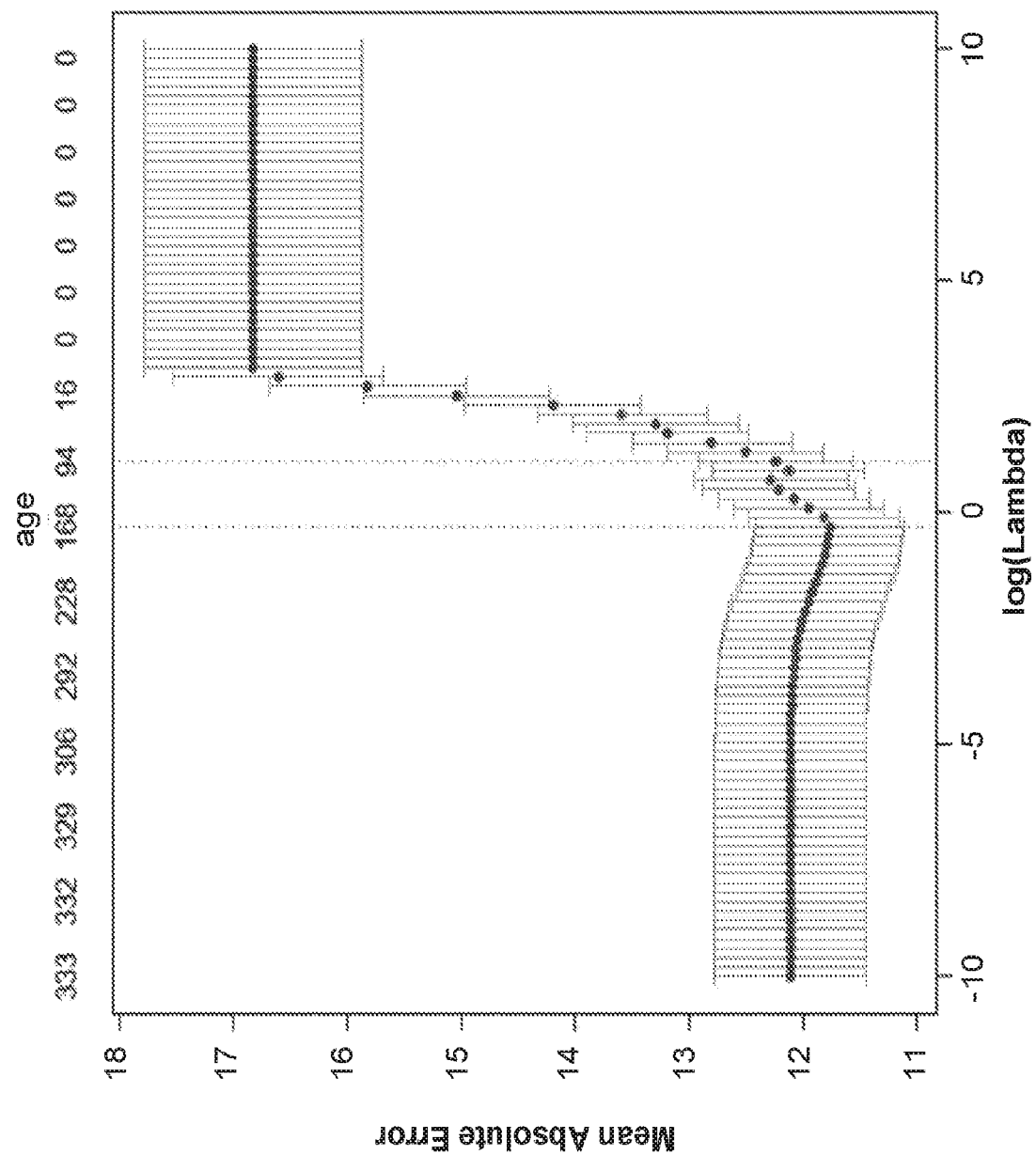
FIG. 12C illustrates mean absolute error (MAE) of a set of predictions on age using leave-one-out-cross validation while varying the degrees of freedom of the machine learning model.
Figure 12D:
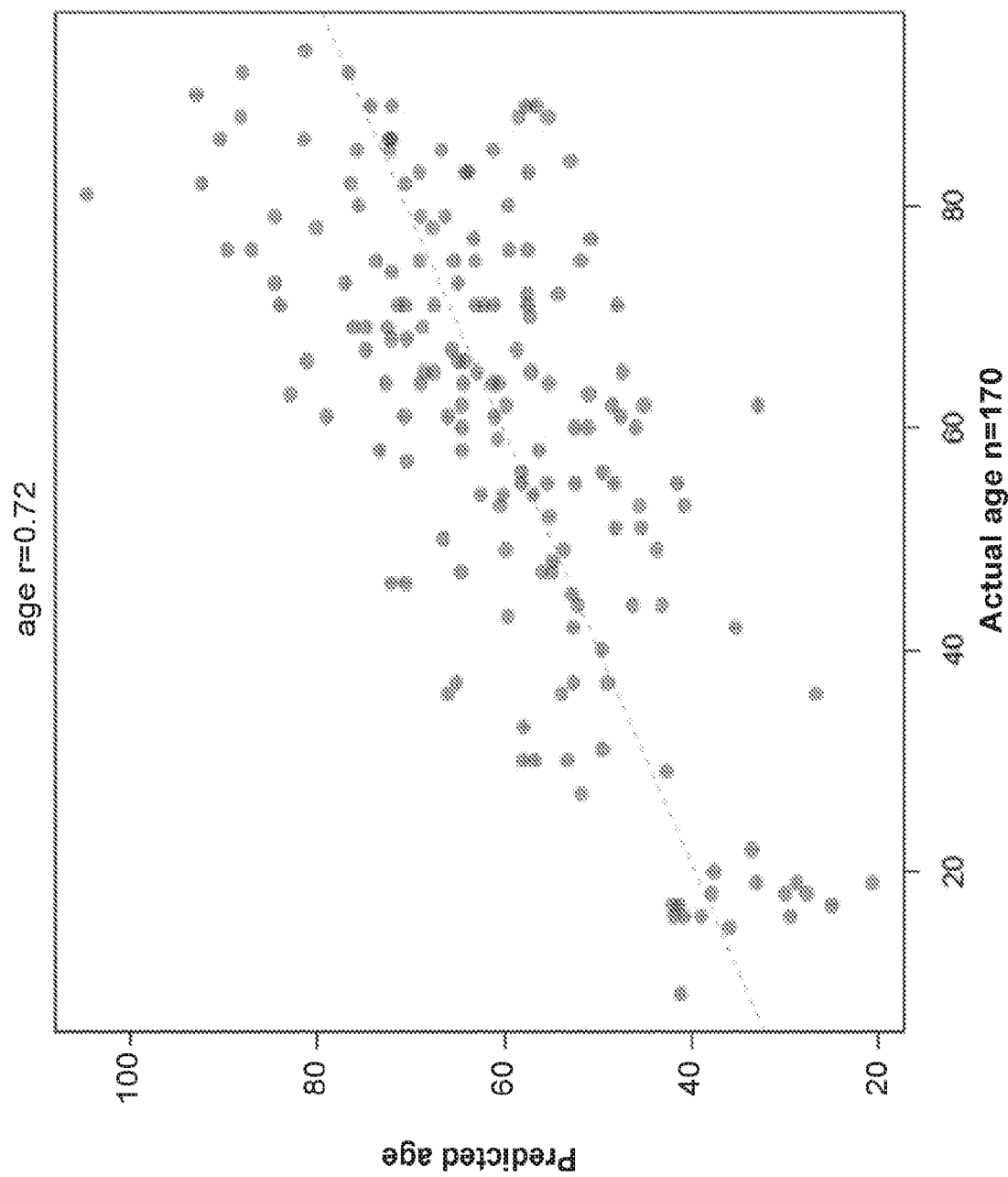
FIG. 12D illustrates prediction accuracy by comparing predicted age (using the method as described herein) and actual age. The correlation co-efficient (r) is shown above the plot; and the sample size (n) is shown below the plot.

FIG. 12C illustrates mean absolute error (MAE) of a set of predictions on age using leave-one-out-cross validation while varying the degrees of freedom of the machine learning model. The bottom axis of FIG. 12C displays a unitless parameter setting of the elastic net regression model that controls the degree of freedom that the model has access to. The upper axis of FIG. 12C displays the number of variables selected from the data used to make the prediction. The left vertical axis of FIG. 12C displays the mean absolute error of the predicted age (years), as compared to the measured age across the 10-fold cross-validation as discussed hereinabove.

Figure 13C:
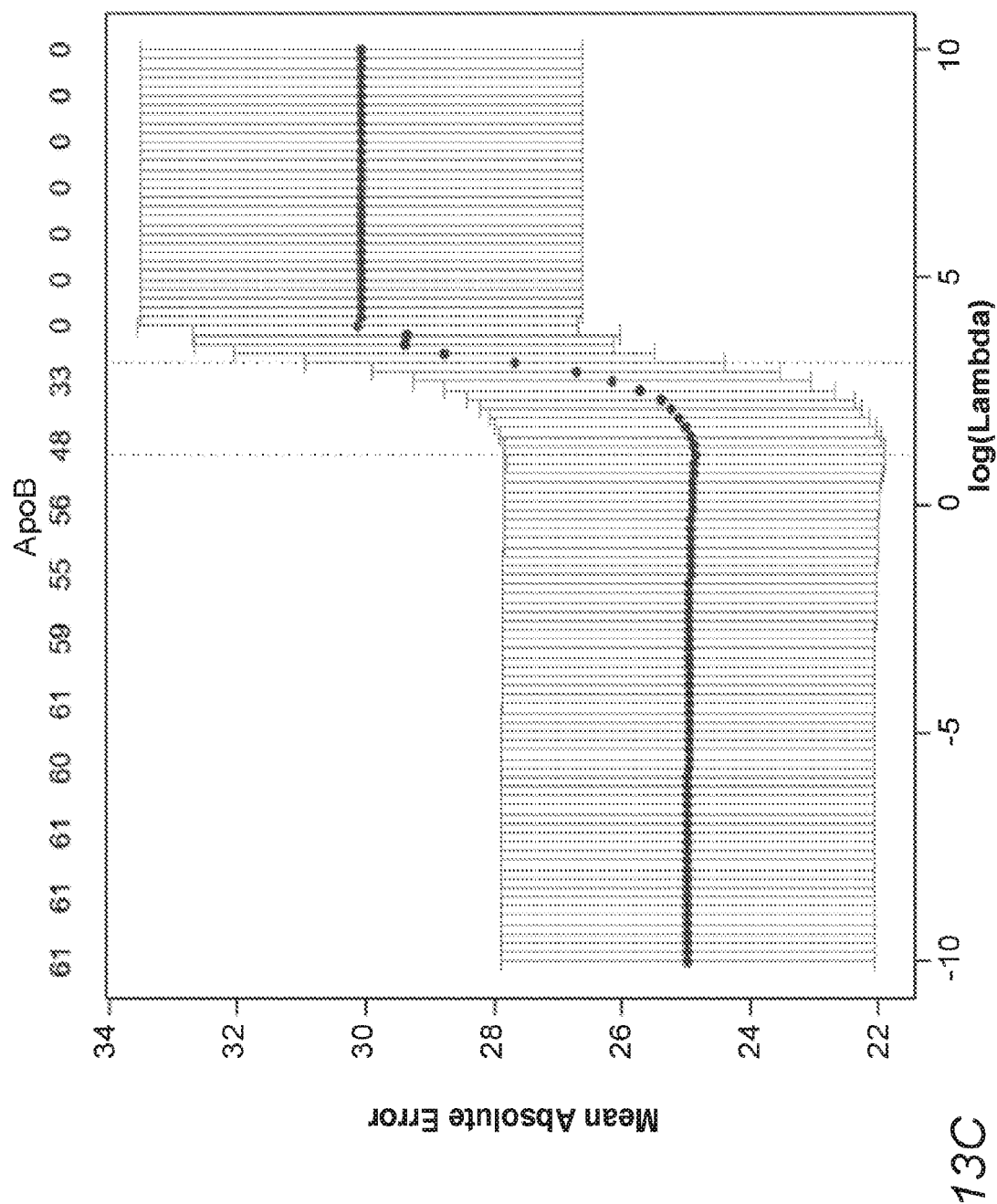
FIG. 13C illustrates mean absolute error (MAE) of a set of predictions on ApoB leave-one-out-cross validation while varying the degrees of freedom of the machine learning model.
Figure 13D:
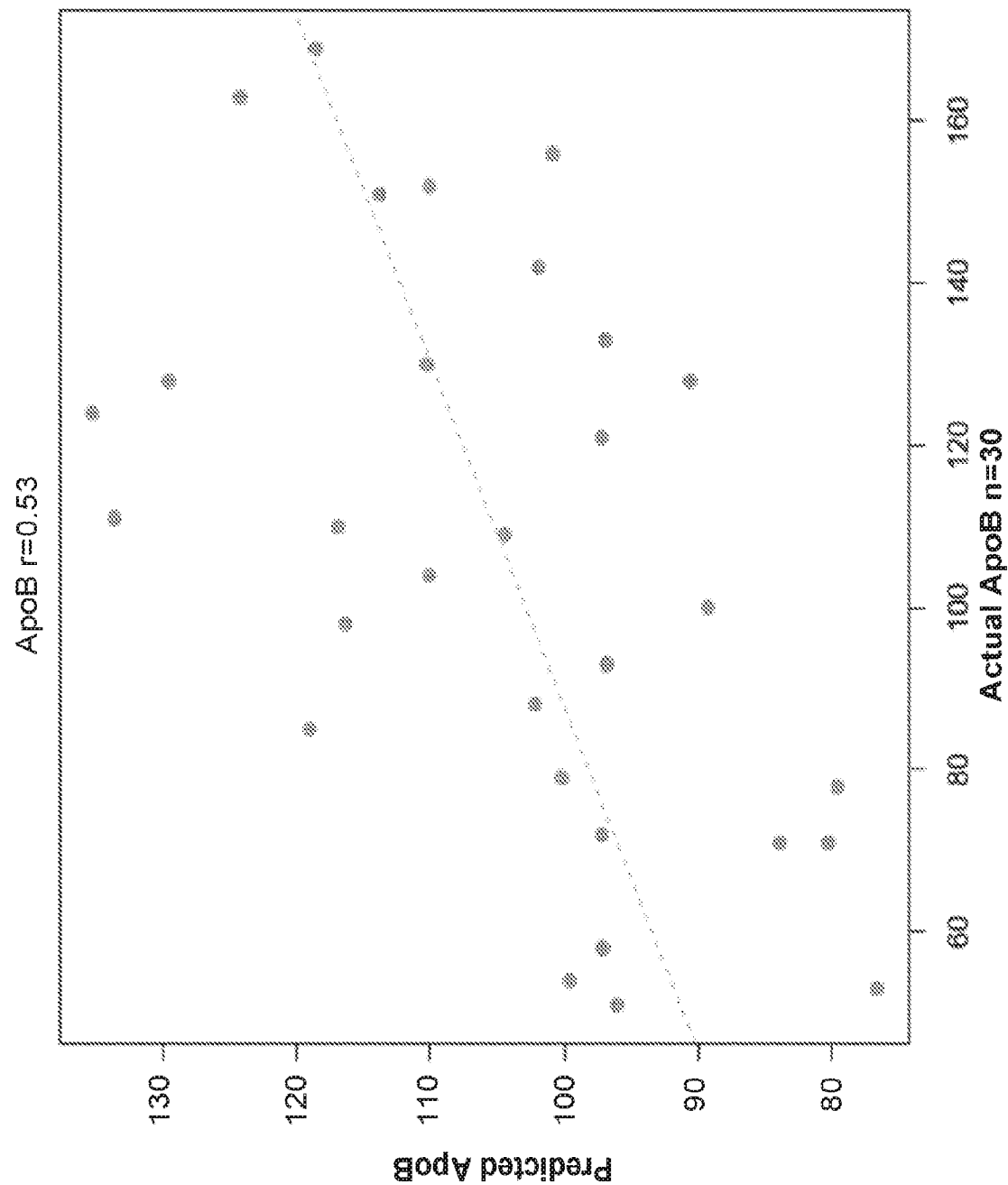
FIG. 13D illustrates prediction accuracy by comparing predicted ApoB (using the method as described herein) and actual ApoB. The correlation co-efficient (r) is shown above the plot; and the sample size (n) is shown below the plot.

FIG. 13C illustrates mean absolute error (MAE) of a set of predictions on ApoB leave-one-out-cross validation while varying the degrees of freedom of the machine learning model. The bottom axis of FIG. 13C displays a unitless parameter setting of the elastic net regression model that controls the degree of freedom that the model has access to. The upper axis of FIG. 13C displays the number of variables selected from the data used to make the prediction. The left vertical axis of FIG. 13C displays the mean absolute error of the predicted ApoB level (mg/dL), as compared to the measured value across the 10-fold cross-validation as discussed hereinabove.

Figure 14C:
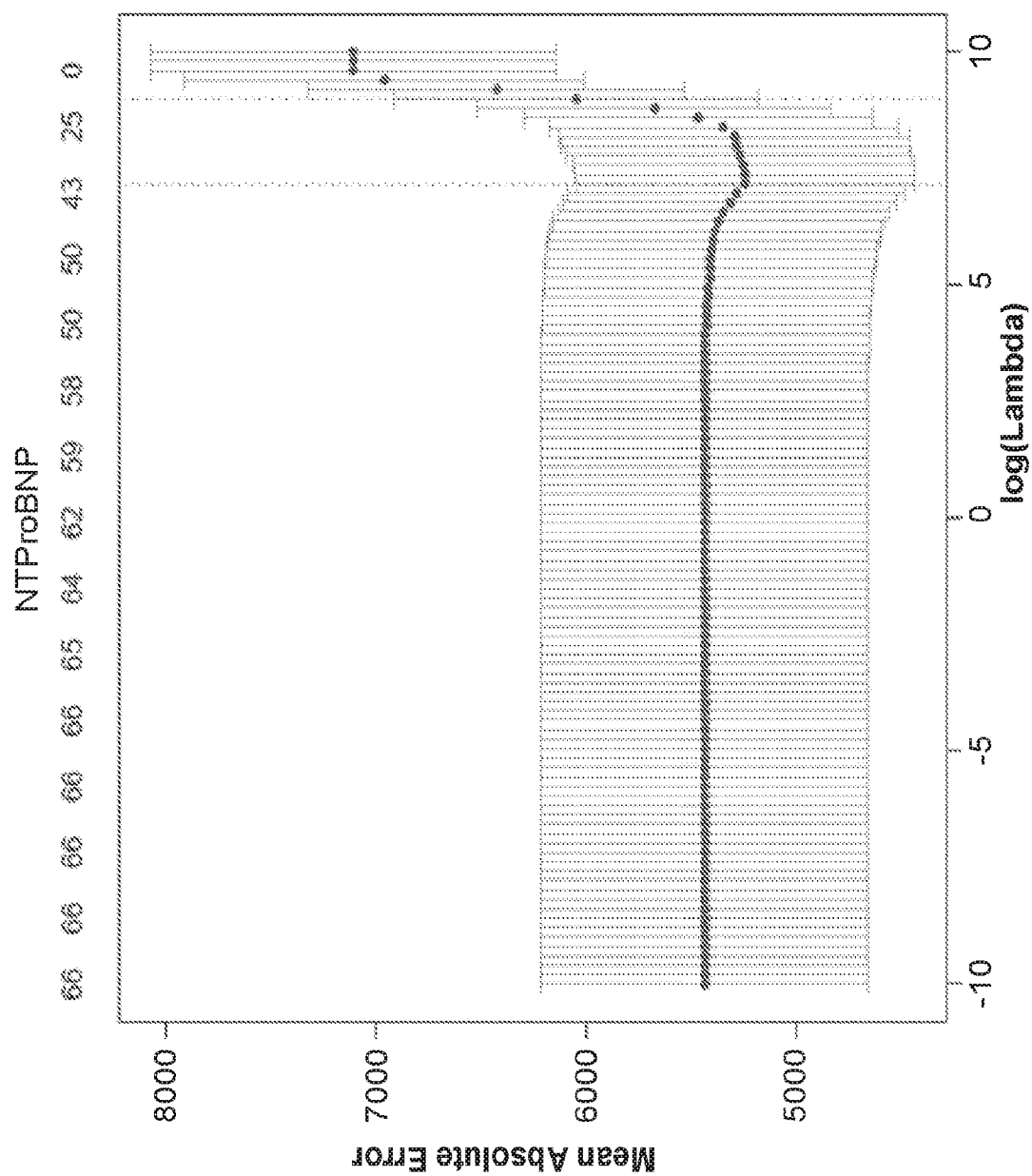
FIG. 14C illustrates mean absolute error (MAE) of a set of predictions on N-terminal pro b-type natriuretic peptide (NT-ProBNP) using leave-one-out-cross validation while varying the degrees of freedom of the machine learning model.
Figure 14D:
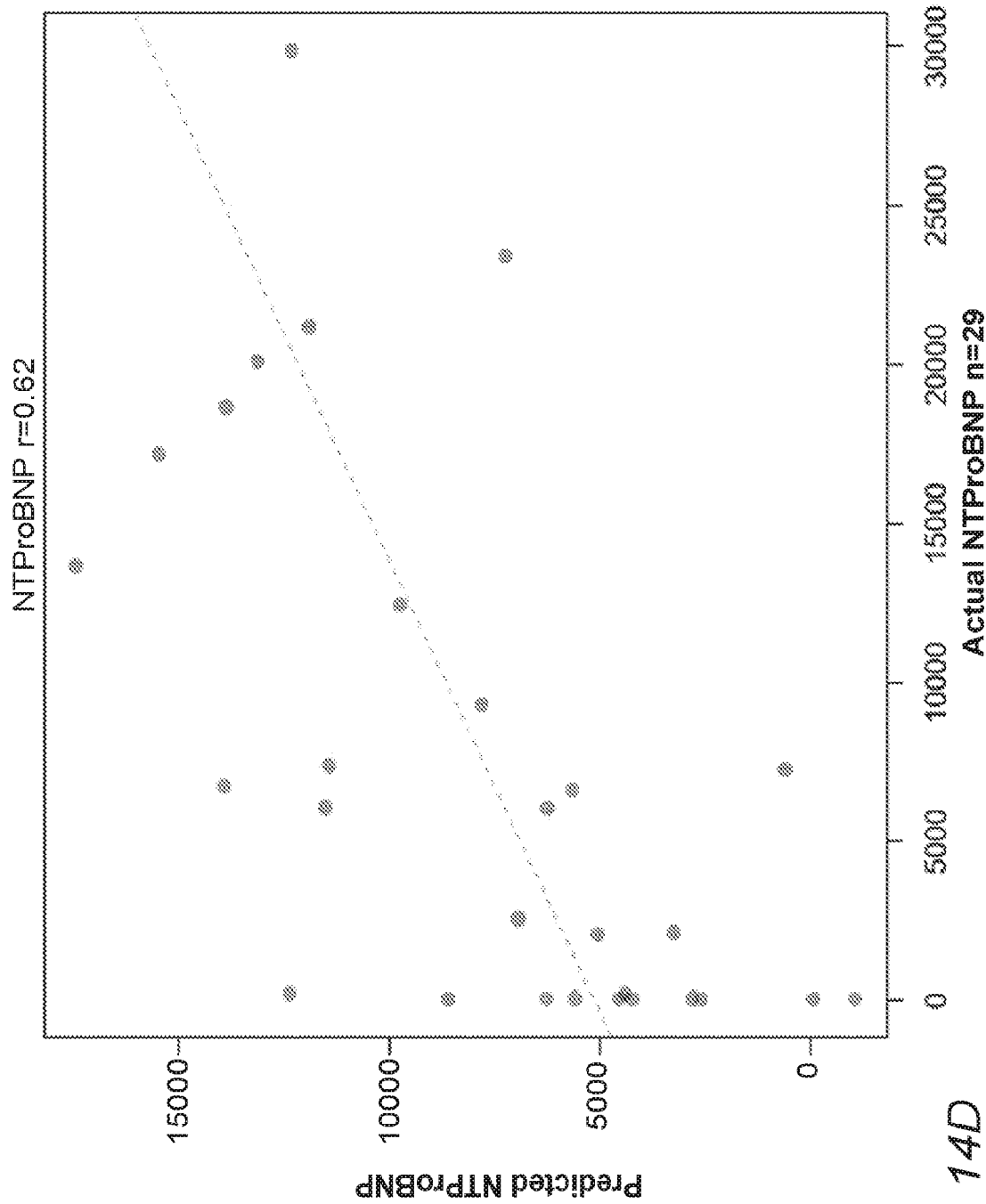
FIG. 14D illustrates prediction accuracy by comparing predicted NT-ProBNP (using the method as described herein) and actual NT-ProBNP. The correlation co-efficient (r) is shown above the plot; and the sample size (n) is shown below the plot.

FIG. 14C illustrates mean absolute error (MAE) of a set of predictions on N-terminal pro b-type natriuretic peptide (NT-ProBNP) using leave-one-out-cross validation while varying the degrees of freedom of the machine learning model. The bottom axis of FIG. 14C displays a unitless parameter setting of the elastic net regression model that controls the degree of freedom that the model has access to. The upper axis of FIG. 14C displays the number of variables selected from the data used to make the prediction. The left vertical axis of FIG. 14C displays the mean absolute error of the predicted NT-ProBNP level (pg/mL), as compared to the measured value across the 10-fold cross-validation as discussed hereinabove.

Figure 15C:
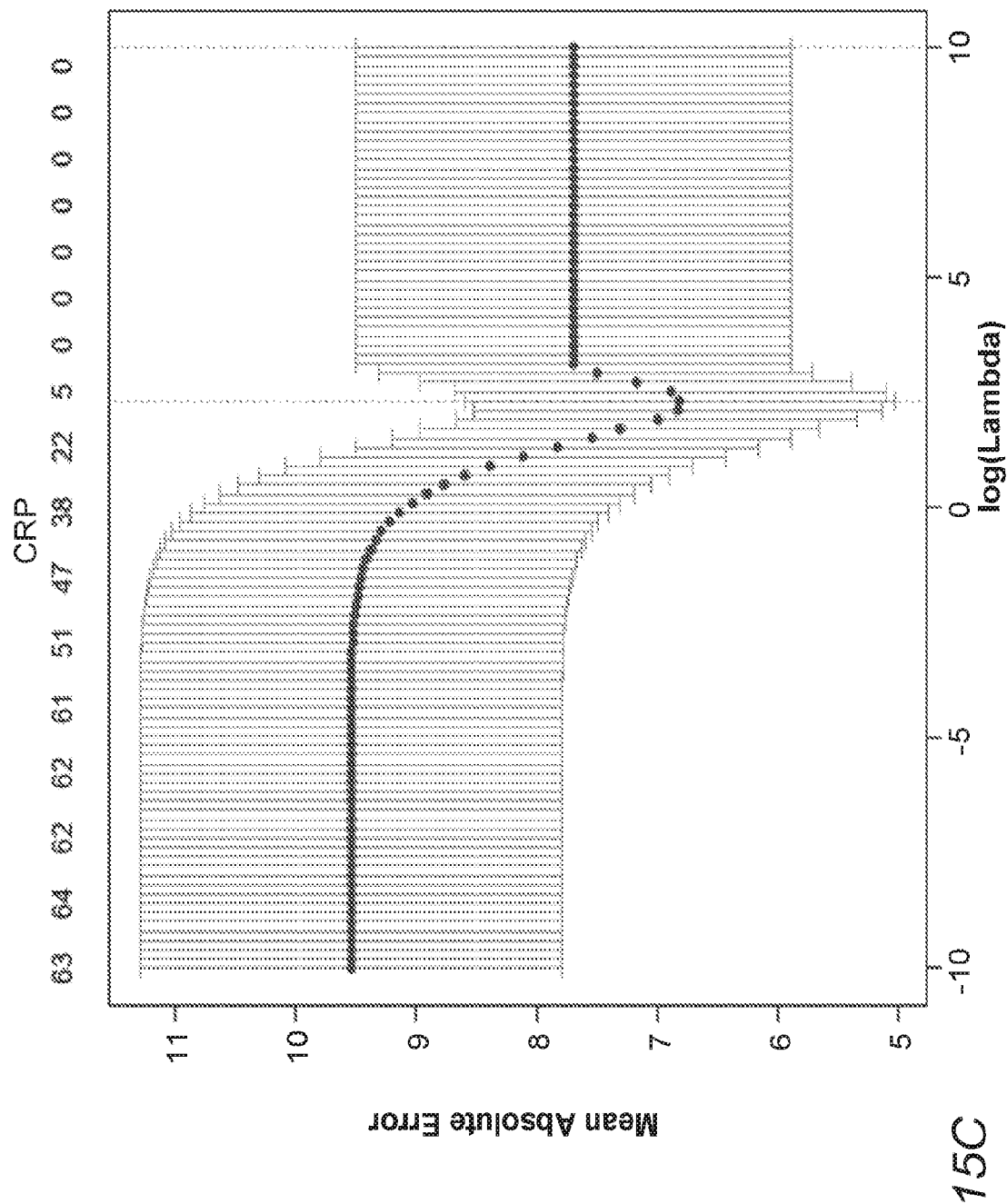
FIG. 15C illustrates mean absolute error (MAE) of a set of predictions on C-reactive protein (CRP) leave-one-out-cross validation while varying the degrees of freedom of the machine learning model.
Figure 15D:
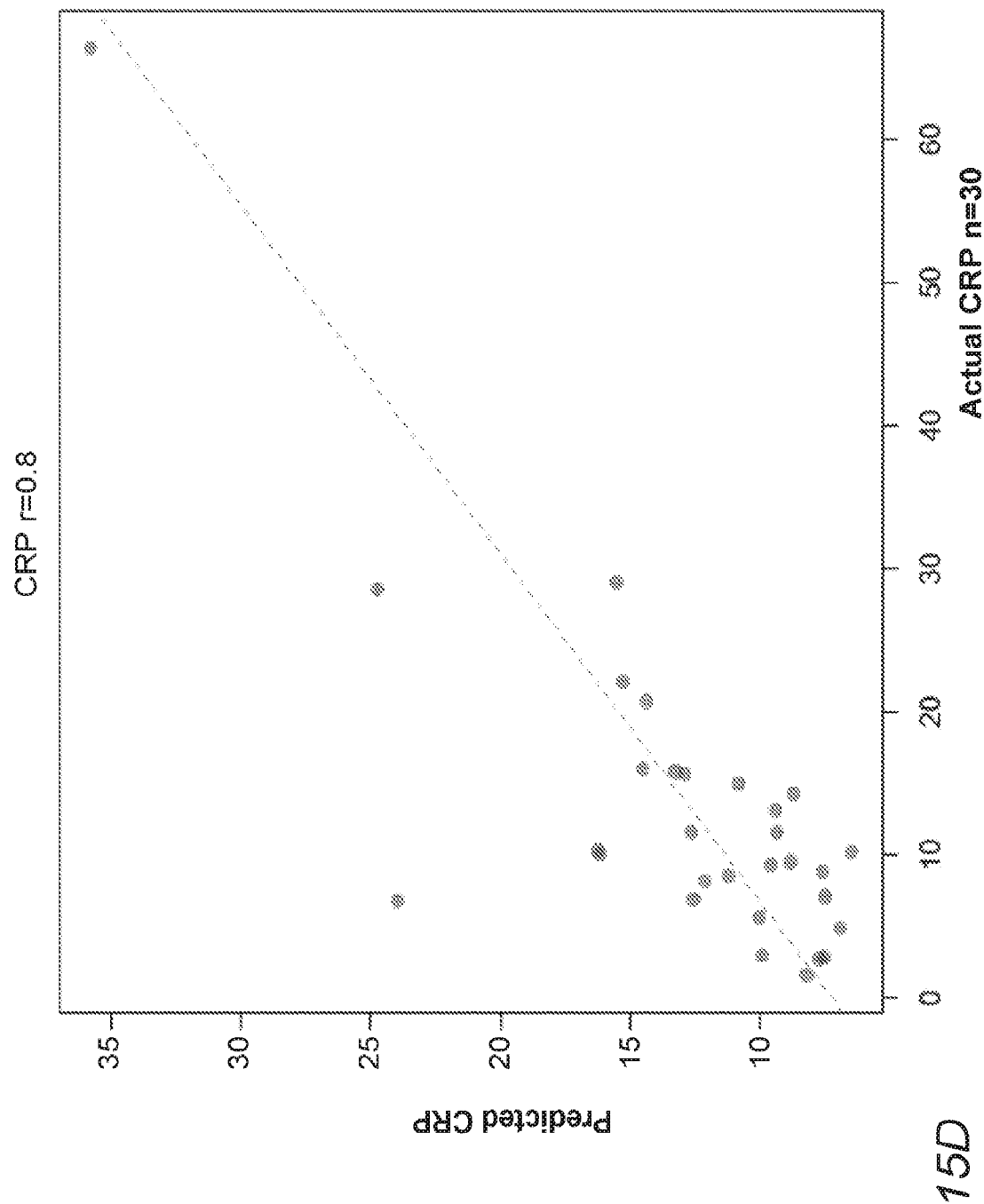
FIG. 15D illustrates prediction accuracy by comparing predicted CRP (using the method as described herein) and actual CRP. The correlation co-efficient (r) is shown above the plot; and the sample size (n) is shown below the plot.

FIG. 15C illustrates mean absolute error (MAE) of a set of predictions on C-reactive protein (CRP) leave-one-out-cross validation while varying the degrees of freedom of the machine learning model. The bottom axis of FIG. 15C displays a unitless parameter setting of the elastic net regression model that controls the degree of freedom that the model has access to. The upper axis of FIG. 15C displays the number of variables selected from the data used to make the prediction. The left vertical axis of FIG. 15C displays the mean absolute error of the predicted CRP level (mg/L), as compared to the measured value across the 10-fold cross-validation as discussed hereinabove.

Figure 16C:
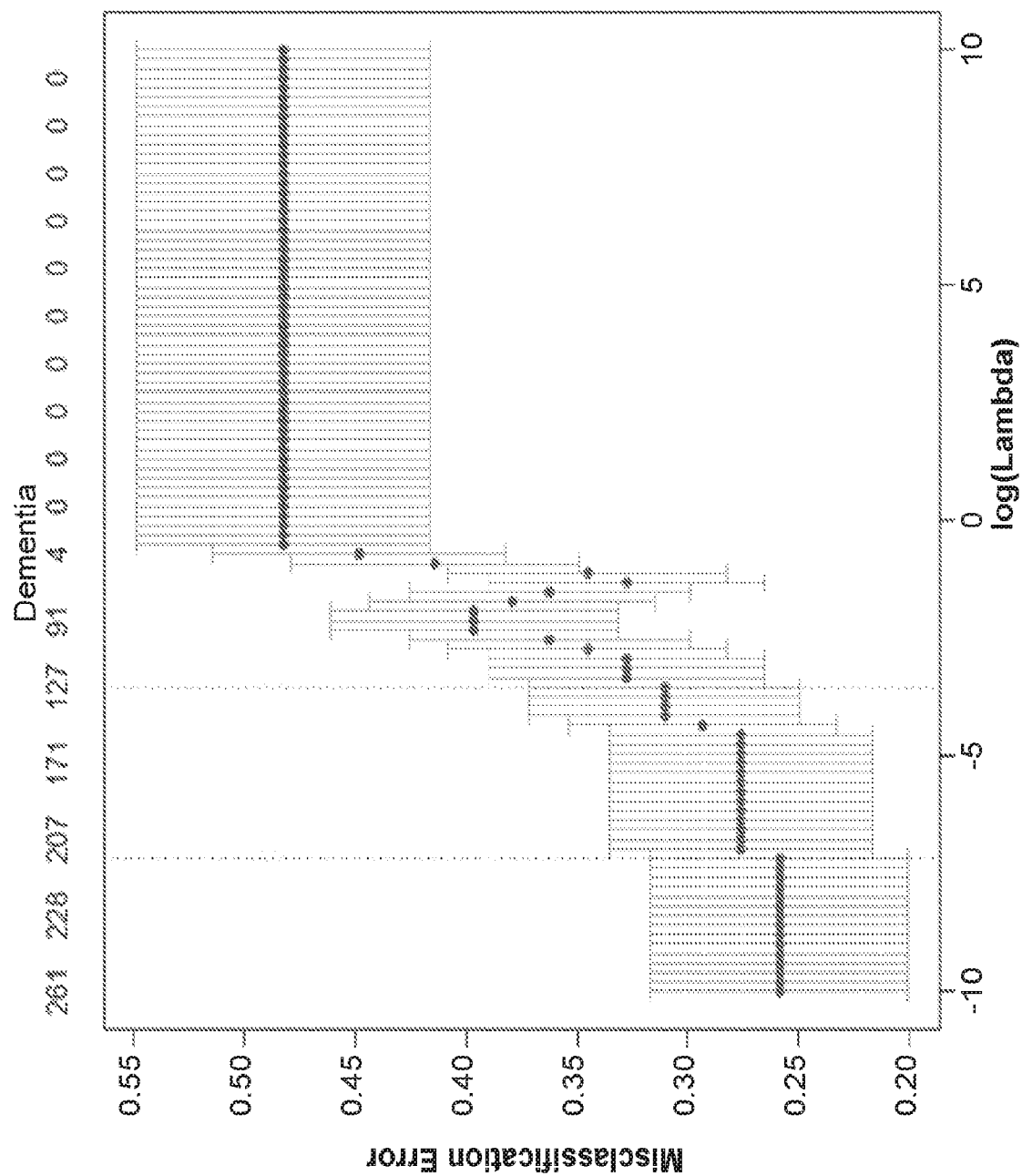
FIG. 16C illustrates mean absolute error (MAE) of a set of predictions on clinical biomarkers associated with dementia leave-one-out-cross validation while varying the degrees of freedom of the machine learning model.
Figure 16D:
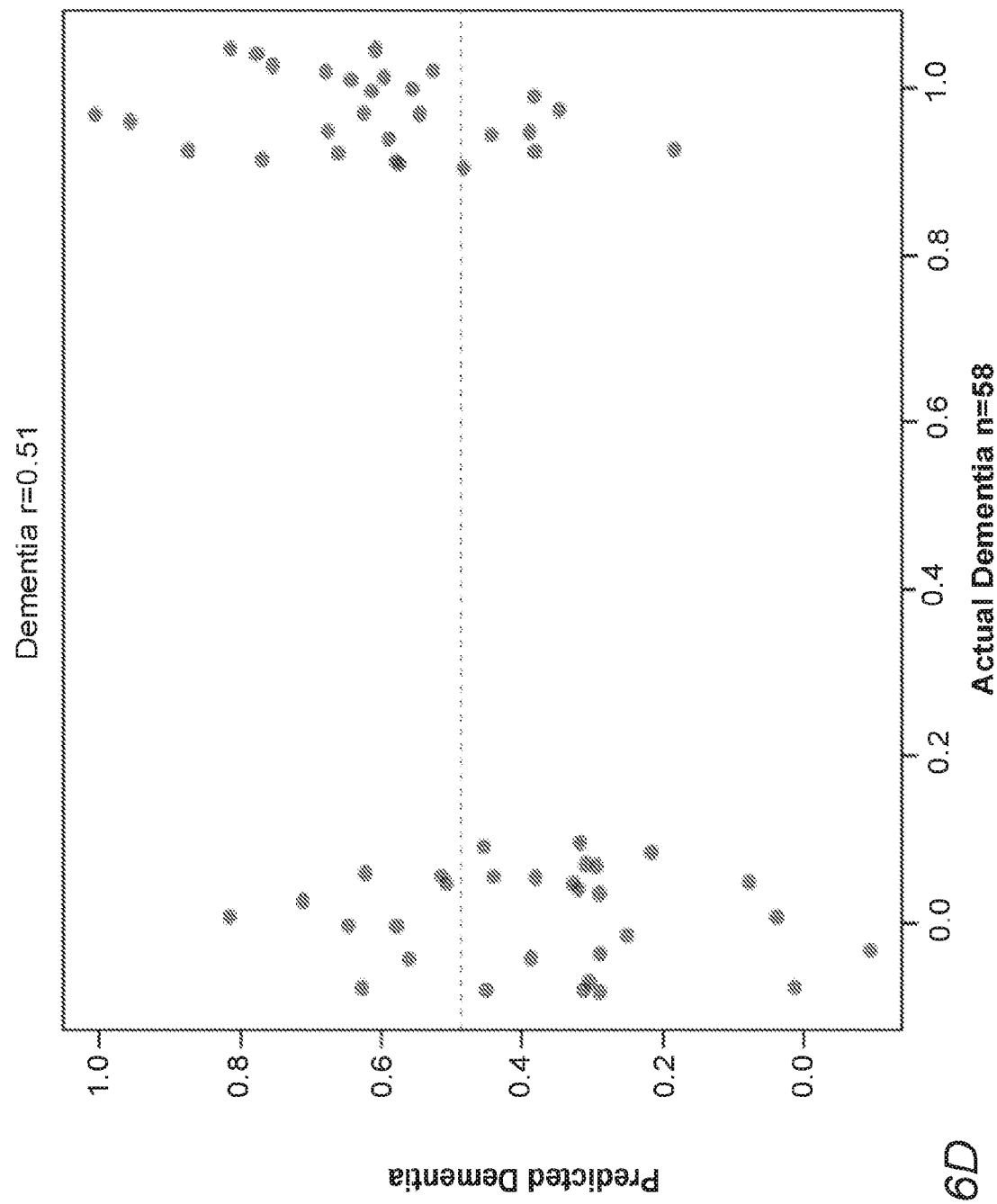
FIG. 16D illustrates prediction accuracy by comparing predicted clinical biomarkers associated with dementia (using the method as described herein) and actual clinical biomarkers associated with dementia. The correlation co-efficient (r) is shown above the plot; and the sample size (n) is shown below the plot.

FIG. 16C illustrates mean absolute error (MAE) of a set of predictions on classification of clinical dementia versus controls using leave-one-out-cross validation while varying the degrees of freedom of the machine learning model. The bottom axis of FIG. 16C displays a unitless parameter setting of the elastic net regression model that controls the degree of freedom that the model has access to. The upper axis of FIG. 16C displays the number of variables selected from the data used to make the prediction. The left vertical axis of FIG. 16C displays the mean absolute error (binary, misclassification error) of dementia-as-predicted as compared to dementia-as-measured across a 10-fold cross-validation (such as one discussed hereinabove).

FIGS. 12D, 13D, 14D, 15D, and 16D each illustrate prediction accuracy by comparing the predicted clinical biomarker (using the method as described herein) and the actual clinical biomarkers. The correlation co-efficient (r) is shown above the plot; and the sample size (n) is shown below the plot.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for substantially simultaneously determining the presence, identities or amounts of a plurality of analytes present in a single sample, the method comprising:
   a. treating the sample with a denaturation treatment thereby forming a denatured sample, wherein the denaturation treatment does not denature components of a normalization reagent when added thereto;
   b. treating the denatured sample with the normalization reagent, capable of being separated by multiple modes of chromatography and individually thereby forming a normalized sample;
   c. treating the normalized sample with an extraction reagent and retaining soluble analyte species and analyte fragment species therein, thereby forming an extracted sample;
   d. subjecting the extracted sample to an instrument to identify the plurality of analytes or derivatives thereof, thereby identifying the plurality of analytes; and
   e. computationally determining from the data the presence, identities or amounts of the plurality of analytes present in the extracted sample.

2. The method of claim 1, wherein the plurality of analytes or derivatives thereof is identified in a single run of the instrument.

3. The method of claim 1, wherein after step c, the extracted sample is subjected to one or more chromatographic separations prior to subjecting the extracted sample to the instrument.

4. The method of claim 1, wherein the instrument is a mass spectrometry (MS) instrument.

5. The method of claim 1, wherein the plurality of analytes comprises 3 or more analytes selected from the group consisting of proteins, carbohydrates, nucleic acids, lipids, electrolytes, metals, small molecules, volatile compounds, and exogenous chemicals.

6. The method of claim 1, wherein the sample is a biological sample.

7. The method of claim 1, wherein the denaturation treatment comprises one or more solvents, one or more chaotropic agents, heat, pressure, irradiation, one or more reference standards, or any combination thereof.

8. The method of claim 7, wherein the denaturation treatment further comprises a metal-chelation agent.

9. The method of claim 1, wherein the denaturation step and treating the denatured sample with the normalization reagent are performed substantially simultaneously.

10. The method of claim 1, wherein the normalization reagent comprises one or more proteinases, one or more nucleases, one or more glycosidases, one or more lipases, one or more chelating agents, one or more buffering agents, one or more reducing agents, one or more derivatizing agents, or any combination thereof.

11. The method of claim 10, wherein the normalization reagent comprises: (a) trypsin, ribonuclease A, EDTA, ammonium bicarbonate or amylase, (b) pancreatic endolytic enzymes, or (c) DNAse I, wherein EDTA is not concurrently present, or any combination thereof.

12. The method of claim 1, wherein the one or more chromatographic separations are selected from the group consisting of a reverse phase separation, a cation exchange separation, an anion exchange separation, an ion pair separation, normal phase separation, an ion mobility separation, a size-exclusion separation, a chiral separation, an affinity separation, a ligand exchange separation, a polar nonionic separation, and any combination thereof.

13. The method of claim 12, wherein a mobile phase used in the chromatography further comprises one or more ionizing adductants selected from ammonium, protons, sodium, acetate, formate, propionate, phosphate, medronate, urea, biuret, triuret, or any combination thereof.

14. The method of claim 1, wherein the instrument is a mass spectrometer and wherein the data acquisition of the mass spectrometer comprises high resolution full scans with low or high resolution MS2 data-independent or data-dependent acquisition with dynamic exclusion in both positive and negative ion modes.

15. The method of claim 1, wherein the step of computationally determining from the data the presence, identities or amounts of the multiple analytes present in the extracted sample comprises comparing the data of the normalized analyte species or normalized analyte fragment species to the mass spectrometry of known amounts of known analytes.

16. A method for determining a disease or condition in a subject from which a biological sample is derived, comprising:
   (i) substantially simultaneously determining the presence, identities or amounts of a plurality of analytes present in the biological sample utilizing method of claim 1; and
   (ii) comparing the presence, identities or amounts of one or more analytes of the plurality of analytes in the biological sample to the presence, identities or amounts of the one or more analytes of a reference; and
   (iii) determining the disease or condition of the subject.

17. The method of claim 16, wherein the comparing step comprises determining one or more differences between the amount of the one or more analytes of the reference and the amount of the one or more analytes of the biological sample to obtain a plurality of difference values; and
   wherein the determining step comprises using a trained machine learning algorithm to determine the disease or condition based on the plurality of difference values.

18. A system for substantially simultaneously determining the presence, identities or amounts of a plurality of analytes present in a single sample, the system comprising:
   (i) a denaturation reagent, wherein the denaturation reagent does not denature components of a normalization reagent when added thereto;
   (ii) a normalization reagent that converts analytes in the sample into normalized analyte species or normalized analyte fragment species;
   (iii) an extraction reagent;
   (iv) a separation apparatus;
   (v) a first instrument configured to generate data on the normalized analyte species and normalized analyte fragment species; and
   (vi) a second instrument configured to computationally determine from the data the presence, identities or amounts of the plurality of analytes present in the sample.

19. A method for determining a disease or condition in a subject from which a biological sample is derived, comprising:
 (i) substantially simultaneously determining the presence, identities or amounts of a plurality of analytes present in the biological sample utilizing the system of claim 18; and
 (ii) comparing the presence, identities or amounts of one or more analytes of the plurality of analytes to the presence, identities or amounts of the one or more analytes of a reference; and
 (iii) determining the disease or condition of the subject.

20. An apparatus for substantially simultaneously determining the presence, identities or amounts of a plurality of analytes present in a single sample, the apparatus comprising:
 (i) means for denaturing biopolymers in the sample, wherein the denaturing does not denature components of a normalization reagent when added thereto;
 (ii) means for normalizing the sample;
 (iii) means for extracting the normalized sample to obtain analyte species and analyte fragment species therein;
 (iv) means for identifying and computationally determining the presence, identities or amounts of the plurality of analytes present in the sample.

* * * * *